United States Patent
Lawit et al.

(10) Patent No.: US 9,175,301 B2
(45) Date of Patent: Nov. 3, 2015

(54) USE OF DIMERIZATION DOMAIN COMPONENT STACKS TO MODULATE PLANT ARCHITECTURE

(75) Inventors: Shai J Lawit, Urbandale, IA (US); Dwight T Tomes, Grimes, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 655 days.

(21) Appl. No.: 12/837,553

(22) Filed: Jul. 16, 2010

(65) Prior Publication Data

US 2011/0023190 A1     Jan. 27, 2011

Related U.S. Application Data

(60) Provisional application No. 61/228,195, filed on Jul. 24, 2009, provisional application No. 61/286,061, filed on Dec. 14, 2009.

(51) Int. Cl.
  *C12N 15/82* (2006.01)
  *C07H 21/04* (2006.01)
  *C12N 5/10* (2006.01)
  *C07K 14/415* (2006.01)

(52) U.S. Cl.
  CPC .......... *C12N 15/8242* (2013.01); *C07K 14/415* (2013.01); *C12N 15/827* (2013.01); *C12N 15/8261* (2013.01); *C12N 15/8293* (2013.01); *C12N 15/8297* (2013.01)

(58) Field of Classification Search
  None
  See application file for complete search history.

(56) References Cited

U.S. PATENT DOCUMENTS

| | | | |
|---|---|---|---|
| 5,633,441 A * | 5/1997 | De Greef et al. | 800/271 |
| 6,077,994 A | 6/2000 | Coupland et al. | |
| 6,140,085 A | 10/2000 | Dean et al. | |
| 6,265,637 B1 | 7/2001 | Coupland et al. | |
| 6,307,126 B1 | 10/2001 | Harberd et al. | |
| 6,310,271 B1 | 10/2001 | Hanson et al. | |
| 6,573,430 B1 | 6/2003 | Bradley et al. | |
| 6,670,526 B1 | 12/2003 | Coupland | |
| 6,762,348 B1 | 7/2004 | Harberd et al. | |
| 6,794,560 B2 | 9/2004 | Harberd | |
| 6,830,930 B2 | 12/2004 | Harberd | |
| 6,887,708 B1 | 5/2005 | Coupland | |
| 6,949,694 B2 | 9/2005 | Simpson | |
| 7,045,682 B1 | 5/2006 | Dean et al. | |
| 7,268,272 B2 | 9/2007 | Harberd et al. | |
| 2002/0102695 A1 | 8/2002 | Silva et al. | |
| 2003/0101481 A1 | 5/2003 | Zhang et al. | |
| 2004/0019927 A1 | 1/2004 | Sherman et al. | |
| 2004/0034888 A1 * | 2/2004 | Liu et al. | 800/289 |
| 2004/0045049 A1 | 3/2004 | Zhang et al. | |
| 2004/0214272 A1 | 10/2004 | La Rosa et al. | |
| 2005/0039227 A1 | 2/2005 | Harberd | |
| 2005/0066394 A1 | 3/2005 | Danilevskaya | |
| 2005/0071897 A1 | 3/2005 | Harberd | |
| 2006/0059586 A1 | 3/2006 | Cheng et al. | |
| 2006/0236419 A1 | 10/2006 | La Rosa et al. | |
| 2009/0158452 A1 * | 6/2009 | Johnson et al. | 800/260 |

FOREIGN PATENT DOCUMENTS

| | | |
|---|---|---|
| EP | 1 586 652 A1 | 10/2005 |
| WO | 9502060 A1 | 1/1995 |
| WO | 9605317 A1 | 2/1996 |
| WO | 9729123 A2 | 8/1997 |
| WO | 9741152 A1 | 11/1997 |
| WO | 9743419 A2 | 11/1997 |
| WO | 9909174 A1 | 2/1999 |
| WO | 0233091 A1 | 4/2002 |
| WO | 2007124312 A2 | 11/2007 |

OTHER PUBLICATIONS

Lazar et al. Mol Cell Biol 8(3):1247-52 (1988).*
NCBI Blast_SEQ ID NO_41 as query; SEQ ID NO_19 as subject_553_1014_2014.*
NCBI Blast_SEQ ID NO_41 as query; SEQ ID NO_21 as subject_553_1014_2014.*
Guo et al_Proc Natl Acad Sci_101_9205-10_2004.*
Lawit et al., Plant Cell Physiol 51(11):1854-68 (2010).*
Takaiwa_Jpn J Genet_66_161_1991.*
Wu_Plant Cell Physiol_38_885_1998.*
Bird, C.R. and Ray, J.A.; "Manipulation of Plant Gene Expression by Antisense RNA"; Biotechnology and Genetic Engineering Reviews (Dec. 1991) 9:207-227; Intercept Ltd.; Hampshire UK.
Okamuro, J.K.; "The AP2 domain of APETALA2 defines a large new family of DNA binding proteins in Arabidopsis"; Proc Natl Acad Sci USA (Jun. 1997) 94:7076-7081; National Academy of Sciences; Washington, DC US.
Itoh, H., et al.; "The Gibberellin Signalling Pathway is Regulated by the Appearance and Disappearance of SLENDER RICE1 in Nuclei"; The Plant Cell (Jan. 2002) 14:57-70; American Society of Plant Biologists; Rockville, MD US.
Sun, T. and Gubler, F.; "Molecular Mechanism of Gibberellin Signalling in Plants"; Annu Rev Plant Biol (2004) 55:197-223; Annual Reviews; Palo Alto, CA US.
Peng, J., et al.; "'Green revolution' genes encode mutant gibberellin response modulators"; Nature (Jul. 15, 1999) 400:256-261; Macmillan Magazines Ltd. US.
Cassani, E., et al.; "Characterization of the first dominant dwarf maize mutant carrying a single amino acid insertion in the VHNP domain of the dwarf8 gene"; Mol Breeding (2009) 24:375-385; Kluwer Academic Publishers; The Netherlands.

(Continued)

*Primary Examiner* — David H Kruse
*Assistant Examiner* — Russell Boggs
(74) *Attorney, Agent, or Firm* — Pioneer Hi-Bred Int'l, Inc.

(57) ABSTRACT

This invention provides means for altering the harvest index of crop plants by modulating the expression of transgenic genes using dimerization domain and component stacks, thereby modulating plant architecture. The transgene/dimerization domain stacks are provided in a single transformation vector unit and are used to modulate plant growth, yield, and harvest index in plants.

13 Claims, 5 Drawing Sheets

(56) References Cited

OTHER PUBLICATIONS

Vahala, T., et al.; "Two APETALA2-like genes of Picea abies are differentially expressed during development"; Journal of Experimental Botany (2001) 52(358):1111-1115; Society for Experimental Biology; Southhampton UK.

Trevaskis, B., et al.; "MADS box genes control vernalization-induced flowering in cereals"; PNAS (Oct. 28, 2003) 100(22):13099-13104; National Academy of Sciences; United States.

Hartmann, U., et al.; "Molecular cloning of SVP: a negative regulator of the floral transition in Arabidopsis"; The Plant Journal (2000) 21(4):351-360; Blackwell Science Ltd.; Oxford, UK.

Masiero, S., et al.; "Incomposita: a MADS-box gene controlling prophyll development and floral meristem identity in Antirrhinum"; Development (2004) 131:5981-5990; The Company of Biologists; Cambridge, UK.

Purugganan, M.D., et al.; "Molecular Evolution of Flower Development: Diversification of the Plant MADS-Box Regulatory Gene Family"; Genetics (May 1995) 140:345-356; The Genetics Society of America; Pittsburgh, PA, United States.

Saedler, H., et al.; "MADS-box genes are involved in floral development and evolution"; Acta Biochimica Polonica (2001) 48(2):351-358; Institute of Experimental Biology; Poland.

Blazquez, M., et al.; "Flowering on time: genes that regulate floral transition"; EMBO Reports (2001) 2 (12):1078-1082; European Molecular Biology Organization; London, UK.

Hong-Bo, S., et al.; "Plant Gene Regulatory Network System Under Abiotic Stress"; Acta Biologica Szegediensis (2006) 50(1-2):1-9; Univeristy of Szeged; Szeged, Hungary.

Wen, C., et al.; "Arabidopsis RGL1 Encodes a Negative Regulator of Gibberellin Responses"; The Plant Cell (Jan. 2002) 14:87-100; American Society of Plant Pathologists; Rockville, MD, US.

Ashikari, M., et al.; "Rice Gibberellin-insensitive dwarf mutant gene Dwarf 1 encodes the alpha-subunit of GTP-binding protein"; Proc Natl Acad Sci USA (Aug. 1999) 96:10284-10289; National Academy of Sciences; Washington, DC US.

Alvey, L., et al.; "DELLA proteins: integrators of multiple plant growth regulatory inputs?"; Physiologia Plantarum (2005) 123:153-160; Munksgaard International Publishers Ltd.; Copenhagen, Denmark.

Sun, T.; "Gibberellin signal transduction"; Current Opinion in Plant Biology (2000) 3:374-380; Elsevier Science Ltd; Amsterdam, The Netherlands.

Peng, J., et al.; "The Arabidopsis Gai gene defines a signaling pathway that negatively regulates gibberellin responses"; Genes & Development (1997) 11:3194-3205; Cold Spring Harbor Laboratory Press; Cold Spring Harbor, NY, US.

Bowie, J.U., et al.; "Decipering the Message in Protein Sequences: Tolerance to Amino Acid Substitutions"; Science (1990) 247:1306-1310; American Association for the Advancement of Science; Washington, DC US.

McConnell, J.R., et al.; "Role of Phabulosa and Phavoluta in determining radial patterning in shoots"; Nature (2001) 411:709-713; Nature Publishing Group; London, UK.

Benfey, P.N. and Chua, N-H.; "The Cauliflower Mosaic Virus 35S Promoter: Combinatorial Regulation of Transcription in Plants"; Science (1999) 250(4983):959-966; American Association for the Advancement of Science; Washington, DC US.

Benfey, P.N. et al.; "The CaMV 35S enhancer contains at least two domains which can confer different development and tissue-specific expression patterns", The EMBO Journal (1989) 8(8): 2195-2202; IRL Press Limited; Oxford, UK.

Kano-Murakami, Y., et al.; "A rice homeotic gene, OSH1, causes unusual phenotypes in transgenic tobacco"; FEBS (1993) 334(3):365-368; Federation of European Biochemical Societies; Elsevier Science Publishers; Amsterdam, The Netherlands.

Peng, J. and Harberd, N. P.; "Derivative Alleles of the Arabidopsis Gibberellin-Insensitive (gai) Mutation Confer a Wild-Type Phenotype"; The Plant Cell (Mar. 1993) 5:351-360; American Society of Plant Physiologists; Rockville, MD US.

Newman, T., et al.; "Genes Galore: A Summary of Methods for Accessing Results from Large-Scale Partial Sequencing of Anonymous Arabidopsis cDNA Clones"; Plant Phyiol (1994)106:1241-1255; America Society of Plant Biologists; Rockville, MD US.

Wilson, R.N. and Somerville, C.R.; "Phenotypic Suppression of the Gibberellin-Insensitive Mutant (gai) of Arabidopsis"; Plant Physiol (1995) 108:495-502; America Society of Plant Biologists; Rockville, MD US.

Hooley, R.; "Gibberellins: perception, transduction and responses"; Plant Molecular Biology (1994) 26:1529-1555; Kluwer Academic Publishers; Belgium.

Harberd, N.P. and Freeling, Michael; "Genetics of Dominant Gibberellin-Insensitive Dwarfism in Maize"; Genetics (1989) 121:827-838; Genetics Society of America; Pittsburgh, PA US.

Carol, P., et al.; "Isolation and preliminary characterization of gas1-1, a mutation causing partial suppression of the phenotype conferred by the gibberellin-insensitive (gai) mutation in Arabidopsis thaliana (L.) Heyhn"; Planta (1995) 197:414-417; Springer-Verlag; Berlin/Heidelberg, Germany.

Fu, X., et al.; "Expression of Arabidoposis GAI in Transgenic Rice Represses Multiple Gibberellin Responses"; The Plant Cell (2001) 13:1791-1802; American Society of Plant Biologists; Rockville, MD US.

Riechmann, J.L. and Ratcliffe, O.J.; "A genomic perspective on plant transcription factors"; Current Opinion in Plant Biology (2000) 3:423-434; Elsevier Science Ltd.; Amsterdam, The Netherlands.

Rosin, F.M., et al.; "Suppression of a Vegetative MADS Box Gene of Potato Activates Axillary Meristem Development"; Plant Physiology (2003) 131(4):1613-1622; American Society of Plant Biologists; Rockville, MD US.

Colliver, S.P., et al.; "Differential modification of flavonoid and isoflavonoid biosynthesis with an antisense chalcone snythase construct in transgenic Lotus corniculatus"; Plant Molecular Biology (1997) 35:509-522; Kluwer Academic Publishers, Belgium.

Napoli, C., et al.; "Introduction of a Chimeric Chalcone Synthase Gene into Petunia Results in Reversible Co-Suppression of Homologous Genes in trans"; The Plant Cell (1990) 2:279-289; America Society of Plant Physiologists; Rockville, MD US.

Lazar, E., et al.; "Transforming Growth Factor alpha: Mutation of Aspartic Acid 47 and Leucine 48 Results in Different Biological Activities"; Molecular and Cellular Biology (Mar. 1988) 8(3):1247-1252; American Society for Microbiology; Rockville, MD US.

Chory, J., et al.; "A Role for Cytokinins in De-Etiolation in Arabidopsis"; Plant Physiol (1994) 104:339-347; American Society of Plant Biologists; Rockville, MD US.

Sandler, S.J., et al.; "Inhibition of gene expression in transformed plants by antisense RNA"; Plant Molecular Biology (1988) 11:301-310; Kluwer Academic Publishers, Dordrecht; The Netherlands.

Smith, C.J.S., et al.; "Antisense RNA inhibition of polygalacturonase gene expression in transgenic tomatoes"; Nature (1988) 334:724-726; Nature Publishing Group; London UK.

Salvi, S., et al.; "Toward positional cloning of Vgt1, a QTL controlling the transition from the vegetative to the reproductive phase in maize"; Plant Molecular Biology (2002) 48:601-613; Kluwer Academic Publishers; The Netherlands.

Maes, T., et al.; "Petunia Ap2-like Genes and Their Role in Flower and Seed Development"; The Plant Cell (2001) 13:229-244; American Society of Plant Physiologists; Rockville, MD US.

Schmid, M., et al.; "Dissection of floral induction pathways using global expression analysis"; Development (2003) 130:6001-6012; The Company of Biologists; Cambridge UK.

Aukerman, M.J. and Sakai, H.; "Regulation of Flowering Time and Floral Organ Identity by a MicroRNA and Its APETALA2-Like Target Genes"; The Plant Cell (2003) 15:2730-2741; American Society of Plant Biologists; Rockville, MD US.

Chuck, G., et al.; "The control of maize spikelet meristem fate by the APETALA2-like gene indeterminate spikelet1"; Genes & Development (1998) 12:1145-1154; Cold Spring Harbor Laboratory Press; Cold Spring Harbor, NY US.

(56) References Cited

OTHER PUBLICATIONS

Ikeda, A., et al.; "slender Rice, a Constitutive Gibberellin Response Mutant, Is Cause by a Null Mutation of the SLR1 Gene, an Ortholog of the Height-Regulating Gene GAI/RGA/RHT/D8"; The Plant Cell (2001) 13:999-1010; American Society of Plant Physiologists; Rockville, MD US.

Winkler, R.G and Freeling, M.; "Physiological genetics of the dominant gibberellin-nonresponsive maize dwarfs, Dwarf8 and Dwarf9"; Planta (1994) 193:341-348; Springer-Verlag; Berlin/Heidelberg, Germany.

Silverston, A. and Sun, T.; "Gibberellins and the Green Revolution"; Trends in Plant Science (Jan. 2000) 5 (1):1-2; Elsevier, Ltd.; Oxford, UK.

Wells, J.; "Additivity of Mutational Effects in Proteins"; Biochemistry (1990) 29(37):8509-8517; American Chemical Society; Washington, DC US.

Keskin, O., et al.; "A new, structurally nonredundant, diverse data set of protein-protein interfaces and its impliations"; Protein Science (2004) 13:1043-1055; The Protein Society; Bethesda, MD US.

Yang, D., et al.; "Expression of the REB transcriptional activator in rice grains improves the yeild of recombinant proteins whose genes are controlled by a Reb-responsive promoter"; PNAS (2001) 98(20):11438-11443; National Academy of Sciences; Washington, DC US.

Database EMBL Accession Number: CC639651, "OGLAZO4TV ZM_0.7_1.5_KB ZEA Mays Genomic Clone ZMMBMa0312B08, Genomic Survey Sequence"; Jun. 20, 2003, 2 pages.

Database EMBL Accession Number: CC379756, "PUHKS07TB ZM_0.6_1.0_KB ZEA Mays Genomic Clone ZMMBTa473B13, DNA Sequence"; May 20, 2003, 2 pages.

Database EMBL Accession Number: CG240742, "OG1DY21TV ZM_0.7_1.5_KB ZEA Mays Genomic Clone ZMMBMa0740D17, Genomic Survey Sequence" Aug. 25, 2003, 2 pages.

Riechmann, J.L. and Meyerowitz, E.M.; "The AP2/EREBP Family of Plant Transcription Factors"; Biol Chem (1998) 379:633-646; Walter de Gruyler & Co.; Berlin/New York.

Gale, M.D. and Devos, K.M.; "Comparative genetics in the grasses"; PNAS (1998) 95:1971-1974; National Academy of Sciences; Washington, DC US.

Database EMBL Accession Number: AJ242530, "Zea mays partial d8 gene for gibberellin response modulator"; Jul. 28, 1999, 2 pages.

Database EMBL Accession Number: DQ903073, "Zea mays dwarf plant9 (d9) mRNA, d9-B73 allele, partial cds."; Sep. 25, 2006, 2 pages.

Ngo, J.T., et al.; "Coputational Complexity, Protein Structure Prediction, and the Levinthal Paradox"; The Protein Folding Problem and Tertiary Structure Prediction; Merz and Le Grand eds. pp. 492-495; 1994; Birkhauser, Boston, MA US.

Guo, H.H., et al.; "Protein Tolerance to random amino acid change"; PNAS (2004) 101:9205-9210; National Academy of Sciences; Washington, DC US.

Thornton, J.M., et al.; "From structure to function: Approaches and limitations"; Nature Structural Biology; Structural Genomics Supplement (Nov. 2000) 991-994; Nature America Inc.; US.

Jacobsen, S.E., et al.; "SPINDLY, a tetratricopeptide repeat protein involved in gibberellin signal transduction in Arabidopsis"; PNAS USA (1996) 93:9292-9296; National Academy of Sciences; Washington DC US.

Dill, A., et al.; "The DELLA motif is essential for gibberellin-induced degradation of RGA"; PNAS USA (2001) 98(24) 14162-14167; National Academy of Sciences; Washington DC US.

Di Laurenzio, L.; "The SCARECROW Gene Regulates an Asymmetric Cell Division That Is Essential for Generating the Radial Organization of the Arabidopsis Root"; Cell (1996) 86:423-433; Elseiver Inc., Boston, MA US.

Truong, H-N., et al.; "Sequence and characterization of two Arabidopsis thaliana cDNAs isolated by functional complementation of yeast gln3 gdhl mutant"; FEBS Letters (1997) 410:213-218; Blackwell Publishing, Oxford UK.

Hill, M.A. and Preiss, J.; "Functional Analysis of Conserved Histidines in ADP-Glucose Pyrophosphorylase from *Escherichia coli*"; Biochemical and Biophysical Research Communications (1998) 244:573-577; Elseiver, The Netherlands.

Broun, P., et al.; "Catalytic Plasticity of Fatty Acid Modification Enzymes Underlying Chemical Diversity of Plant Lipids"; Science (1998) 282:1315-1317; American Association for the Advancement of Science; Washington, DC US.

Lawit, et al.; "Maize DELLA Proteins dwarf plant8 and dwarf plant9 as Modulators of Plant Development"; Plant Cell Physiol. (2010) 51(11):1854-1868; Oxford University Press; Oxford UK.

\* cited by examiner

```
SEQ ID NO: 24  (154) NGIRLVHSLMACAEAVENNNLAVAEALVKQIGFLALSQVGAMRKVATYFA
SEQ ID NO: 26  (153) NGIRLVHSLMACAEAVENNNLAVAEALVKQIGFLAVSQVGAMRKVAIYFA
SEQ ID NO: 28  (214) AGVRLVHTLLACAEAVQQENLKLADALVKEHVGILAASQAGAMRKVASYFA
SEQ ID NO: 30  (205) AGVRLVHTLLACAEAVQQENLKLADALVKHVGILAASQAGAMRKVASYFA
SEQ ID NO: 32  (165) NGVRLVHALIACAEAVQKENLTVAEALVKQIGFLAVSQIGAMRKVATYFA
SEQ ID NO: 34  (217) NGVRLVHALLACAEAIQQNNLTLAEALVKQIGCLAVSQAGAMRKVATYFA
SEQ ID NO: 36  (148) TGVRLVHALLACAEAVQQNNLKLADALVKEHVGLLASSQAGAMRKVATYFA
SEQ ID NO: 38  (176) TGVRLVHALVACAEAIHQENLNLADALVKRVGTLAGSQAGAMGKVATYFA
SEQ ID NO: 40  (153) TGVRLVQALVACAEAVQLENLSLADALVKPVGLLAASQAGAMRKVATYFA
SEQ ID NO: 19  (1)   ---MLVHALLACAEAVQQENFSAAEALVKQIPMLASSQGGAMRKVAAYFG
SEQ ID NO: 41        GVRLVHALLACAEAVQQENLXLADALVKQIGILAASQAGAMRKVATYFA
                                                                    287

SEQ ID NO: 24  (204) EALARRIYRVFP------QQHSLSDSLQIHFYETCPYLKFAHFTANQ
SEQ ID NO: 26  (203) EALARRIYRVFP------LQHSLSDSLQIHFYETCPYLKFAHFTANQ
SEQ ID NO: 28  (264) QALARRIYGIFP------EETLDSSFSDVLHMHFYESCPYLKFAHFTANQ
SEQ ID NO: 30  (255) QALARRIYGIFP------EETLDSSFSDVLHMHFYESCPYLKFAHFTANQ
SEQ ID NO: 32  (215) EALARRIYRLSP------SQSPIDHSLSDTLQMHFYETCPYLKFAHFTANQ
SEQ ID NO: 34  (267) EALARRIYRLSPP-----QNQIDHCLSDTLQMHFYETCPYLKFAHFTANQ
SEQ ID NO: 36  (198) EGLARRIYRIYPR-----DDVALSSFSDTLQIHFYESCPYLKFAHFTANQ
SEQ ID NO: 38  (226) QALARRIYRDYTAETDVCAAVNPSFEEVLEMHFYESCPYLKFAHFTANQ
SEQ ID NO: 40  (203) EALARRIYRIHPS-----AAAIDPSFEEILQMNFYDSCPYLKFAHFTANQ
SEQ ID NO: 19  (48)  EALARRVYRFRPPP--DSSLLDAAFADLHAHFYESCPYLKFAHF----
SEQ ID NO: 41        EALARRIYRIFPXXXXXLDXSFSDVLQMHFYESCPYLKFAHFTANQ
                                                                    336
```

FIGURE 5

SEQUENCE LISTING

```
<160> NUMBER OF SEQ ID NOS: 43

<210> SEQ ID NO 1
<211> LENGTH: 879
<212> TYPE: DNA
<213> ORGANISM: Medicago sativa

<400> SEQUENCE: 1
aattcccatg atcttctctc cttcatcaat ggatgccatg tttcataaca ataacaccaa     60
atgtttgatg agctaccaac aattgcgcaa agactatggc taagctcgag ctcgctcgct    120
acaagttgtt gactttcaaa tacaagtttg tttttggaac accaaatatt ctacatgatc    180
tttcactaag ttgcgcacca ctatcaaaag attatctagg ccattattca agtaaagagt    240
gaacacgtct aagacccaca accacaccaa atagaatacg catacatgca acatattgtg    300
caagaagtat ccaactggac tcccatgtat tctaaaacta ttttcgtaga gttaaagtta    360
tgacaaactt atcaaataaa aatttgaacg ctggaccaaa actttcatct ttcaaatcca    420
ccatcgtcta tcctcataaa ttgttttgat tataacacat ctacgtaaat catttgtttt    480
gaacaatact aatttaattt tattaagtca aataacctgc ttagaaaata atccctccac    540
ctcatttaac aatttcttgt caaacacaca ccaagaaaaa aattaatgaa agagaaaaga    600
aatgaaaagg acatggagtt gaatactagc aaaattgatt gaaggaagat tcacaattga    660
aattgaaacc atttaattta ttttcgggtc cataataata aattggtaag aataaaaacc    720
cgatcaagtc cggtacagta caattccact ccaccaactc cttacttaaa cccctattta    780
tacccactct catcctcact cttccttcac ctctcacact ctcttctctc tctcaaaacc    840
ctcacacaaa cgctgcgttt agtgtaagaa attcaatcc                           879

<210> SEQ ID NO 2
<211> LENGTH: 3237
<212> TYPE: DNA
<213> ORGANISM: Zea mays

<400> SEQUENCE: 2
atggacgccg gctcggtcac cggtggcctc gccgcgggct cgcacatgcg ggacgagctg     60
catgtcatgc gcgcccgcga ggagccgaac gccaaggtcc ggagcgccga cgtgaagacg    120
```

```
tgccgcgtgt gcgccgacga ggtcgggacg cgggaggacg ggcagcccctt cgtggcgtgc    180 gccgagtgcg gcttccccgt ctgccggccc tgctacgagt acgagcgcag cgagggcacg    240
cagtgctgcc cgcagtgcaa cacccgctac aagcgccaga aagggtgccc gagggtggaa    300
ggggacgagg aggagggccc ggagatggac gacttcgagg acgagttccc cgccaagagc    360
cccaagaagc ctcacgagcc tgtcgcgttc gacgtctact cggagaacgg cgagcacccg    420
gcgcagaaat ggcggacggg tggccagacg ctgtcgtcct tcaccggaag cgtcgccggg    480
aaggacctgg aggcggagag ggagatggag gggagcatgg agtggaagga ccggatcgac    540
aagtggaaga ccaagcagga gaagaggggc aagctcaacc acgacgacag cgacgacgac    600
gacgacaaga acgaagacga gtacatgctg cttgccgagg cccgacagcc gctgtggcgc    660
aaggttccga tcccgtcgag catgatcaac ccgtaccgca tcgtcatcgt gctccgcctg    720
gtggtgctct gcttcttcct caagttccgg atcacgacgc ccgccacgga cgccgtgcct    780
ctgtggctgg cgtccgtcat ctgcgagctc tggttcgcct tctcctggat cctggaccag    840
ctgccaaagt gggcgccggt gacgcgggag acgtacctgg accgcctggc gctgcggtac    900
gaccgtgagg cgcgaggcgtg ccggctgtcc cccatcgact tcttcgtcag cacggtggac    960
ccgctcaagg agccgcccat catcaccgcc aacaccgtgc tgtccatcct cgccgtcgac   1020
taccccgtgg accgcgtcag ctgctacgtc tccgacgacg cgcgtccat gctgctcttc   1080 gacgcgctgt ccgagaccgc cgagttcgcg cgccgctggg tgcccttctg caagaagttc   1140
gccgtggagc cgcgcgcccc ggagttctac ttctcgcaga agatcgacta cctcaaggac   1200
aaggtgcagc cgacgttcgt caaggagcgc cgcgccatga gagggagta cgaggagttc   1260 aaggtgcgca tcaacgcgct ggtggccaag gcgcagaaga agcccgagga ggggtgggtc   1320
atgcaggacg gcacgccgtg gcccgggaac aacacgcgcg accacccggg tatgatccag   1380
gtctacctcg gcaaccaggg cgcgctggac gtggagggcc acgagctgcc gcgcctcgtc   1440
tacgtgtccc gtgagaagcg ccccgggtac aaccaccaca gaaggcgggg cgccatgaac   1500
gcgctggtgc gcgtctccgc cgtgctcacc aacgcgccct tcatcctcaa cctcgactgc   1560
gaccactacg tcaacaacag caaggccgtg cgcgaggcca tgtgcttcct catgaccccg   1620
cagctgggga agaagctctg ctacgtccag ttcccgcagc gcttcgatgg catcgatcgc   1680
cacgaccgat acgccaaccg caacgtcgtc ttcttcgaca tcaacatgaa ggggctggac   1740
ggcatccagg gcccggtgta cgtcggcacg gggtgcgtgt tcaaccgcca ggcgctgtac   1800
ggctacgacc cgccgcggcc cgagaagcgg cccaagatga cgtgcgactg ctggccgtcg   1860
tggtgctgct gctgctgctg cttcggcggc ggcaagcgcg gcaaggcgcg caaggacaag   1920
aagggcgacg gcgcgagga gccgcgccgg ggcctgctcg gcttctacag gaagcggagc   1980
aagaaggaca agctcggcgg cgggtcggtg gccggcagca gaaagggcgg cgggctgtac   2040
aagaagcacc agcgcgcgtt cgagctggag gagatcgagg aggggctgga ggggtacgac   2100
gagctggagc gctcctcgct catgtcgcag aagagcttcg agaagcggtt cggccagtcg   2160
cccgtgttca tcgcctccac gctcgtcgag gacggcggcc tgccgcaggg cgccgccgcc   2220
gaccccgccg cgctcatcaa ggaggccatc cacgtcatca gctgcggata cgaggagaag   2280
accgagtggg gcaaggagat tgggtggatc tatgggtcgg tgacagagga tatcctgacg   2340
gggttcaaga tgcactgccg ggggtggaag tccgtgtact gcacgccgac acggccggcg   2400 ttcaagggt cggcgcccat caacttgtct gatcgtctcc accaggtgct gcgctgggcg   2460
ctggggtccg tggagatctt catgagccgc cactgcccgc tccggtacgc ctacggcggc   2520
```

```
cggctcaagt ggctggagcg cttcgcctac accaacacca tcgtgtaccc cttcacctcc    2580
atcccgctcc tcgcctactg caccatcccc gccgtctgcc tgctcaccgg caagttcatc    2640
attcccacgc tgaacaacct cgccagcatc tggttcatcg cgctcttcct gtccatcatc    2700
gcgacgagcg tcctggagct gcggtggagc ggggtgagca tcgaggactg gtggcgcaac    2760
gagcagttct gggtcatcgg cggcgtgtcc gcgcatctct tcgccgtgtt ccagggcttc    2820
ctcaaggttc tgggcggcgt ggacaccagc ttcaccgtca cctccaaggc ggccggcgac    2880
gaggccgacg ccttcgggga cctctacctc ttcaagtgga ccaccctgct ggtgccccc    2940 accacgctca tcatcatcaa catggtgggc atcgtggccg gcgtgtccga cgccgtcaac    3000
aacggctacg gctcctgggg cccgctcttc ggcaagctct tcttctcctt ctgggtcatc    3060
gtccacctct acccgttcct caaggggctc atggggaggc agaaccggac gcccaccatc    3120
gtcgtgctct ggtccatcct cctcgcctcc atcttctcgc tcgtctgggt caggatcgac    3180
ccgtttatcc cgaaggccaa gggccccatc ctcaagccat gcggagtcga gtgctga      3237

<210> SEQ ID NO 3
<211> LENGTH: 319
<212> TYPE: DNA
<213> ORGANISM: Zea mays

<400> SEQUENCE: 3
caacctagac ttgtccatct tctggattgg ccaacttaat taatgtatga ataaaagga     60 tgcacacata gtgacatgct aatcactata atgtgggcat caaagttgtg tgttatgtgt    120
aattactagt tatctgaata aaagagaaag agatcatcca tatttcttat cctaaatgaa    180
tgtcacgtgt ctttataatt ctttgatgaa ccagatgcat ttcattaacc aaatccatat    240
acatataaat attaatcata tataattaat atcaattggg ttagcaaaac aaatctagtc    300
taggtgtgtt ttgcgaatt                                                 319

<210> SEQ ID NO 4
<211> LENGTH: 748
<212> TYPE: DNA
<213> ORGANISM: Zea mays

<400> SEQUENCE: 4
catggtggca cagaatcgag ttgatgttgt agctggcggc tagggtttga agtggagaag    60
aggtccggct ggtggcatcc tatcgtctat tgagggttgg gtccggtggc atcatacttg    120
atgacaattg aaagtaattt taatcaactt gtcatgagta gtgagtcttt tataaaaaat    180
aagctgaaat aagcacccct tgatgagctt ataggattat cataatctca aatgctaaat    240
tatataattt tattagataa gttgcttgtt tgtttcccca ctagcttatt tacattggat    300
tatataatct acataaatta taatctcaaa caaaaagtcc ttaatcagag atcagcgagg    360
tctcacgagt gagaaggcga gagcttgtcc aaacgagcat tttcgggcgt gtgaacaccc    420
atttcagcaa agccgtcgtt gtccagttca gcgaagcgca ttctgcggct ttggcgtgac    480
ccattctgct agctcagcac tgagaatacg cgtccgctgc agcgttggcg tacaggccgg    540
actacattag ccaacgcgta tcggcagtgg caaacctctt cgcttctaac tccgctgggc    600
caccagcttt gaccgccgcc tcccttcccc tccgctactg ctcctcccca ccccactccc    660
ccgcaggagc ggcggcggcg gcggcgaggt cgtaccccac atcggcgagc ggcggcggca    720
ccgccggagg caaaggcaag tctagaac                                       748
```

<210> SEQ ID NO 5
<211> LENGTH: 3234
<212> TYPE: DNA
<213> ORGANISM: Zea mays

<400> SEQUENCE: 5

| | | | | | |
|---|---|---|---|---|---|
| atggagggcg | acgcggacgg | cgtgaagtcg | gggaggcgcg | gtggcggaca | ggtgtgccag | 60 |
| atctgcggcg | acggcgtggg | caccacggcg | gaggggacg | tcttcgccgc | ctgcgacgtc | 120 |
| tgcgggtttc | cggtgtgccg | ccctgctac | gagtacgagc | gcaaggacgg | cacgcaggcg | 180 |
| tgcccccagt | gcaagaccaa | gtacaagcgc | cacaagggga | gcccggcgat | ccgtggggag | 240 |
| gaaggagacg | acactgatgc | cgatagcgac | ttcaattacc | ttgcatctgg | caatgaggac | 300 |
| cagaagcaga | agattgccga | cagaatgcgc | agctggcgca | tgaacgttgg | gggcagcggg | 360 |
| gatgttggtc | gccccaagta | tgacagtggc | gagatcgggc | ttaccaagta | tgacagtggc | 420 |
| gagattcctc | gggatacat | cccatcagtc | actaacagcc | agatctcagg | agaaatccct | 480 |
| ggtgcttccc | ctgaccatca | tatgatgtcc | ccaactggga | acattggcaa | gcgtgctcca | 540 |
| tttccctatg | tgaaccattc | gccaaatccg | tcaagggagt | tctctggtag | cattgggaat | 600 |
| gttgctggaa | agagagggt | tgatggctgg | aaaatgaagc | aggacaaggg | gacgattccc | 660 |
| atgacgaatg | gcacaagcat | tgctccctct | gagggtcggg | gtgttggtga | tattgatgca | 720 |
| tcaactgatt | acaacatgga | agatgcctta | ttgaacgacg | aaactcgaca | gcctctatct | 780 |
| aggaaagttc | cacttccttc | ctccaggata | aatccataca | ggatggtcat | tgtgctgcga | 840 |
| ttgattgttc | taagcatctt | cttgcactac | cgtatcacaa | atcctgtgcg | caatgcatac | 900 |
| ccattatggc | ttctatctgt | tatatgtgag | atctggtttg | ctctttcgtg | gatattggat | 960 |
| cagttcccta | gtggtttcc | aatcaaccgg | gagacgtacc | ttgataggct | ggcattaagg | 1020 |
| tatgaccggg | aaggtgagcc | atctcagttg | gctgctgttg | acattttcgt | cagtacagtc | 1080 |
| gacccaatga | aggagcctcc | tcttgtcact | gccataccg | tgctatccat | tcttgctgtg | 1140 |
| gattaccctg | tggataaggt | ctcttgctat | gtatctgatg | atggagctgc | gatgctgaca | 1200 |
| tttgatgcac | tagctgagac | ttcagagttt | gctagaaaat | gggtaccatt | tgttaagaag | 1260 |
| tacaacattg | aacctagagc | tcctgaatgg | tacttctccc | agaaaattga | ttacttgaag | 1320 |
| gacaaagtgc | acccttcatt | tgttaaagac | cgccgggcca | tgaagagaga | atatgaagaa | 1380 |
| ttcaaagtta | gggtaaatgg | ccttgttgct | aaggcacaga | aagttcctga | ggaaggatgg | 1440 |
| atcatgcaag | atggcacacc | atggccagga | acaataccm | gggaccatcc | tggaatgatt | 1500 |
| caggttttcc | ttggtcacag | tggtggcctt | gatactgagg | gcaatgagct | accccgtttg | 1560 |
| gtctatgttt | ctcgtgaaaa | gcgtcctgga | ttccagcatc | acaagaaagc | tggtgccatg | 1620 |
| aatgctcttg | ttcgtgtctc | agctgtgctt | accaatggac | aatacatgtt | gaatcttgat | 1680 |
| tgtgatcact | acattaacaa | cagtaaggct | ctcagggaag | ctatgtgctt | ccttatggac | 1740 |
| cctaacctag | gaaggagtgt | ctgctacgtc | cagtttcccc | agagattcga | tggcattgac | 1800 |
| aggaatgatc | gatatgccaa | caggaacacc | gtgttttccg | atattaactt | gagaggtctt | 1860 |
| gatggcatcc | aaggaccagt | ttatgtcgga | actggctgtg | ttttcaaccg | aacagctcta | 1920 |
| tatggttatg | agcccccaat | taagcagaag | aagggtggtt | tcttgtcatc | actatgtggc | 1980 |
| ggtaggaaga | aggcaagcaa | atcaaagaag | ggctcggaca | agaagaagtc | gcagaagcat | 2040 |
| gtggacagtt | ctgtgccagt | attcaacctt | gaagatatag | aggagggagt | tgaaggcgct | 2100 |
| ggatttgacg | acgagaaatc | acttcttatg | tctcaaatga | gcctggagaa | gagatttggc | 2160 |

| | |
|---|---|
| cagtccgcag cgtttgttgc ctccactctg atggagtatg gtggtgttcc tcagtccgca | 2220 |
| actccggagt ctcttctgaa agaagctatc catgttataa gctgtggcta tgaggacaag | 2280 |
| actgaatggg gaactgagat cgggtggatc tacggttctg tgacagaaga cattctcacc | 2340 |
| ggattcaaga tgcacgcgcg aggctggcgg tcgatctact gcatgcccaa gcggccagct | 2400 |
| ttcaagggt ctgcccccat caatctttcg accgtctga accaggtgct ccggtgggct | 2460 |
| cttgggtccg tggagatcct cttcagccgg cactgccccc tgtggtacgg ctacggaggg | 2520 |
| cggctcaagt tcctggagag attcgcgtac atcaacacca ccatctaccc gctcacgtcc | 2580 |
| atcccgcttc tcatctactg catcctgccc gccatctgtc tgctcaccgg aaagttcatc | 2640 |
| attccagaga tcagcaactt cgccagcatc tggttcatct ccctcttcat ctcgatcttc | 2700 |
| gccacgggca tcctggagat gaggtggagc ggggtgggca tcgacgagtg gtggaggaac | 2760 |
| gagcagttct gggtgatcgg gggcatctcc gcgcacctct tcgccgtgtt ccagggcctg | 2820 |
| ctcaaggtgc tggccggcat cgacaccaac ttcaccgtca cctccaaggc ctcggacgag | 2880 |
| gacggcgact tcgcggagct gtacatgttc aagtggacga cgctcctgat cccgcccacc | 2940 |
| accatcctga tcatcaacct ggtcggcgtc gtcgccggca tctcctacgc catcaacagc | 3000 |
| ggataccagt cgtggggccc gctcttcggc aagctcttct tcgccttctg ggtcatcgtc | 3060 |
| cacctgtacc cgttcctcaa gggcctcatg ggcaggcaga accgcacccc gaccatcgtc | 3120 |
| gtcgtctggg ccatcctgct ggcgtccatc ttctccttgc tgtgggttcg catcgacccc | 3180 |
| ttcaccaccc gcgtcactgg cccggatacc cagacgtgtg gcatcaactg ctag | 3234 |

<210> SEQ ID NO 6
<211> LENGTH: 1578
<212> TYPE: DNA
<213> ORGANISM: Zea mays

<400> SEQUENCE: 6

| | |
|---|---|
| atgctgtccg agctcaacgc gccccagcg ccgctcccgc ccgcgacgcc ggccccaagg | 60 |
| ctcgcgtcca tcgtccac cgtcacaagt ggcgccgccg ccggtgctgg ctacttcgat | 120 |
| ctcccgcccg ccgtggactc gtccagcagt acctacgctc tgaagccgat ccctcgccg | 180 |
| gtggcggcgc cgtcggccga cccgtccacg gactcggcgc gggagcccaa gcgaatgagg | 240 |
| actggcggcg gcagcacgtc ctcctcctct tcctcgtcgt catccatgga tggcggtcgc | 300 |
| actaggagct ccgtggtcga agctgcgccg ccggcgacgc aagcatccgc agcggccaac | 360 |
| gggcccgcgg tgccggtggt ggtggtggac acgcaggagg ccgggatccg gctcgtgcac | 420 |
| gcgctgctgg cgtgcgcgga ggccgtgcag caggagaact ctctgcggc ggaggcgctg | 480 |
| gtcaagcaga tccccatgct ggcctcgtcg cagggcggtg ccatgcgcaa ggtcgccgcc | 540 |
| tacttcggcg aggcgcttgc ccgccgcgtg tatcgcttcc gcccaccacc ggacagctcc | 600 |
| ctcctcgacg ccgccttcgc cgacctctta cacgcgcact tctacgagtc ctgcccctac | 660 |
| ctgaagttcg cccacttcac cgcgaaccag gccatcctcg aggccttcgc cggctgccgc | 720 |
| cgcgtccacg tcgtcgactt cggcatcaag caggggatgc agtggccggc tcttctccag | 780 |
| gccctcgccc tccgccctgg cggccccccg tcgttccggc tcaccggcgt cgggccgccg | 840 |
| cagcccgacg agaccgacgc cttgcagcag gtgggctgga acttgccca gttcgcgcac | 900 |
| actatccgcg tggacttcca gtaccgtggc ctcgtcgcgg ccacgctcgc cgacctggag | 960 |
| ccgttcatgc tgcaaccgga gggcgatgac acggatgacg agcccgaggt gatcgccgtg | 1020 |
| aactccgtgt tcgagctgca ccggcttctt gcgcagcccg gtgcactcga aaggtcctg | 1080 |

```
ggcacggtgc gcgcggtgcg gccgaggatc gtgaccgtgg tcgagcagga ggccaaccac    1140
aactccggca cgttcctcga ccgcttcacc gagtcgctgc actactactc caccatgttc    1200
gattctctcg agggcgccgg cgccggctcc ggccagtcca ccgacgcctc cccggccgcg    1260
gccggcggca cggaccaggt catgtcggag gtgtacctcg gccggcagat ctgcaacgtg    1320
gtggcgtgcg agggcgcgga gcgcacggaa cgccacgaga cgctggggca gtggcgcagc    1380
cgcctcggcg gctccgggtt cgcgcccgtg cacctgggct ccaatgccta caagcaggcg    1440
agcacgctgc tggcgctctt cgccggcggc gacgggtaca gggtggagga aaggacggg     1500 tgcctgaccc tggggtggca tacgcgcccg ctcatcgcca cctcggcgtg gcgcgtcgcc    1560
gccgccgccg ctccgtga                                                  1578

<210> SEQ ID NO 7
<211> LENGTH: 825
<212> TYPE: DNA
<213> ORGANISM: Zea mays

<400> SEQUENCE: 7
aaatccttac agaattgctg tagtttcata gtgctagatg tggacagcaa agcgccgctg      60
tatgcttctg cttttctttt ttggtgtgtg tagccacatc ctttgttcct gcccggcgcc     120
atcccacttg gttgttttt tttatgattg aaagccttca tgcttcctcg gtcaatcacc     180
ggtgcgcact gggagcatcg ccggaaaaaa aattcttcgg ctaagagtaa cttcttctc     240 cttttcttct ctgatctcgc gagcagtgct gataacgtgt tgtaatctac ttagcggtaa     300
cgagattgag agagacaaaa tgacagaact attgtcttta ttgcagagtg tcatgtattt     360
atacagggga tacaaagtct cccaaggggt gtgtcccttg ggagtaactg ccagttgatc     420
acaggacaat attttgtaac aaaacgtaca catcgtcaaa atagcgaggc atgaaactgg     480
ccttggccat ggacgcgtga agcgcgccat gcgttggata tgtggtcaat aagtatatac     540
aatacaatgt ttaacagagc tgatagtact gctttggcac atttttgtcc acgcttcatg     600
agagataaaa cacctgcacg taaattcaca tgctgcactg aaggcccgat cactgaggag     660
cgaactgccg taactccctt ctatatatac ccccagtccc tgtttcagtt ttcgtcaagc     720
tagcagcacc aagttgtcga tcacttgcct gctcttgagc tcgattaagc tatcatcagc     780
tacagcatcc gatcccaaac tgcaactgta gcagcgacaa ctgcc                     825

<210> SEQ ID NO 8
<211> LENGTH: 162
<212> TYPE: DNA
<213> ORGANISM: Zea mays

<400> SEQUENCE: 8
actgccgtaa ctcccttcta tatacccc cagtccctgt ttcagttttc gtcaagctag       60
cagcaccaag ttgtcgatca cttgcctgct cttgagctcg attaagctat catcagctac     120
agcatccgat cccaaactgc aactgtagca gcgacaactg cc                        162

<210> SEQ ID NO 9
<211> LENGTH: 273
<212> TYPE: DNA
<213> ORGANISM: Zea mays

<400> SEQUENCE: 9
atgctcgtgc acgcgctgct ggcgtgcgcg gaggccgtgc agcaggagaa cttctctgcg      60
gcggaggcgc tggtcaagca gatccccatg ctggcctcgt cgcagggcgg tgccatgcgc     120
```

```
aaggtcgccg cctacttcgg cgaggcgctt gcccgccgcg tgtatcgctt ccgcccgcca    180
ccggacagct ccctcctcga cgccgccttc gccgacctct tgcacgcgca cttctacgag    240
tcctgcccct acctgaagtt cgcccacttc tag                                 273

<210> SEQ ID NO 10
<211> LENGTH: 277
<212> TYPE: DNA
<213> ORGANISM: Zea mays

<400> SEQUENCE: 10
ctaaagaagg agtgcgtcga agcagatcgt tcaaacattt ggcaataaag tttcttaaga     60
ttgaatcctg ttgccggtct tgcgatgatt atcatataat ttctgttgaa ttacgttaag    120
catgtaataa ttaacatgta atgcatgacg ttatttatga gatgggtttt tatgattaga    180
gtcccgcaat tatacattta atacgcgata gaaaacaaaa tatagcgcgc aaactaggat    240
aaattatcgc gcgcggtgtc atctatgtta ctagatc                             277

<210> SEQ ID NO 11
<211> LENGTH: 738
<212> TYPE: DNA
<213> ORGANISM: Zea mays

<400> SEQUENCE: 11
atggggcgcg ggaaggtgca gctgaagcgg atcgagaaca agatcaaccg ccaggtgaca     60
ttctccaagc gccgctcggg gctactcaag aaggcgcacg agatctccgt gctctgcgac    120
gccgaggtcg cgctcatcat cttctccacc aagggcaagc tctacgagta ctctaccgat    180
tcatgtatgg acaaaattct tgaacggtat gagcgctact cctatgcaga aaaggttctc    240
atttccgcag aatatgaaac tcagggcaat tggtgccatg aatatagaaa actaaaggcg    300
aaggtcgaga caatacagaa atgtcaaaag cacctcatgg gagaggatct tgaaactttg    360
aatctcaaag agcttcagca actagagcag cagctggaga gttcactgaa acatatcaga    420
acaaggaaga gccagcttat ggtcgagtca atttcagcgc tccaacggaa ggagaagtca    480
ctgcaggagg agaacaaggt tctgcagaag gagctcgcgg agaagcagaa agaccagcgg    540
cagcaagtgc aacgggacca aactcaacag cagaccagtt cgtcttccac gtccttcatg    600
ttaagggaag ctgccccaac aacaaatgtc agcatcttcc ctgtggcagc aggcgggagg    660
gtggtggaag gggcagcagc gcagccgcag gctcgcgttg gactgccacc atggatgctt    720
agccatctga gctgctga                                                  738

<210> SEQ ID NO 12
<211> LENGTH: 1554
<212> TYPE: DNA
<213> ORGANISM: Glycine max

<400> SEQUENCE: 12
atgaagaggg aacgcgagca gcttggttcc atcgcaggga cctcaagctg cggttattca     60
agcggaaaat cgaatctttg ggaggaagaa ggaggcatgg acgagcttct tgcggtggtg    120
ggttacaagg ttaggtcatc ggacatggcg gaagtggcgc agaagcttga gcgtctcgaa    180
gaagccatgg gaaatgtcca agatgacctc ccggagattt caaacgacgt cgttcattac    240
aacccttccg acatctccaa ctggctcgaa accatgcttt ctaattttga ccctctcccc    300
tccgaagagc cggaaaagga ctccgcctcg tcggactacg atcttaaggc tattccgggg    360
aaagcaattt atggagctag cgacgcgcta ccaaacccta gcgcgtgaa agccgacgag    420
```

```
tcaaggcgcg cggtggtggt cgttgactcg caggagaacg ggatccgcct cgtgcacagc    480
ctcatggcgt gcgcggaggc cgtggagaac aacaacctcg ccgtggcgga ggcgctggtg    540
aagcagatcg gcttcctcgc tgtgtcgcag gttggagcta tgaggaaagt cgcaatctac    600
ttcgccgaag cgctcgcgag gcgaatctac agagtcttcc ctctgcaaca ctctctctcc    660
gattctcttc agattcactt ctacgaaacc tgtccatacc tcaagttcgc acacttcacc    720
gcgaaccagg ttatcctcga agcgttccaa ggaaagaacc gcgttcacgt gattgatttc    780
ggtatcaacc aggggatgca gtggccggcg ctgatgcaag ccctagcggt tcgcaccggc    840
ggtcctccgg ttttccgact caccggaatc gggccgccgg cggcggacaa ctccgaccac    900
ctccaggagg tagggtggaa gctcgcgcag ctggcggagg agatcaacgt gcagttcgag    960
taccgtggct tcgtcgcgaa cagcctcgcc gatctcgacg cctccatgct cgatctccgg   1020
gaaggcgaag ccgtcgctgt gaactctgtc ttcgagtttc acaagctcct cgcccgcccc   1080
ggcgcggtgg agaaagtact ctccgtcgta cggcagattc ggccggagat tgtcaccgtc   1140
gtcgagcaag aagcgaacca caacagactg agttttgtcg accggttcac ggagtcactg   1200
cactattatt caaccctatt cgactcgctg gagggttcgc ctgtgaaccc taacgataag   1260
gccatgtcgg aggtttactt agggaagcaa atctgcaacg tggtggcgtg cgagggaatg   1320
gaccgcgtgg aaaggcacga gacgctgaac cagtggcgga accggttcgt ttcgaccgga   1380
ttttcttcgg ttcacttggg ttcgaacgcg tacaagcagg ccagcatgtt gctcgcgctt   1440
tttgcgggtg gggatgggta tagggtggaa gagaacaatg gttgtctcat gttgggatgg   1500
cacactaggc ccttgattgc cacctccgcg tggcaactcg ctgcaactcg ctga         1554
```

<210> SEQ ID NO 13
<211> LENGTH: 4215
<212> TYPE: DNA
<213> ORGANISM: Zea mays

<400> SEQUENCE: 13

```
gatccctgtg gagaaatttt tacgtcgcgg ggatggtatg gggagttatt cccctgtagg     60
aaatgggtga cgcctaagag ggagggtgaa gtaggacttc taaaactttc actaaactag    120
gccacaaata attccctaga gcaaaaccta tgcaaatagt caaactagaa tgtgcaaacc    180
aagttttgtc taagtgttgc tatctctacc gcaatggcta agtttcaatc tacactatat    240
aagtatgaat acaagaatga aacttaaata cttaatataa atgcggaaac ttaaagagca    300
aggtagagat gcaaattctc gtggatgacg cctgcatttt tatcgaggta tccggaacca    360
cgcaaggtcc cgactaatcc tcattggtgc ccctacgcaa agggaagccc acgcgagggc    420
caagcacctc ggtcgagtaa ctctatagag agccgtgggc cttctccacg cgcaagtggt    480
gctctgcttt cagctcctct cagaccctcc ccgctgtctc cactatcgag cttccggctg    540
aaaatgccat gggcctcgtt ccctccggta cacggtggcg gccgtgacac aaatgcggtt    600
atcacggtct cgcaagactc tcaccccccac ttggtacaat tcaatggct cgcacaagag    660 ccgaggggtt gatggtttat ctaatctcac tcaactaact aggattcatc taaagcaagc    720
gctagagcgg tctaactaac ctaagcactt cacaaagcac ctacgctaat caccgagtga    780
ttctatttag cacttgggtg caagagcact tgagaatgtc tactatatgc cttgctatgt    840
ctcttgggct cccaaacttg gaaatggccg gttggtggtg tatttatagc ccccaacaca    900
aaactagccg ttggaggaag ctgctgcttt ttgtggtgca ccggacagtc cggtggggtc    960
accagacagt ccgacgcccc tgtccggtgc ccctgtccga tgcgcctagt tgttgggtct   1020
```

```
gtcagcgtag gtgaccgttg gcgcgcaggc ttttttgcacc ggacagtccg gtggtcttcc   1080
ctcgacagtg ccacctggag ctagccgtta gggctactgt tcctggtgca ccggacagta   1140
gtccggtgct cttgtctgga cagtccgact gtggcaacac ttcttctttt cttggacttt   1200
acttgatctt catgatgtct tcttttgagg tgttgctttc ctaagtgcct tggtccaagt   1260
aacttatcat cctgtgaact acaaacacaa atagtagcaa acacattagt ccacaggtta   1320
tgttgatcat caaataccaa aatctattaa gccaaatggc ccagggtcca ttttccttac   1380
atccccgacg aagaattctc cgttgccatc cctatctgtg tacgcactac tggaatccgg   1440
gtctttgctg agtaccgcac tcggcaaagt cctactctcg gtaacgatgc cttttgccga   1500
gagcaggact ctcggcacag aatacactc ggcgaagggc gggtctcggc aaaggccgtt   1560
agccaccgtc caaagctgac ggtcgttacc tatgccgagt ggtggaaaga tattgtgaag   1620
gcctaaggcc gatttcgtcc taagcagggc ccaaaggaag gaagtacttc agtggatcaa   1680
gatgttgatg ttccctgatg ggtatgcagc taacctgagt aggtggggtg aacttatcta   1740
ctctgtgagt cttagggatg aagagtcatg acttccacat atggattgaa cagattcttc   1800
tctgtgcatg gacaatctgg ggcggcatcc aacaaccctc atggatcgcc cggccaatcg   1860
ccgcaccagt ccatccgccc acctcgatga gacttatgtt cttagtgttg agacttcaga   1920
acttattgat aatgctgtat tggatactta tgtttgtgtt cgatacttat gtgagaactt   1980
gagacttatg agacttatgt tcttgatact tatgtttgtg ttgagaactt ggatatttat   2040
gtttgtgttg gatacttatg tctgtgatga tatatgtgat gtatatatgt gatgtatatg   2100
tgacatatgt gatgtatatg tggtatcttt tgtttgtttg gatggaatag agaaagcaaa   2160
taaaaatgtg tatactggtc actttgtcga gtgtaacact cggcaaaaag gtgctttgcc   2220
gagtgttagg gccatagcac tcggtagaga accaatactt aggcaccggt aaagcttttt   2280
tgccgagtgt tgtggccctg gcactcagct ttgccgagtg cctcacagag cactcgacaa   2340
agaacctgac aaatggaccc gctggtaaat ccttttaccga gtgcaggtca gtagacactc   2400
ggcaaaggta acttctttgc cgagtgccgc ttagaacatt tgacaaaggg tcatctccgt   2460
tacccggtgt cgtgacggcc gcttttcttt gccgagtgcc tgatagaaag tactcggcaa   2520
agaagtcgtt gccaatgtat tgttcgctga ggtctctttg tcaagtatta cactcggcaa   2580
agactgtgcc gagtgttttt cagactttgc cgagtggttt aagcactcag caaagcgctc   2640
gatttcggta gtgacggttg tttggcaata gtaaaatcca gccctctccc gtggggaaaa   2700
aactggtagg atctggctcg tggctaagat tctctttctt ccctttgtaa aaaaagagaa   2760
gaaaaaaaaa acgactgtca cggtgccttg tctggtaatg atcgcgcggt cggctctgtc   2820
ctaacccgta agatggacgg gagctgatga tagcgtgacc tccaaataaa caacaagggc   2880
gtgttccccg tggtcgaata tttttaagggc cactgattag gtgcggttga atacatcaac   2940
ttcacgaaca tcatctgatc tgatctgatt tggtctgata tgatctgggt agtcatttct   3000
gcaatgagca tctatcaggt gaaccaatta atattgatga cattatgagt tcgaagatat   3060
actctaaagt gttatctaaa tacagaagac attcgttcgt tctttgccta taactctaaa   3120
aggcttgtaa caccctcatt catcctctat atacgaagac tctctcctat cattttatc    3180
gatttatttt ttttatattt tagacaatgg aattaaatag aactaaaata tatataagaa   3240
tctgaggacc cgagatggta atggggactc gatcctcgat tctccacgga gaattcctct   3300
aggatatagg taatttgtcc ccacgaggat tgaaacgggg taatttggtc cccatgtgcc   3360
cgtcccgcga acttctcttg atctaaatta gtctatttcc atgttaaaac tatactaaaa   3420
```

```
atttaataca cagtctatta taaaatagca aactaaattc taaagttgat gcatcttgta    3480
attttaaatc tggtttgttc aagttatatt catttgatat aataaatttg aatttgactc    3540
ttaatatcgt atttttttcct aacggggacg gattctccac ggggataaat tccatgatac   3600
agatgggatg aaagaaaaat ctcccgtatg aacttttgca ggaatgggga tgggccagag    3660
aaattttctc cctgcgggga cggggagcc atatcctcgg tggagaattt cccattatca     3720
tccttatttg tggtacatat atatgcataa tctttttttt ttgactgaca tgtgggaaag    3780
tatcccatct caatagtaga aaatcttggg aacggtagga tcgaacacaa agatcagcta    3840
gcttgtaatc accgagccat atagctagag ggtaatagat catgaatcaa atgtttttt    3900 cataaattat taaggctcta aattattttt aatttaaaaa taaataaaaa tatagttcga    3960
ttcttacatt ttatagtgta aaactttaaa gtctattatt accctactt attgagttat     4020 ggttcagttc ttgtcgacgg agagtaatga gatatagaat aaggtaccct atagaataaa    4080
gaatctttct ctgaaaagtc tgacgtacgt aaataagata taataaaaaa aatacaaaga    4140
gaagcgctgg actggagatg ctcctatatg cggcaatgcc tgtgcttata aatagccacc    4200
tcggtcggca aggac                                                    4215

<210> SEQ ID NO 14
<211> LENGTH: 538
<212> TYPE: DNA
<213> ORGANISM: Zea mays

<400> SEQUENCE: 14
gtccgccttg tttctcctct gtctcttgat ctgactaatc ttggtttatg attcgttgag      60
taattttggg gaaagcttcg tccacagttt ttttttcgat gaacagtgcc gcagtggcgc     120
tgatcttgta tgctatcctg caatcgtggt gaacttattt cttttatatc cttcactccc     180
atgaaaaggc tagtaatctt tctcgatgta acatcgtcca gcactgctat taccgtgtgg     240
tccatccgac agtctggctg aacacatcat acgatattga gcaaagatcg atctatcttc     300
cctgttcttt aatgaaagac gtcatttttca tcagtatgat ctaagaatgt tgcaacttgc    360
aaggaggcgt ttctttcttt gaatttaact aactcgttga gtggccctgt ttctcggacg     420
taaggccttt gctgctccac acatgtccat tcgaatttta ccgtgtttag caagggcgaa     480
aagtttgcat cttgatgatt tagcttgact atgcgattgc tttcctggac ccgtgcag      538

<210> SEQ ID NO 15
<211> LENGTH: 1377
<212> TYPE: DNA
<213> ORGANISM: Zea mays

<400> SEQUENCE: 15
aattcgccct tgtttaaact taatatttgt ttaaactttt tactaaattc atgtaataat      60
taatgtatgc gttatatata tatgtctagg tttataatta ttcatatgaa tatgaacata     120
aaaatctagg gctaaaacga ctactatttt gaaaacggaa ggagtagtaa gttatttaag    180
cggaggggaa ccatgatggg ctagtgattt aatttacata tatatattgg tgttctgggc    240
tcttacatga aagatctag ttaactgttg ttactgaaca gcgaagacaa atatataatt     300
taagctcccc aactgctagt gattctgtta agaggtaatg tttaaagtaa atttacaaga    360
gcccgtctag ctcagtcggt agagcgcaag gctcttaacc ttgtggtcgt gggttcgagc    420
cccacggtgg gcgcacaatt ttttgttttt tgacattttt tgtttgctta gttgcagacg    480 gttttttccccc tgctaggaga tttccgagag aaaaaaaagg cactacaggt taaccaaaac    540
```

```
caccaacctt tggagcgtcg aggcgacggg gcatttgcgt agttgaagct tacaaagttg      600
catatgagat gagtgccgga catgaagcgg ataacgtttt aaactggcaa caatatctag      660
ctgtttcaaa ttcaggcgtg ggaagctacg cctacgcgcc ctggacggcg tgtaaagagc      720
cagcatcggc atcattgtca aacgatcgac aaggccaaga aattccaaat atattattaa      780 taaaaagaa ggcaccaaat tagttttttgt tttttagtat gtgtggcgga ggaaattttg      840
agaacgaacg tatccaaaga aggcacaaga cgatatagat tgacgcggct agaaagttgc      900
agcaagacag tgggtacggt cttatatatc ctaataaata aaaataaaa ctatagtgtg      960 tcaaatgtca acaagaggag gaggcagcca aattagcaga gggagacaag tagagcacgc     1020
cttattagct tgcttattta tcgtggtggt gtacttgtta attactggca cgcattatca     1080
acaacgcagt tctggatgtg aatctagaca acatttgtc taggttccgc acgtatagtt      1140
tttttctttt tttttggggg gggggggga acggaagctg taataaacgg tactaggaac     1200
gaaagcaacc gccgcgcgca tgtttttgca atagattacg gtgaccttga tgcaccaccg     1260
cgtgctataa aaaccagtgt ccccgagtct actcatcaac caatccataa ctcgaaacct     1320
tttcttgtgc tctgttctgt ctgtgtgttt ccaaagcaag cgaaagaggt cgagggg        1377
```

<210> SEQ ID NO 16
<211> LENGTH: 1078
<212> TYPE: PRT
<213> ORGANISM: Zea mays

<400> SEQUENCE: 16

```
Met Asp Ala Gly Ser Val Thr Gly Gly Leu Ala Ala Gly Ser His Met
1               5                   10                  15

Arg Asp Glu Leu His Val Met Arg Ala Arg Glu Pro Asn Ala Lys
            20                  25                  30

Val Arg Ser Ala Asp Val Lys Thr Cys Arg Val Cys Ala Asp Glu Val
        35                  40                  45

Gly Thr Arg Glu Asp Gly Gln Pro Phe Val Ala Cys Ala Glu Cys Gly
    50                  55                  60

Phe Pro Val Cys Arg Pro Cys Tyr Glu Tyr Glu Arg Ser Glu Gly Thr
65                  70                  75                  80

Gln Cys Cys Pro Gln Cys Asn Thr Arg Tyr Lys Arg Gln Lys Gly Cys
                85                  90                  95

Pro Arg Val Glu Gly Asp Glu Glu Gly Pro Glu Met Asp Asp Phe
            100                 105                 110

Glu Asp Glu Phe Pro Ala Lys Ser Pro Lys Lys Pro His Glu Pro Val
        115                 120                 125

Ala Phe Asp Val Tyr Ser Glu Asn Gly Glu His Pro Ala Gln Lys Trp
    130                 135                 140

Arg Thr Gly Gly Gln Thr Leu Ser Ser Phe Thr Gly Ser Val Ala Gly
145                 150                 155                 160

Lys Asp Leu Glu Ala Glu Arg Glu Met Glu Gly Ser Met Glu Trp Lys
                165                 170                 175

Asp Arg Ile Asp Lys Trp Lys Thr Lys Gln Glu Lys Arg Gly Lys Leu
            180                 185                 190

Asn His Asp Asp Ser Asp Asp Asp Asp Lys Asn Glu Asp Glu Tyr
        195                 200                 205

Met Leu Leu Ala Glu Ala Arg Gln Pro Leu Trp Arg Lys Val Pro Ile
    210                 215                 220
```

```
Pro Ser Ser Met Ile Asn Pro Tyr Arg Ile Val Ile Val Leu Arg Leu
225                 230                 235                 240

Val Val Leu Cys Phe Phe Leu Lys Phe Arg Ile Thr Thr Pro Ala Thr
            245                 250                 255

Asp Ala Val Pro Leu Trp Leu Ala Ser Val Ile Cys Glu Leu Trp Phe
        260                 265                 270

Ala Phe Ser Trp Ile Leu Asp Gln Leu Pro Lys Trp Ala Pro Val Thr
    275                 280                 285

Arg Glu Thr Tyr Leu Asp Arg Leu Ala Leu Arg Tyr Asp Arg Glu Gly
290                 295                 300

Glu Ala Cys Arg Leu Ser Pro Ile Asp Phe Phe Val Ser Thr Val Asp
305             310                 315                 320

Pro Leu Lys Glu Pro Pro Ile Ile Thr Ala Asn Thr Val Leu Ser Ile
            325                 330                 335

Leu Ala Val Asp Tyr Pro Val Asp Arg Val Ser Cys Tyr Val Ser Asp
            340                 345                 350

Asp Gly Ala Ser Met Leu Leu Phe Asp Ala Leu Ser Glu Thr Ala Glu
            355                 360                 365

Phe Ala Arg Arg Trp Val Pro Phe Cys Lys Lys Phe Ala Val Glu Pro
370                 375                 380

Arg Ala Pro Glu Phe Tyr Phe Ser Gln Lys Ile Asp Tyr Leu Lys Asp
385                 390                 395                 400

Lys Val Gln Pro Thr Phe Val Lys Glu Arg Arg Ala Met Lys Arg Glu
                405                 410                 415

Tyr Glu Glu Phe Lys Val Arg Ile Asn Ala Leu Val Ala Lys Ala Gln
            420                 425                 430

Lys Lys Pro Glu Glu Gly Trp Val Met Gln Asp Gly Thr Pro Trp Pro
            435                 440                 445

Gly Asn Asn Thr Arg Asp His Pro Gly Met Ile Gln Val Tyr Leu Gly
450                 455                 460

Asn Gln Gly Ala Leu Asp Val Glu Gly His Glu Leu Pro Arg Leu Val
465                 470                 475                 480

Tyr Val Ser Arg Glu Lys Arg Pro Gly Tyr Asn His His Lys Lys Ala
            485                 490                 495

Gly Ala Met Asn Ala Leu Val Arg Val Ser Ala Val Leu Thr Asn Ala
            500                 505                 510

Pro Phe Ile Leu Asn Leu Asp Cys Asp His Tyr Val Asn Asn Ser Lys
            515                 520                 525

Ala Val Arg Glu Ala Met Cys Phe Leu Met Asp Pro Gln Leu Gly Lys
            530                 535                 540

Lys Leu Cys Tyr Val Gln Phe Pro Gln Arg Phe Asp Gly Ile Asp Arg
545                 550                 555                 560

His Asp Arg Tyr Ala Asn Arg Asn Val Val Phe Phe Asp Ile Asn Met
            565                 570                 575

Lys Gly Leu Asp Gly Ile Gln Gly Pro Val Tyr Val Gly Thr Gly Cys
            580                 585                 590

Val Phe Asn Arg Gln Ala Leu Tyr Gly Tyr Asp Pro Pro Arg Pro Glu
            595                 600                 605

Lys Arg Pro Lys Met Thr Cys Asp Cys Trp Pro Ser Trp Cys Cys Cys
610                 615                 620

Cys Cys Cys Phe Gly Gly Gly Lys Arg Gly Lys Ala Arg Lys Asp Lys
625                 630                 635                 640
```

```
Lys Gly Asp Gly Gly Glu Glu Pro Arg Arg Gly Leu Leu Gly Phe Tyr
            645                 650                 655

Arg Lys Arg Ser Lys Lys Asp Lys Leu Gly Gly Ser Val Ala Gly
        660                 665                 670

Ser Lys Lys Gly Gly Gly Leu Tyr Lys Lys His Gln Arg Ala Phe Glu
        675                 680                 685

Leu Glu Glu Ile Glu Glu Gly Leu Glu Gly Tyr Asp Glu Leu Glu Arg
    690                 695                 700

Ser Ser Leu Met Ser Gln Lys Ser Phe Glu Lys Arg Phe Gly Gln Ser
705                 710                 715                 720

Pro Val Phe Ile Ala Ser Thr Leu Val Glu Asp Gly Gly Leu Pro Gln
                725                 730                 735

Gly Ala Ala Ala Asp Pro Ala Ala Leu Ile Lys Glu Ala Ile His Val
                740                 745                 750

Ile Ser Cys Gly Tyr Glu Glu Lys Thr Glu Trp Gly Lys Glu Ile Gly
                755                 760                 765

Trp Ile Tyr Gly Ser Val Thr Glu Asp Ile Leu Thr Gly Phe Lys Met
770                 775                 780

His Cys Arg Gly Trp Lys Ser Val Tyr Cys Thr Pro Thr Arg Pro Ala
785                 790                 795                 800

Phe Lys Gly Ser Ala Pro Ile Asn Leu Ser Asp Arg Leu His Gln Val
                805                 810                 815

Leu Arg Trp Ala Leu Gly Ser Val Glu Ile Phe Met Ser Arg His Cys
                820                 825                 830

Pro Leu Arg Tyr Ala Tyr Gly Gly Arg Leu Lys Trp Leu Glu Arg Phe
                835                 840                 845

Ala Tyr Thr Asn Thr Ile Val Tyr Pro Phe Thr Ser Ile Pro Leu Leu
                850                 855                 860

Ala Tyr Cys Thr Ile Pro Ala Val Cys Leu Leu Thr Gly Lys Phe Ile
865                 870                 875                 880

Ile Pro Thr Leu Asn Asn Leu Ala Ser Ile Trp Phe Ile Ala Leu Phe
                885                 890                 895

Leu Ser Ile Ile Ala Thr Ser Val Leu Glu Leu Arg Trp Ser Gly Val
                900                 905                 910

Ser Ile Glu Asp Trp Trp Arg Asn Glu Gln Phe Trp Val Ile Gly Gly
                915                 920                 925

Val Ser Ala His Leu Phe Ala Val Phe Gln Gly Phe Leu Lys Val Leu
                930                 935                 940

Gly Gly Val Asp Thr Ser Phe Thr Val Thr Ser Lys Ala Ala Gly Asp
945                 950                 955                 960

Glu Ala Asp Ala Phe Gly Asp Leu Tyr Leu Phe Lys Trp Thr Thr Leu
                965                 970                 975

Leu Val Pro Pro Thr Thr Leu Ile Ile Ile Asn Met Val Gly Ile Val
                980                 985                 990

Ala Gly Val Ser Asp Ala Val Asn Asn Gly Tyr Gly Ser Trp Gly Pro
                995                 1000                1005

Leu Phe Gly Lys Leu Phe Phe Ser Phe Trp Val Ile Val His Leu Tyr
                1010                1015                1020

Pro Phe Leu Lys Gly Leu Met Gly Arg Gln Asn Arg Thr Pro Thr Ile
1025                1030                1035                1040

Val Val Leu Trp Ser Ile Leu Leu Ala Ser Ile Phe Ser Leu Val Trp
                1045                1050                1055
```

Val Arg Ile Asp Pro Phe Ile Pro Lys Ala Lys Gly Pro Ile Leu Lys
         1060                1065                1070

Pro Cys Gly Val Glu Cys
         1075

<210> SEQ ID NO 17
<211> LENGTH: 1077
<212> TYPE: PRT
<213> ORGANISM: Zea mays

<400> SEQUENCE: 17

Met Glu Gly Asp Ala Asp Gly Val Lys Ser Gly Arg Arg Gly Gly
 1               5                  10                  15

Gln Val Cys Gln Ile Cys Gly Asp Gly Val Gly Thr Thr Ala Glu Gly
            20                  25                  30

Asp Val Phe Ala Ala Cys Asp Val Cys Gly Phe Pro Val Cys Arg Pro
            35                  40                  45

Cys Tyr Glu Tyr Glu Arg Lys Asp Gly Thr Gln Ala Cys Pro Gln Cys
    50                  55                  60

Lys Thr Lys Tyr Lys Arg His Lys Gly Ser Pro Ala Ile Arg Gly Glu
65                  70                  75                  80

Glu Gly Asp Asp Thr Asp Ala Asp Ser Asp Phe Asn Tyr Leu Ala Ser
                85                  90                  95

Gly Asn Glu Asp Gln Lys Gln Lys Ile Ala Asp Arg Met Arg Ser Trp
            100                 105                 110

Arg Met Asn Val Gly Gly Ser Gly Asp Val Gly Arg Pro Lys Tyr Asp
        115                 120                 125

Ser Gly Glu Ile Gly Leu Thr Lys Tyr Asp Ser Gly Glu Ile Pro Arg
    130                 135                 140

Gly Tyr Ile Pro Ser Val Thr Asn Ser Gln Ile Ser Gly Glu Ile Pro
145                 150                 155                 160

Gly Ala Ser Pro Asp His His Met Met Ser Pro Thr Gly Asn Ile Gly
                165                 170                 175

Lys Arg Ala Pro Phe Pro Tyr Val Asn His Ser Pro Asn Pro Ser Arg
            180                 185                 190

Glu Phe Ser Gly Ser Ile Gly Asn Val Ala Trp Lys Glu Arg Val Asp
        195                 200                 205

Gly Trp Lys Met Lys Gln Asp Lys Gly Thr Ile Pro Met Thr Asn Gly
    210                 215                 220

Thr Ser Ile Ala Pro Ser Glu Gly Arg Gly Val Gly Asp Ile Asp Ala
225                 230                 235                 240

Ser Thr Asp Tyr Asn Met Glu Asp Ala Leu Leu Asn Asp Glu Thr Arg
                245                 250                 255

Gln Pro Leu Ser Arg Lys Val Pro Leu Pro Ser Ser Arg Ile Asn Pro
            260                 265                 270

Tyr Arg Met Val Ile Val Leu Arg Leu Ile Val Leu Ser Ile Phe Leu
        275                 280                 285

His Tyr Arg Ile Thr Asn Pro Val Arg Asn Ala Tyr Pro Leu Trp Leu
    290                 295                 300

Leu Ser Val Ile Cys Glu Ile Trp Phe Ala Leu Ser Trp Ile Leu Asp
305                 310                 315                 320

Gln Phe Pro Lys Trp Phe Pro Ile Asn Arg Glu Thr Tyr Leu Asp Arg
                325                 330                 335

Leu Ala Leu Arg Tyr Asp Arg Glu Gly Glu Pro Ser Gln Leu Ala Ala
            340                 345                 350

-continued

```
Val Asp Ile Phe Val Ser Thr Val Asp Pro Met Lys Glu Pro Pro Leu
        355                 360                 365

Val Thr Ala Asn Thr Val Leu Ser Ile Leu Ala Val Asp Tyr Pro Val
        370                 375                 380

Asp Lys Val Ser Cys Tyr Val Ser Asp Gly Ala Ala Met Leu Thr
385                 390                 395                 400

Phe Asp Ala Leu Ala Glu Thr Ser Glu Phe Ala Arg Lys Trp Val Pro
                405                 410                 415

Phe Val Lys Lys Tyr Asn Ile Glu Pro Arg Ala Pro Glu Trp Tyr Phe
            420                 425                 430

Ser Gln Lys Ile Asp Tyr Leu Lys Asp Lys Val His Pro Ser Phe Val
        435                 440                 445

Lys Asp Arg Arg Ala Met Lys Arg Glu Tyr Glu Glu Phe Lys Val Arg
    450                 455                 460

Val Asn Gly Leu Val Ala Lys Ala Gln Lys Val Pro Glu Glu Gly Trp
465                 470                 475                 480

Ile Met Gln Asp Gly Thr Pro Trp Pro Gly Asn Asn Thr Arg Asp His
                485                 490                 495

Pro Gly Met Ile Gln Val Phe Leu Gly His Ser Gly Gly Leu Asp Thr
                500                 505                 510

Glu Gly Asn Glu Leu Pro Arg Leu Val Tyr Val Ser Arg Glu Lys Arg
            515                 520                 525

Pro Gly Phe Gln His His Lys Lys Ala Gly Ala Met Asn Ala Leu Val
        530                 535                 540

Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
                580                 585                 590

Pro Gln Arg Phe Asp Gly Ile Asp Arg Asn Asp Arg Tyr Ala Asn Arg
            595                 600                 605

Asn Thr Val Phe Phe Asp Ile Asn Leu Arg Gly Leu Asp Gly Ile Gln
        610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Gly Gly Phe Leu Ser
                645                 650                 655

Ser Leu Cys Gly Gly Arg Lys Lys Ala Ser Lys Ser Lys Gly Ser
        660                 665                 670

Asp Lys Lys Lys Ser Gln Lys His Val Asp Ser Ser Val Pro Val Phe
            675                 680                 685

Asn Leu Glu Asp Ile Glu Glu Gly Val Glu Gly Ala Gly Phe Asp Asp
        690                 695                 700

Glu Lys Ser Leu Leu Met Ser Gln Met Ser Leu Glu Lys Arg Phe Gly
705                 710                 715                 720

Gln Ser Ala Ala Phe Val Ala Ser Thr Leu Met Glu Tyr Gly Gly Val
                725                 730                 735

Pro Gln Ser Ala Thr Pro Glu Ser Leu Leu Lys Glu Ala Ile His Val
            740                 745                 750

Ile Ser Cys Gly Tyr Glu Asp Lys Thr Glu Trp Gly Thr Glu Ile Gly
        755                 760                 765
```

Trp Ile Tyr Gly Ser Val Thr Glu Asp Ile Leu Thr Gly Phe Lys Met
770                 775                 780

His Ala Arg Gly Trp Arg Ser Ile Tyr Cys Met Pro Lys Arg Pro Ala
785                 790                 795                 800

Phe Lys Gly Ser Ala Pro Ile Asn Leu Ser Asp Arg Leu Asn Gln Val
            805                 810                 815

Leu Arg Trp Ala Leu Gly Ser Val Glu Ile Leu Phe Ser Arg His Cys
            820                 825                 830

Pro Leu Trp Tyr Gly Tyr Gly Gly Arg Leu Lys Phe Leu Glu Arg Phe
            835                 840                 845

Ala Tyr Ile Asn Thr Thr Ile Tyr Pro Leu Thr Ser Ile Pro Leu Leu
850                 855                 860

Ile Tyr Cys Ile Leu Pro Ala Ile Cys Leu Leu Thr Gly Lys Phe Ile
865                 870                 875                 880

Ile Pro Glu Ile Ser Asn Phe Ala Ser Ile Trp Phe Ile Ser Leu Phe
            885                 890                 895

Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
            915                 920                 925

Ile Ser Ala His Leu Phe Ala Val Phe Gln Gly Leu Leu Lys Val Leu
930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
            965                 970                 975

Ile Pro Pro Thr Thr Ile Leu Ile Ile Asn Leu Val Gly Val Val Ala
            980                 985                 990

Gly Ile Ser Tyr Ala Ile Asn Ser Gly Tyr Gln Ser Trp Gly Pro Leu
            995                 1000                1005

Phe Gly Lys Leu Phe Phe Ala Phe Trp Val Ile His Leu Tyr Pro
    1010                1015                1020

Phe Leu Lys Gly Leu Met Gly Arg Gln Asn Arg Thr Pro Thr Ile Val
1025                1030                1035                1040

Val Val Trp Ala Ile Leu Leu Ala Ser Ile Phe Ser Leu Leu Trp Val
            1045                1050                1055

Arg Ile Asp Pro Phe Thr Thr Arg Val Thr Gly Pro Asp Thr Gln Thr
            1060                1065                1070

Cys Gly Ile Asn Cys
        1075

<210> SEQ ID NO 18
<211> LENGTH: 525
<212> TYPE: PRT
<213> ORGANISM: Zea mays

<400> SEQUENCE: 18

Met Leu Ser Glu Leu Asn Ala Pro Ala Pro Leu Pro Pro Ala Thr
1               5                   10                  15

Pro Ala Pro Arg Leu Ala Ser Thr Ser Ser Thr Val Thr Ser Gly Ala
            20                  25                  30

Ala Ala Gly Ala Gly Tyr Phe Asp Leu Pro Pro Ala Val Asp Ser Ser
        35                  40                  45

Ser Ser Thr Tyr Ala Leu Lys Pro Ile Pro Ser Pro Val Ala Ala Pro
50                  55                  60

```
Ser Ala Asp Pro Ser Thr Asp Ser Ala Arg Glu Pro Lys Arg Met Arg
 65                  70                  75                  80

Thr Gly Gly Gly Ser Thr Ser Ser Ser Ser Ser Ser Ser Ser Ser Met
                 85                  90                  95

Asp Gly Gly Arg Thr Arg Ser Ser Val Val Glu Ala Ala Pro Pro Ala
            100                 105                 110

Thr Gln Ala Ser Ala Ala Ala Asn Gly Pro Ala Val Pro Val Val Val
        115                 120                 125

Val Asp Thr Gln Glu Ala Gly Ile Arg Leu Val His Ala Leu Leu Ala
130                 135                 140

Cys Ala Glu Ala Val Gln Gln Glu Asn Phe Ser Ala Ala Glu Ala Leu
145                 150                 155                 160

Val Lys Gln Ile Pro Met Leu Ala Ser Ser Gln Gly Gly Ala Met Arg
                165                 170                 175

Lys Val Ala Ala Tyr Phe Gly Glu Ala Leu Ala Arg Arg Val Tyr Arg
            180                 185                 190

Phe Arg Pro Pro Pro Asp Ser Ser Leu Leu Asp Ala Ala Phe Ala Asp
        195                 200                 205

Leu Leu His Ala His Phe Tyr Glu Ser Cys Pro Tyr Leu Lys Phe Ala
210                 215                 220

His Phe Thr Ala Asn Gln Ala Ile Leu Glu Ala Phe Ala Gly Cys Arg
225                 230                 235                 240

Arg Val His Val Val Asp Phe Gly Ile Lys Gln Gly Met Gln Trp Pro
                245                 250                 255

Ala Leu Leu Gln Ala Leu Ala Leu Arg Pro Gly Gly Pro Pro Ser Phe
            260                 265                 270

Arg Leu Thr Gly Val Gly Pro Pro Gln Pro Asp Glu Thr Asp Ala Leu
        275                 280                 285

Gln Gln Val Gly Trp Lys Leu Ala Gln Phe Ala His Thr Ile Arg Val
290                 295                 300

Asp Phe Gln Tyr Arg Gly Leu Val Ala Ala Thr Leu Ala Asp Leu Glu
305                 310                 315                 320

Pro Phe Met Leu Gln Pro Glu Gly Asp Thr Asp Asp Glu Pro Glu
                325                 330                 335

Val Ile Ala Val Asn Ser Val Phe Glu Leu His Arg Leu Leu Ala Gln
            340                 345                 350

Pro Gly Ala Leu Glu Lys Val Leu Gly Thr Val Arg Ala Val Arg Pro
        355                 360                 365

Arg Ile Val Thr Val Val Glu Gln Glu Ala Asn His Asn Ser Gly Thr
370                 375                 380

Phe Leu Asp Arg Phe Thr Glu Ser Leu His Tyr Tyr Ser Thr Met Phe
385                 390                 395                 400

Asp Ser Leu Glu Gly Ala Gly Ala Gly Ser Gly Gln Ser Thr Asp Ala
                405                 410                 415

Ser Pro Ala Ala Ala Gly Gly Thr Asp Gln Val Met Ser Glu Val Tyr
            420                 425                 430

Leu Gly Arg Gln Ile Cys Asn Val Val Ala Cys Glu Gly Ala Glu Arg
        435                 440                 445

Thr Glu Arg His Glu Thr Leu Gly Gln Trp Arg Ser Arg Leu Gly Gly
450                 455                 460

Ser Gly Phe Ala Pro Val His Leu Gly Ser Asn Ala Tyr Lys Gln Ala
465                 470                 475                 480
```

```
Ser Thr Leu Leu Ala Leu Phe Ala Gly Gly Asp Gly Tyr Arg Val Glu
            485                 490                 495

Glu Lys Asp Gly Cys Leu Thr Leu Gly Trp His Thr Arg Pro Leu Ile
        500                 505                 510

Ala Thr Ser Ala Trp Arg Val Ala Ala Ala Ala Pro
        515                 520             525

<210> SEQ ID NO 19
<211> LENGTH: 90
<212> TYPE: PRT
<213> ORGANISM: Zea mays

<400> SEQUENCE: 19

Met Leu Val His Ala Leu Leu Ala Cys Ala Glu Ala Val Gln Gln Glu
 1               5                  10                  15

Asn Phe Ser Ala Ala Glu Ala Leu Val Lys Gln Ile Pro Met Leu Ala
            20                  25                  30

Ser Ser Gln Gly Gly Ala Met Arg Lys Val Ala Ala Tyr Phe Gly Glu
        35                  40                  45

Ala Leu Ala Arg Arg Val Tyr Arg Phe Arg Pro Pro Pro Asp Ser Ser
    50                  55                  60

Leu Leu Asp Ala Ala Phe Ala Asp Leu Leu His Ala His Phe Tyr Glu
65                  70                  75                  80

Ser Cys Pro Tyr Leu Lys Phe Ala His Phe
                85                  90

<210> SEQ ID NO 20
<211> LENGTH: 245
<212> TYPE: PRT
<213> ORGANISM: Zea mays

<400> SEQUENCE: 20

Met Gly Arg Gly Lys Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ser Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Tyr Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Thr Leu Asn Leu Lys Glu Leu Gln Gln Leu
        115                 120                 125

Glu Gln Gln Leu Glu Ser Ser Leu Lys His Ile Arg Thr Arg Lys Ser
    130                 135                 140

Gln Leu Met Val Glu Ser Ile Ser Ala Leu Gln Arg Lys Glu Lys Ser
145                 150                 155                 160

Leu Gln Glu Glu Asn Lys Val Leu Gln Lys Glu Leu Ala Glu Lys Gln
                165                 170                 175

Lys Asp Gln Arg Gln Val Gln Arg Asp Gln Thr Gln Gln Gln Thr
            180                 185                 190
```

```
Ser Ser Ser Ser Thr Ser Phe Met Leu Arg Glu Ala Ala Pro Thr Thr
            195                 200                 205

Asn Val Ser Ile Phe Pro Val Ala Ala Gly Gly Arg Val Val Glu Gly
            210                 215                 220

Ala Ala Ala Gln Pro Gln Ala Arg Val Gly Leu Pro Pro Trp Met Leu
225                 230                 235                 240

Ser His Leu Ser Cys
            245

<210> SEQ ID NO 21
<211> LENGTH: 86
<212> TYPE: PRT
<213> ORGANISM: Glycine max

<400> SEQUENCE: 21

Gly Ile Arg Leu Val His Ser Leu Met Ala Cys Ala Glu Ala Val Glu
1               5                   10                  15

Asn Asn Asn Leu Ala Val Ala Glu Ala Leu Val Lys Gln Ile Gly Phe
            20                  25                  30

Leu Ala Val Ser Gln Val Gly Ala Met Arg Lys Val Ala Ile Tyr Phe
        35                  40                  45

Ala Glu Ala Leu Ala Arg Arg Ile Tyr Arg Val Phe Pro Leu Gln His
    50                  55                  60

Ser Leu Ser Asp Ser Leu Gln Ile His Phe Tyr Glu Thr Cys Pro Tyr
65                  70                  75                  80

Leu Lys Phe Ala His Phe
            85

<210> SEQ ID NO 22
<211> LENGTH: 517
<212> TYPE: PRT
<213> ORGANISM: Glycine max

<400> SEQUENCE: 22

Met Lys Arg Glu Arg Glu Gln Leu Gly Ser Ile Ala Gly Thr Ser Ser
1               5                   10                  15

Cys Gly Tyr Ser Ser Gly Lys Ser Asn Leu Trp Glu Glu Gly Gly Gly
            20                  25                  30

Met Asp Glu Leu Leu Ala Val Val Gly Tyr Lys Val Arg Ser Ser Asp
        35                  40                  45

Met Ala Glu Val Ala Gln Lys Leu Glu Arg Leu Glu Glu Ala Met Gly
    50                  55                  60

Asn Val Gln Asp Asp Leu Pro Glu Ile Ser Asn Asp Val Val His Tyr
65                  70                  75                  80

Asn Pro Ser Asp Ile Ser Asn Trp Leu Glu Thr Met Leu Ser Asn Phe
            85                  90                  95

Asp Pro Leu Pro Ser Glu Glu Pro Glu Lys Asp Ser Ala Ser Ser Asp
            100                 105                 110

Tyr Asp Leu Lys Ala Ile Pro Gly Lys Ala Ile Tyr Gly Ala Ser Asp
        115                 120                 125

Ala Leu Pro Asn Pro Lys Arg Val Lys Ala Asp Glu Ser Arg Arg Ala
    130                 135                 140

Val Val Val Val Asp Ser Gln Glu Asn Gly Ile Arg Leu Val His Ser
145                 150                 155                 160

Leu Met Ala Cys Ala Glu Ala Val Glu Asn Asn Asn Leu Ala Val Ala
            165                 170                 175
```

Glu Ala Leu Val Lys Gln Ile Gly Phe Leu Ala Val Ser Gln Val Gly
            180                 185                 190

Ala Met Arg Lys Val Ala Ile Tyr Phe Ala Glu Ala Leu Ala Arg Arg
        195                 200                 205

Ile Tyr Arg Val Phe Pro Leu Gln His Ser Leu Ser Asp Ser Leu Gln
        210                 215                 220

Ile His Phe Tyr Glu Thr Cys Pro Tyr Leu Lys Phe Ala His Phe Thr
225                 230                 235                 240

Ala Asn Gln Val Ile Leu Glu Ala Phe Gln Gly Lys Asn Arg Val His
                245                 250                 255

Val Ile Asp Phe Gly Ile Asn Gln Gly Met Gln Trp Pro Ala Leu Met
            260                 265                 270

Gln Ala Leu Ala Val Arg Thr Gly Gly Pro Pro Val Phe Arg Leu Thr
        275                 280                 285

Gly Ile Gly Pro Pro Ala Ala Asp Asn Ser Asp His Leu Gln Glu Val
        290                 295                 300

Gly Trp Lys Leu Ala Gln Leu Ala Glu Glu Ile Asn Val Gln Phe Glu
305                 310                 315                 320

Tyr Arg Gly Phe Val Ala Asn Ser Leu Ala Asp Leu Asp Ala Ser Met
                325                 330                 335

Leu Asp Leu Arg Glu Gly Glu Ala Val Ala Val Asn Ser Val Phe Glu
            340                 345                 350

Phe His Lys Leu Leu Ala Arg Pro Gly Ala Val Glu Lys Val Leu Ser
        355                 360                 365

Val Val Arg Gln Ile Arg Pro Glu Ile Val Thr Val Val Glu Gln Glu
        370                 375                 380

Ala Asn His Asn Arg Leu Ser Phe Val Asp Arg Phe Thr Glu Ser Leu
385                 390                 395                 400

His Tyr Tyr Ser Thr Leu Phe Asp Ser Leu Glu Gly Ser Pro Val Asn
                405                 410                 415

Pro Asn Asp Lys Ala Met Ser Glu Val Tyr Leu Gly Lys Gln Ile Cys
            420                 425                 430

Asn Val Val Ala Cys Glu Gly Met Asp Arg Val Glu Arg His Glu Thr
        435                 440                 445

Leu Asn Gln Trp Arg Asn Arg Phe Val Ser Thr Gly Phe Ser Ser Val
        450                 455                 460

His Leu Gly Ser Asn Ala Tyr Lys Gln Ala Ser Met Leu Leu Ala Leu
465                 470                 475                 480

Phe Ala Gly Gly Asp Gly Tyr Arg Val Glu Glu Asn Asn Gly Cys Leu
                485                 490                 495

Met Leu Gly Trp His Thr Arg Pro Leu Ile Ala Thr Ser Ala Trp Gln
            500                 505                 510

Leu Ala Ala Thr Arg
        515

<210> SEQ ID NO 23
<211> LENGTH: 523
<212> TYPE: PRT
<213> ORGANISM: Glycine max

<400> SEQUENCE: 23

Met Lys Arg Glu Arg Gln Gln Leu Gly Ser Asn Ala Gly Thr Ser Ser
1               5                   10                  15

Cys Gly Tyr Ser Ser Gly Lys Ser Asn Leu Trp Glu Glu Glu Gly Gly
            20                  25                  30

```
Met Asp Glu Leu Leu Ala Val Val Gly Tyr Lys Val Arg Ser Ser Asp
         35                  40                  45
Met Ala Glu Val Ala Gln Lys Leu Glu Arg Leu Glu Glu Ala Met Gly
 50                  55                  60
Asn Val Gln Asp Asp Leu Thr Asp Leu Ser Asn Asp Ala Val His Tyr
 65                  70                  75                  80
Asn Pro Ser Asp Ile Ser Asn Trp Leu Gln Thr Met Leu Ser Asn Phe
                 85                  90                  95
Asp Pro Leu Pro Ser Glu Pro Glu Lys Asp Ser Ala Ser Ser Asp
                100                 105                 110
Tyr Asp Leu Lys Ala Ile Pro Gly Lys Ala Ile Tyr Gly Gly Gly Ser
            115                 120                 125
Asp Ala Leu Pro Asn Pro Lys Arg Val Arg Thr Asp Glu Ser Thr Arg
130                 135                 140
Ala Val Val Val Asp Leu Gln Glu Asn Gly Ile Arg Leu Val His
145                 150                 155                 160
Ser Leu Met Ala Cys Ala Glu Ala Val Glu Asn Asn Asn Leu Ala Val
                165                 170                 175
Ala Glu Ala Leu Val Lys Gln Ile Gly Phe Leu Ala Leu Ser Gln Val
            180                 185                 190
Gly Ala Met Arg Lys Val Ala Thr Tyr Phe Ala Glu Ala Leu Ala Arg
            195                 200                 205
Arg Ile Tyr Arg Val Phe Pro Gln Gln His Ser Leu Ser Asp Ser Leu
            210                 215                 220
Gln Ile His Phe Tyr Glu Thr Cys Pro Tyr Leu Lys Phe Ala His Phe
225                 230                 235                 240
Thr Ala Asn Gln Ala Ile Leu Glu Ala Phe Gln Gly Lys Asn Arg Val
                245                 250                 255
His Val Ile Asp Phe Gly Ile Asn Gln Gly Met Gln Trp Pro Ala Leu
                260                 265                 270
Met Gln Ala Leu Ala Leu Arg Asn Asp Gly Pro Pro Val Phe Arg Leu
            275                 280                 285
Thr Gly Ile Gly Pro Pro Ala Ala Asp Asn Ser Asp His Leu Gln Glu
            290                 295                 300
Val Gly Trp Lys Leu Ala Gln Leu Ala Glu Arg Ile His Val Gln Phe
305                 310                 315                 320
Glu Tyr Arg Gly Phe Val Ala Asn Ser Leu Ala Asp Leu Asp Ala Ser
                325                 330                 335
Met Leu Asp Leu Arg Glu Asp Glu Ser Val Ala Val Asn Ser Val Phe
            340                 345                 350
Glu Phe His Lys Leu Leu Ala Arg Pro Gly Ala Val Glu Lys Val Leu
            355                 360                 365
Ser Val Val Arg Gln Ile Arg Pro Glu Ile Leu Thr Val Val Glu Gln
            370                 375                 380
Glu Ala Asn His Asn Gly Leu Ser Phe Val Asp Arg Phe Thr Glu Ser
385                 390                 395                 400
Leu His Tyr Tyr Ser Thr Leu Phe Asp Ser Leu Glu Gly Ser Pro Val
                405                 410                 415
Asn Pro Asn Asp Lys Ala Met Ser Glu Val Tyr Leu Gly Lys Gln Ile
            420                 425                 430
Cys Asn Val Val Ala Cys Glu Gly Met Asp Arg Val Glu Arg His Glu
            435                 440                 445
```

```
Thr Leu Asn Gln Trp Arg Asn Arg Phe Gly Ser Thr Gly Phe Ser Pro
    450                 455                 460
Val His Leu Gly Ser Asn Ala Tyr Lys Gln Ala Ser Met Leu Leu Ser
465                 470                 475                 480
Leu Phe Gly Gly Gly Asp Gly Tyr Arg Val Glu Asn Asn Gly Cys
                485                 490                 495
Leu Met Leu Gly Trp His Thr Arg Pro Leu Ile Ala Thr Ser Val Trp
            500                 505                 510
Gln Leu Ala Thr Lys Ser Val Val Ala Ala His
        515                 520
```

<210> SEQ ID NO 24
<211> LENGTH: 91
<212> TYPE: PRT
<213> ORGANISM: Glycine max

<400> SEQUENCE: 24

```
Asn Gly Ile Arg Leu Val His Ser Leu Met Ala Cys Ala Glu Ala Val
1               5                   10                  15
Glu Asn Asn Leu Ala Val Ala Glu Ala Leu Val Lys Gln Ile Gly
            20                  25                  30
Phe Leu Ala Leu Ser Gln Val Gly Ala Met Arg Lys Val Ala Thr Tyr
        35                  40                  45
Phe Ala Glu Ala Leu Ala Arg Arg Ile Tyr Arg Val Phe Pro Gln Gln
    50                  55                  60
His Ser Leu Ser Asp Ser Leu Gln Ile His Phe Tyr Glu Thr Cys Pro
65                  70                  75                  80
Tyr Leu Lys Phe Ala His Phe Thr Ala Asn Gln
                85                  90
```

<210> SEQ ID NO 25
<211> LENGTH: 517
<212> TYPE: PRT
<213> ORGANISM: Glycine max

<400> SEQUENCE: 25

```
Met Lys Arg Glu Arg Glu Gln Leu Gly Ser Ile Ala Gly Thr Ser Ser
1               5                   10                  15
Cys Gly Tyr Ser Ser Gly Lys Ser Asn Leu Trp Glu Glu Gly Gly
            20                  25                  30
Met Asp Glu Leu Leu Ala Val Val Gly Tyr Lys Val Arg Ser Ser Asp
        35                  40                  45
Met Ala Glu Val Ala Gln Lys Leu Glu Arg Leu Glu Glu Ala Met Gly
    50                  55                  60
Asn Val Gln Asp Asp Leu Pro Glu Ile Ser Asn Asp Val His Tyr
65                  70                  75                  80
Asn Pro Ser Asp Ile Ser Asn Trp Leu Glu Thr Met Leu Ser Asn Phe
                85                  90                  95
Asp Pro Leu Pro Ser Glu Pro Glu Lys Ser Ala Ser Ser Asp
            100                 105                 110
Tyr Asp Leu Lys Ala Ile Pro Gly Lys Ala Ile Tyr Gly Ala Ser Asp
        115                 120                 125
Ala Leu Pro Asn Pro Lys Arg Val Lys Ala Asp Glu Ser Arg Arg Ala
    130                 135                 140
```

-continued

```
Val Val Val Asp Ser Gln Glu Asn Gly Ile Arg Leu Val His Ser
145                 150                 155                 160

Leu Met Ala Cys Ala Glu Ala Val Glu Asn Asn Leu Ala Val Ala
            165                 170                 175

Glu Ala Leu Val Lys Gln Ile Gly Phe Leu Ala Val Ser Gln Val Gly
            180                 185                 190

Ala Met Arg Lys Val Ala Ile Tyr Phe Ala Glu Ala Leu Ala Arg Arg
            195                 200                 205

Ile Tyr Arg Val Phe Pro Leu Gln His Ser Leu Ser Asp Ser Leu Gln
210                 215                 220

Ile His Phe Tyr Glu Thr Cys Pro Tyr Leu Lys Phe Ala His Phe Thr
225                 230                 235                 240

Ala Asn Gln Val Ile Leu Glu Ala Phe Gln Gly Lys Asn Arg Val His
            245                 250                 255

Val Ile Asp Phe Gly Ile Asn Gln Gly Met Gln Trp Pro Ala Leu Met
            260                 265                 270

Gln Ala Leu Ala Val Arg Thr Gly Gly Pro Pro Val Phe Arg Leu Thr
            275                 280                 285

Gly Ile Gly Pro Pro Ala Ala Asp Asn Ser Asp His Leu Gln Glu Val
290                 295                 300

Gly Trp Lys Leu Ala Gln Leu Ala Glu Glu Ile Asn Val Gln Phe Glu
305                 310                 315                 320

Tyr Arg Gly Phe Val Ala Asn Ser Leu Ala Asp Leu Asp Ala Ser Met
            325                 330                 335

Leu Asp Leu Arg Glu Gly Glu Ala Val Ala Val Asn Ser Val Phe Glu
            340                 345                 350

Phe His Lys Leu Leu Ala Arg Pro Gly Ala Val Glu Lys Val Leu Ser
            355                 360                 365

Val Val Arg Gln Ile Arg Pro Glu Ile Val Thr Val Val Gln Gln Glu
            370                 375                 380

Ala Asn His Asn Arg Leu Ser Phe Val Asp Arg Phe Thr Glu Ser Leu
385                 390                 395                 400

His Tyr Tyr Ser Thr Leu Phe Asp Ser Leu Glu Gly Ser Pro Val Asn
            405                 410                 415

Pro Asn Asp Lys Ala Met Ser Glu Val Tyr Leu Gly Lys Gln Ile Cys
            420                 425                 430

Asn Val Val Ala Cys Glu Gly Met Asp Arg Val Glu Arg His Glu Thr
            435                 440                 445

Leu Asn Gln Trp Arg Asn Arg Phe Val Ser Thr Gly Phe Ser Ser Val
450                 455                 460

His Leu Gly Ser Asn Ala Tyr Lys Gln Ala Ser Met Leu Leu Ala Leu
465                 470                 475                 480

Phe Ala Gly Gly Asp Gly Tyr Arg Val Glu Glu Asn Asn Gly Cys Leu
            485                 490                 495

Met Leu Gly Trp His Thr Arg Pro Leu Ile Ala Thr Ser Ala Trp Gln
            500                 505                 510

Leu Ala Ala Thr Arg
            515

<210> SEQ ID NO 26
<211> LENGTH: 91
<212> TYPE: PRT
<213> ORGANISM: Glycine max
```

-continued

<400> SEQUENCE: 26

```
Asn Gly Ile Arg Leu Val His Ser Leu Met Ala Cys Ala Glu Ala Val
 1               5                  10                  15

Glu Asn Asn Asn Leu Ala Val Ala Glu Ala Leu Val Lys Gln Ile Gly
             20                  25                  30

Phe Leu Ala Val Ser Gln Val Gly Ala Met Arg Lys Val Ala Ile Tyr
         35                  40                  45

Phe Ala Glu Ala Leu Ala Arg Arg Ile Tyr Arg Val Phe Pro Leu Gln
     50                  55                  60

His Ser Leu Ser Asp Ser Leu Gln Ile His Phe Tyr Glu Thr Cys Pro
 65                  70                  75                  80

Tyr Leu Lys Phe Ala His Phe Thr Ala Asn Gln
                 85                  90
```

<210> SEQ ID NO 27
<211> LENGTH: 595
<212> TYPE: PRT
<213> ORGANISM: Glycine max

<400> SEQUENCE: 27

```
Met Lys Arg Asp His Lys Asp Ser Cys Gly Gly Gly Ala Ala Gly
 1               5                  10                  15

Gly Thr Val Lys Gly Glu Cys Ser Ser Met Gln Ser Asn Gly Lys Ala
             20                  25                  30

Lys Met Trp Glu Glu Glu Gln Gln Gln Gln Gln Gln Gln Gln Gln Gln
         35                  40                  45

Gln Gln Gln Gln Gly Met Asp Glu Leu Leu Ala Ala Leu Gly Tyr Lys
     50                  55                  60

Val Arg Ala Ser Asp Met Ala Asp Val Ala Gln Lys Leu Glu Gln Leu
 65                  70                  75                  80

Glu Met Val Met Gly Cys Ala Gln Glu Asp Gly Ile Ser His Leu Ala
                 85                  90                  95

Ser Asp Thr Val His Tyr Asp Pro Thr Asp Leu Tyr Ser Trp Val Gln
            100                 105                 110

Ser Met Leu Thr Glu Leu Asn Pro Glu Pro Asn Asn Asn Leu Asp Pro
        115                 120                 125

Ser Ser Phe Leu Ile Asp Asn Asn Asn Ile Ile Asn Ser Thr Ala
    130                 135                 140

Pro Val Phe Asn Asp Asp Ser Glu Tyr Asp Leu Arg Ala Ile Pro Gly
145                 150                 155                 160

Ile Ala Ala Tyr Pro Pro Leu Pro Gln Asp Asn His Leu Asp Glu
                165                 170                 175

Ile Glu Thr Ala Asn Asn Ile Asn Lys Arg Leu Lys Pro Ser Pro Ala
            180                 185                 190

Glu Ser Ala Asp Ser Ala Ala Ser Glu Pro Thr Arg His Val Val Leu
        195                 200                 205

Val Asp His Gln Glu Ala Gly Val Arg Leu Val His Thr Leu Leu Ala
    210                 215                 220

Cys Ala Glu Ala Val Gln Gln Glu Asn Leu Lys Leu Ala Asp Ala Leu
225                 230                 235                 240

Val Lys His Val Gly Ile Leu Ala Ala Ser Gln Ala Gly Ala Met Arg
                245                 250                 255

Lys Val Ala Ser Tyr Phe Ala Gln Ala Leu Ala Arg Arg Ile Tyr Gly
            260                 265                 270
```

```
Ile Phe Pro Glu Glu Thr Leu Asp Ser Ser Phe Ser Asp Val Leu His
            275                 280                 285

Met His Phe Tyr Glu Ser Cys Pro Tyr Leu Lys Phe Ala His Phe Thr
    290                 295                 300

Ala Asn Gln Ala Ile Leu Glu Ala Phe Ala Thr Ala Gly Lys Val His
305                 310                 315                 320

Val Ile Asp Phe Gly Leu Lys Gln Gly Met Gln Trp Pro Ala Leu Met
                325                 330                 335

Gln Ala Leu Ala Leu Arg Pro Gly Gly Pro Thr Phe Arg Leu Thr
                340                 345                 350

Gly Ile Gly Pro Pro Gln Pro Asp Asn Thr Asp Ala Leu Gln Gln Val
            355                 360                 365

Gly Leu Lys Leu Ala Gln Leu Ala Gln Ile Ile Gly Val Gln Phe Glu
        370                 375                 380

Phe Arg Gly Phe Val Cys Asn Ser Leu Ala Asp Leu Asp Pro Asn Met
385                 390                 395                 400

Leu Glu Ile Arg Pro Gly Glu Ala Val Ala Val Asn Ser Val Phe Glu
                405                 410                 415

Leu His Arg Met Leu Ala Arg Ser Gly Ser Val Asp Lys Val Leu Asp
            420                 425                 430

Thr Val Lys Lys Ile Asn Pro Gln Ile Val Thr Ile Val Glu Gln Glu
        435                 440                 445

Ala Asn His Asn Gly Pro Gly Phe Leu Asp Arg Phe Thr Glu Ala Leu
    450                 455                 460

His Tyr Tyr Ser Ser Leu Phe Asp Ser Leu Glu Gly Ser Ser Ser Ser
465                 470                 475                 480

Ser Thr Gly Leu Gly Ser Pro Ser Gln Asp Leu Leu Met Ser Glu Leu
                485                 490                 495

Tyr Leu Gly Arg Gln Ile Cys Asn Val Val Ala Tyr Glu Gly Pro Asp
            500                 505                 510

Arg Val Glu Arg His Glu Thr Leu Thr Gln Trp Arg Gly Arg Leu Asp
        515                 520                 525

Ser Ala Gly Phe Asp Pro Val His Leu Gly Ser Asn Ala Phe Lys Gln
530                 535                 540

Ala Ser Met Leu Leu Ala Leu Phe Ala Gly Gly Asp Gly Tyr Arg Val
545                 550                 555                 560

Glu Glu Asn Asn Gly Cys Leu Met Leu Gly Trp His Thr Arg Pro Leu
                565                 570                 575

Ile Ala Thr Ser Ala Trp Lys Leu Pro Ser Ser Ser Glu Ser Ser Gly
            580                 585                 590

Leu Thr Gln
    595

<210> SEQ ID NO 28
<211> LENGTH: 94
<212> TYPE: PRT
<213> ORGANISM: Glycine max

<400> SEQUENCE: 28

Ala Gly Val Arg Leu Val His Thr Leu Leu Ala Cys Ala Glu Ala Val
1               5                   10                  15

Gln Gln Glu Asn Leu Lys Leu Ala Asp Ala Leu Val Lys His Val Gly
            20                  25                  30

Ile Leu Ala Ala Ser Gln Ala Gly Ala Met Arg Lys Val Ala Ser Tyr
        35                  40                  45
```

```
Phe Ala Gln Ala Leu Ala Arg Arg Ile Tyr Gly Ile Phe Pro Glu Glu
    50                  55                  60

Thr Leu Asp Ser Ser Phe Ser Asp Val Leu His Met His Phe Tyr Glu
65                  70                  75                  80

Ser Cys Pro Tyr Leu Lys Phe Ala His Phe Thr Ala Asn Gln
                85                  90

<210> SEQ ID NO 29
<211> LENGTH: 584
<212> TYPE: PRT
<213> ORGANISM: Glycine max

<400> SEQUENCE: 29

Met Lys Arg Asp His Arg Asp Ser Cys Gly Gly Gly Gly Gly Gly Ser
1               5                   10                  15

Val Lys Gly Glu Cys Ser Ser Met Pro Ser Asn Gly Lys Ala Asn Met
                20                  25                  30

Trp Glu Glu Gln Gln Gln Gln Gln Gly Met Asp Glu Leu Leu Ala
            35                  40                  45

Ala Leu Gly Tyr Lys Val Arg Ala Ser Asp Met Ala Asp Val Ala Gln
    50                  55                  60

Lys Leu Glu Gln Leu Glu Met Val Met Gly Cys Ala Gln Glu Glu Gly
65                  70                  75                  80

Ile Ser His Leu Ala Ser Asp Thr Val His Tyr Asp Pro Thr Asp Leu
                85                  90                  95

Tyr Ser Trp Val Gln Thr Met Leu Thr Glu Leu Asn Pro Glu Pro Asn
            100                 105                 110

Asn Asn Asn Asn Ser Leu Leu Gly Pro Ser Ser Leu Leu Ile Asp Asn
            115                 120                 125

Asn Thr Ala Pro Val Phe Asn Asp Asp Ser Glu Tyr Asp Leu Arg Ala
    130                 135                 140

Ile Pro Gly Ile Ala Ala Tyr Pro Pro Pro Pro Gln Asp Asn Asn
145                 150                 155                 160

Asn Asn Asn Asn Asn Leu Asp Glu Ile Glu Thr Ala Asn Asn Ile Asn
                165                 170                 175

Lys Arg Leu Lys Pro Ser Pro Val Glu Ser Ala Asp Ser Ala Ser Glu
            180                 185                 190

Pro Thr Arg Thr Val Leu Leu Val Asp His Gln Glu Ala Gly Val Arg
        195                 200                 205

Leu Val His Thr Leu Leu Ala Cys Ala Glu Ala Val Gln Gln Glu Asn
    210                 215                 220

Leu Lys Leu Ala Asp Ala Leu Val Lys His Val Gly Ile Leu Ala Ala
225                 230                 235                 240

Ser Gln Ala Gly Ala Met Arg Lys Val Ala Ser Tyr Phe Ala Gln Ala
                245                 250                 255

Leu Ala Arg Arg Ile Tyr Gly Ile Phe Pro Glu Glu Thr Leu Asp Ser
            260                 265                 270

Ser Phe Ser Asp Val Leu His Met His Phe Tyr Glu Ser Cys Pro Tyr
        275                 280                 285

Leu Lys Phe Ala His Phe Thr Ala Asn Gln Ala Ile Leu Glu Ala Phe
    290                 295                 300

Ala Thr Ala Gly Arg Val His Val Ile Asp Phe Gly Leu Arg Gln Gly
305                 310                 315                 320

Met Gln Trp Pro Ala Leu Met Gln Ala Leu Ala Leu Arg Pro Gly Gly
                325                 330                 335
```

```
Pro Pro Thr Phe Arg Leu Thr Gly Ile Gly Pro Pro Gln Pro Asp Asn
            340                 345                 350

Thr Asp Ala Leu Gln Gln Val Gly Trp Lys Leu Ala Gln Leu Ala Gln
        355                 360                 365

Asn Ile Gly Val Gln Phe Glu Phe Arg Gly Phe Val Cys Asn Ser Leu
    370                 375                 380

Ala Asp Leu Asp Pro Lys Met Leu Glu Ile Arg Pro Gly Glu Ala Val
385                 390                 395                 400

Ala Val Asn Ser Val Phe Glu Leu His Arg Met Leu Ala Arg Pro Gly
                405                 410                 415

Ser Val Asp Lys Val Leu Asp Thr Val Lys Lys Ile Lys Pro Lys Ile
            420                 425                 430

Val Thr Ile Val Glu Gln Glu Ala Asn His Asn Gly Pro Gly Phe Leu
        435                 440                 445

Asp Arg Phe Thr Glu Ala Leu His Tyr Tyr Ser Ser Leu Phe Asp Ser
    450                 455                 460

Leu Glu Gly Ser Ser Ser Ser Thr Gly Leu Gly Ser Pro Asn Gln Asp
465                 470                 475                 480

Leu Leu Met Ser Glu Leu Tyr Leu Gly Arg Gln Ile Cys Asn Val Val
                485                 490                 495

Ala Asn Glu Gly Ala Asp Arg Val Glu Arg His Glu Thr Leu Ser Gln
            500                 505                 510

Trp Arg Gly Arg Leu Asp Ser Ala Gly Phe Asp Pro Val His Leu Gly
        515                 520                 525

Ser Asn Ala Phe Lys Gln Ala Ser Met Leu Leu Ala Leu Phe Ala Gly
    530                 535                 540

Gly Asp Gly Tyr Arg Val Glu Glu Asn Asn Gly Cys Leu Met Leu Gly
545                 550                 555                 560

Trp His Thr Arg Pro Leu Ile Ala Thr Ser Ala Trp Lys Leu Pro Ser
                565                 570                 575

Pro Asn Asp Leu His Cys Lys Leu
            580

<210> SEQ ID NO 30
<211> LENGTH: 94
<212> TYPE: PRT
<213> ORGANISM: Glycine max

<400> SEQUENCE: 30

Ala Gly Val Arg Leu Val His Thr Leu Leu Ala Cys Ala Glu Ala Val
1               5                   10                  15

Gln Gln Glu Asn Leu Lys Leu Ala Asp Ala Leu Val Lys His Val Gly
            20                  25                  30

Ile Leu Ala Ala Ser Gln Ala Gly Ala Met Arg Lys Val Ala Ser Tyr
        35                  40                  45

Phe Ala Gln Ala Leu Ala Arg Arg Ile Tyr Gly Ile Phe Pro Glu Glu
    50                  55                  60

Thr Leu Asp Ser Ser Phe Ser Asp Val Leu His Met His Phe Tyr Glu
65                  70                  75                  80

Ser Cys Pro Tyr Leu Lys Phe Ala His Phe Thr Ala Asn Gln
                85                  90

<210> SEQ ID NO 31
<211> LENGTH: 533
<212> TYPE: PRT
<213> ORGANISM: Arabidopsis thaliana
```

```
<400> SEQUENCE: 31

Met Lys Arg Asp His His His His His His Gln Asp Lys Lys Thr Met
 1               5                  10                  15

Met Met Asn Glu Glu Asp Asp Gly Asn Gly Met Asp Glu Leu Leu Ala
             20                  25                  30

Val Leu Gly Tyr Lys Val Arg Ser Ser Glu Met Ala Asp Val Ala Gln
         35                  40                  45

Lys Leu Glu Gln Leu Glu Val Met Met Ser Asn Val Gln Glu Asp Asp
     50                  55                  60

Leu Ser Gln Leu Ala Thr Glu Thr Val His Tyr Asn Pro Ala Glu Leu
 65                  70                  75                  80

Tyr Thr Trp Leu Asp Ser Met Leu Thr Asp Leu Asn Pro Pro Ser Ser
                 85                  90                  95

Asn Ala Glu Tyr Asp Leu Lys Ala Ile Pro Gly Asp Ala Ile Leu Asn
            100                 105                 110

Gln Phe Ala Ile Asp Ser Ala Ser Ser Asn Gln Gly Gly Gly Gly Gly
            115                 120                 125

Asp Thr Tyr Thr Thr Asn Lys Arg Leu Lys Cys Ser Asn Gly Val Val
            130                 135                 140

Glu Thr Thr Thr Ala Thr Ala Glu Ser Thr Arg His Val Val Leu Val
145                 150                 155                 160

Asp Ser Gln Glu Asn Gly Val Arg Leu Val His Ala Leu Leu Ala Cys
                165                 170                 175

Ala Glu Ala Val Gln Lys Glu Asn Leu Thr Val Ala Glu Ala Leu Val
            180                 185                 190

Lys Gln Ile Gly Phe Leu Ala Val Ser Gln Ile Gly Ala Met Arg Lys
            195                 200                 205

Val Ala Thr Tyr Phe Ala Glu Ala Leu Ala Arg Arg Ile Tyr Arg Leu
        210                 215                 220

Ser Pro Ser Gln Ser Pro Ile Asp His Ser Leu Ser Asp Thr Leu Gln
225                 230                 235                 240

Met His Phe Tyr Glu Thr Cys Pro Tyr Leu Lys Phe Ala His Phe Thr
                245                 250                 255

Ala Asn Gln Ala Ile Leu Glu Ala Phe Gln Gly Lys Lys Arg Val His
            260                 265                 270

Val Ile Asp Phe Ser Met Ser Gln Gly Leu Gln Trp Pro Ala Leu Met
        275                 280                 285

Gln Ala Leu Ala Leu Arg Pro Gly Gly Pro Pro Val Phe Arg Leu Thr
    290                 295                 300

Gly Ile Gly Pro Pro Ala Pro Asp Asn Phe Asp Tyr Leu His Glu Val
305                 310                 315                 320

Gly Cys Lys Leu Ala His Leu Ala Glu Ala Ile His Val Glu Phe Glu
                325                 330                 335

Tyr Arg Gly Phe Val Ala Asn Thr Leu Ala Asp Leu Asp Ala Ser Met
            340                 345                 350

Leu Glu Leu Arg Pro Ser Glu Ile Glu Ser Val Ala Val Asn Ser Val
        355                 360                 365

Phe Glu Leu His Lys Leu Leu Gly Arg Pro Gly Ala Ile Asp Lys Val
    370                 375                 380

Leu Gly Val Val Asn Gln Ile Lys Pro Glu Ile Phe Thr Val Val Glu
385                 390                 395                 400

Gln Glu Ser Asn His Asn Ser Pro Ile Phe Leu Asp Arg Phe Thr Glu
                405                 410                 415
```

```
Ser Leu His Tyr Tyr Ser Thr Leu Phe Asp Ser Leu Glu Gly Val Pro
            420                 425                 430

Ser Gly Gln Asp Lys Val Met Ser Glu Val Tyr Leu Gly Lys Gln Ile
        435                 440                 445

Cys Asn Val Val Ala Cys Asp Gly Pro Asp Arg Val Glu Arg His Glu
    450                 455                 460

Thr Leu Ser Gln Trp Arg Asn Arg Phe Gly Ser Ala Gly Phe Ala Ala
465                 470                 475                 480

Ala His Ile Gly Ser Asn Ala Phe Lys Gln Ala Ser Met Leu Leu Ala
                485                 490                 495

Leu Phe Asn Gly Gly Glu Gly Tyr Arg Val Glu Glu Ser Asp Gly Cys
            500                 505                 510

Leu Met Leu Gly Trp His Thr Arg Pro Leu Ile Ala Thr Ser Ala Trp
            515                 520                 525

Lys Leu Ser Thr Asn
        530

<210> SEQ ID NO 32
<211> LENGTH: 95
<212> TYPE: PRT
<213> ORGANISM: Arabidopsis thaliana

<400> SEQUENCE: 32

Asn Gly Val Arg Leu Val His Ala Leu Leu Ala Cys Ala Glu Ala Val
1               5                   10                  15

Gln Lys Glu Asn Leu Thr Val Ala Glu Ala Leu Val Lys Gln Ile Gly
            20                  25                  30

Phe Leu Ala Val Ser Gln Ile Gly Ala Met Arg Lys Val Ala Thr Tyr
        35                  40                  45

Phe Ala Glu Ala Leu Ala Arg Arg Ile Tyr Arg Leu Ser Pro Ser Gln
    50                  55                  60

Ser Pro Ile Asp His Ser Leu Ser Asp Thr Leu Gln Met His Phe Tyr
65                  70                  75                  80

Glu Thr Cys Pro Tyr Leu Lys Phe Ala His Phe Thr Ala Asn Gln
                85                  90                  95

<210> SEQ ID NO 33
<211> LENGTH: 587
<212> TYPE: PRT
<213> ORGANISM: Arabidopsis thaliana

<400> SEQUENCE: 33

Met Lys Arg Asp His His Gln Phe Gln Gly Arg Leu Ser Asn His Gly
1               5                   10                  15

Thr Ser Ser Ser Ser Ser Ile Ser Lys Asp Lys Met Met Met Val
            20                  25                  30

Lys Lys Glu Glu Asp Gly Gly Gly Asn Met Asp Asp Glu Leu Leu Ala
            35                  40                  45

Val Leu Gly Tyr Lys Val Arg Ser Ser Glu Met Ala Glu Val Ala Leu
    50                  55                  60

Lys Leu Glu Gln Leu Glu Thr Met Met Ser Asn Val Gln Glu Asp Gly
65                  70                  75                  80

Leu Ser His Leu Ala Thr Asp Thr Val His Tyr Asn Pro Ser Glu Leu
                85                  90                  95

Tyr Ser Trp Leu Asp Asn Met Leu Ser Glu Leu Asn Pro Pro Pro Leu
            100                 105                 110
```

-continued

```
Pro Ala Ser Ser Asn Gly Leu Asp Pro Val Leu Pro Ser Pro Glu Ile
            115                 120                 125
Cys Gly Phe Pro Ala Ser Asp Tyr Asp Leu Lys Val Ile Pro Gly Asn
            130                 135                 140
Ala Ile Tyr Gln Phe Pro Ala Ile Asp Ser Ser Ser Ser Asn Asn
145                 150                 155                 160
Gln Asn Lys Arg Leu Lys Ser Cys Ser Ser Pro Asp Ser Met Val Thr
            165                 170                 175
Ser Thr Ser Thr Gly Thr Gln Ile Gly Gly Val Ile Gly Thr Thr Val
            180                 185                 190
Thr Thr Thr Thr Thr Thr Thr Ala Ala Gly Glu Ser Thr Arg Ser
            195                 200                 205
Val Ile Leu Val Asp Ser Gln Glu Asn Gly Val Arg Leu Val His Ala
            210                 215                 220
Leu Met Ala Cys Ala Glu Ala Ile Gln Gln Asn Asn Leu Thr Leu Ala
225                 230                 235                 240
Glu Ala Leu Val Lys Gln Ile Gly Cys Leu Ala Val Ser Gln Ala Gly
            245                 250                 255
Ala Met Arg Lys Val Ala Thr Tyr Phe Ala Glu Ala Leu Ala Arg Arg
            260                 265                 270
Ile Tyr Arg Leu Ser Pro Pro Gln Asn Gln Ile Asp His Cys Leu Ser
            275                 280                 285
Asp Thr Leu Gln Met His Phe Tyr Glu Thr Cys Pro Tyr Leu Lys Phe
            290                 295                 300
Ala His Phe Thr Ala Asn Gln Ala Ile Leu Glu Ala Phe Glu Gly Lys
305                 310                 315                 320
Lys Arg Val His Val Ile Asp Phe Ser Met Asn Gln Gly Leu Gln Trp
            325                 330                 335
Pro Ala Leu Met Gln Ala Leu Ala Leu Arg Glu Gly Gly Pro Pro Thr
            340                 345                 350
Phe Arg Leu Thr Gly Ile Gly Pro Pro Ala Pro Asp Asn Ser Asp His
            355                 360                 365
Leu His Glu Val Gly Cys Lys Leu Ala Gln Leu Ala Glu Ala Ile His
            370                 375                 380
Val Glu Phe Glu Tyr Arg Gly Phe Val Ala Asn Ser Leu Ala Asp Leu
385                 390                 395                 400
Asp Ala Ser Met Leu Glu Leu Arg Pro Ser Asp Thr Glu Ala Val Ala
            405                 410                 415
Val Asn Ser Val Phe Glu Leu His Lys Leu Leu Gly Arg Pro Gly Gly
            420                 425                 430
Ile Glu Lys Val Leu Gly Val Val Lys Gln Ile Lys Pro Val Ile Phe
            435                 440                 445
Thr Val Val Glu Gln Glu Ser Asn His Asn Gly Pro Val Phe Leu Asp
            450                 455                 460
Arg Phe Thr Glu Ser Leu His Tyr Tyr Ser Thr Leu Phe Asp Ser Leu
465                 470                 475                 480
Glu Gly Val Pro Asn Ser Gln Asp Lys Val Met Ser Glu Val Tyr Leu
            485                 490                 495
Gly Lys Gln Ile Cys Asn Leu Val Ala Cys Glu Gly Pro Asp Arg Val
            500                 505                 510
Glu Arg His Glu Thr Leu Ser Gln Trp Gly Asn Arg Phe Gly Ser Ser
            515                 520                 525
```

```
Gly Leu Ala Pro Ala His Leu Gly Ser Asn Ala Phe Lys Gln Ala Ser
    530                 535                 540

Met Leu Leu Ser Val Phe Asn Ser Gly Gln Gly Tyr Arg Val Glu Glu
545                 550                 555                 560

Ser Asn Gly Cys Leu Met Leu Gly Trp His Thr Arg Pro Leu Ile Thr
                565                 570                 575

Thr Ser Ala Trp Lys Leu Ser Thr Ala Ala Tyr
                580                 585

<210> SEQ ID NO 34
<211> LENGTH: 95
<212> TYPE: PRT
<213> ORGANISM: Arabidopsis thaliana

<400> SEQUENCE: 34

Asn Gly Val Arg Leu Val His Ala Leu Met Ala Cys Ala Glu Ala Ile
1               5                   10                  15

Gln Gln Asn Asn Leu Thr Leu Ala Glu Ala Leu Val Lys Gln Ile Gly
            20                  25                  30

Cys Leu Ala Val Ser Gln Ala Gly Ala Met Arg Lys Val Ala Thr Tyr
        35                  40                  45

Phe Ala Glu Ala Leu Ala Arg Arg Ile Tyr Arg Leu Ser Pro Pro Gln
    50                  55                  60

Asn Gln Ile Asp His Cys Leu Ser Asp Thr Leu Gln Met His Phe Tyr
65                  70                  75                  80

Glu Thr Cys Pro Tyr Leu Lys Phe Ala His Phe Thr Ala Asn Gln
                85                  90                  95

<210> SEQ ID NO 35
<211> LENGTH: 511
<212> TYPE: PRT
<213> ORGANISM: Arabidopsis thaliana

<400> SEQUENCE: 35

Met Lys Arg Glu His Asn His Arg Glu Ser Ser Ala Gly Glu Gly Gly
1               5                   10                  15

Ser Ser Ser Met Thr Thr Val Ile Lys Glu Glu Ala Ala Gly Val Asp
            20                  25                  30

Glu Leu Leu Val Val Leu Gly Tyr Lys Val Arg Ser Ser Asp Met Ala
        35                  40                  45

Asp Val Ala His Lys Leu Glu Gln Leu Glu Met Val Leu Gly Asp Gly
    50                  55                  60

Ile Ser Asn Leu Ser Asp Glu Thr Val His Tyr Asn Pro Ser Asp Leu
65                  70                  75                  80

Ser Gly Trp Val Glu Ser Met Leu Ser Asp Leu Asp Pro Thr Arg Ile
                85                  90                  95

Gln Glu Lys Pro Asp Ser Glu Tyr Asp Leu Arg Ala Ile Pro Gly Ser
                100                 105                 110

Ala Val Tyr Pro Arg Asp Glu His Val Thr Arg Arg Ser Lys Arg Thr
            115                 120                 125

Arg Ile Glu Ser Glu Leu Ser Thr Arg Ser Val Val Leu Asp
        130                 135                 140

Ser Gln Glu Thr Gly Val Arg Leu Val His Ala Leu Leu Ala Cys Ala
145                 150                 155                 160

Glu Ala Val Gln Gln Asn Asn Leu Lys Leu Ala Asp Ala Leu Val Lys
                165                 170                 175
```

His Val Gly Leu Leu Ala Ser Ser Gln Ala Gly Ala Met Arg Lys Val
                180                 185                 190

Ala Thr Tyr Phe Ala Glu Gly Leu Ala Arg Arg Ile Tyr Arg Ile Tyr
            195                 200                 205

Pro Arg Asp Asp Val Ala Leu Ser Ser Phe Ser Asp Thr Leu Gln Ile
        210                 215                 220

His Phe Tyr Glu Ser Cys Pro Tyr Leu Lys Phe Ala His Phe Thr Ala
225                 230                 235                 240

Asn Gln Ala Ile Leu Glu Val Phe Ala Thr Ala Glu Lys Val His Val
                245                 250                 255

Ile Asp Leu Gly Leu Asn His Gly Leu Gln Trp Pro Ala Leu Ile Gln
            260                 265                 270

Ala Leu Ala Leu Arg Pro Asn Gly Pro Pro Asp Phe Arg Leu Thr Gly
        275                 280                 285

Ile Gly Tyr Ser Leu Thr Asp Ile Gln Glu Val Gly Trp Lys Leu Gly
290                 295                 300

Gln Leu Ala Ser Thr Ile Gly Val Asn Phe Glu Phe Lys Ser Ile Ala
305                 310                 315                 320

Leu Asn Asn Leu Ser Asp Leu Lys Pro Glu Met Leu Asp Ile Arg Pro
                325                 330                 335

Gly Leu Glu Ser Val Ala Val Asn Ser Val Phe Glu Leu His Arg Leu
            340                 345                 350

Leu Ala His Pro Gly Ser Ile Asp Lys Phe Leu Ser Thr Ile Lys Ser
        355                 360                 365

Ile Arg Pro Asp Ile Met Thr Val Val Glu Gln Glu Ala Asn His Asn
370                 375                 380

Gly Thr Val Phe Leu Asp Arg Phe Thr Glu Ser Leu His Tyr Tyr Ser
385                 390                 395                 400

Ser Leu Phe Asp Ser Leu Glu Gly Pro Pro Ser Gln Asp Arg Val Met
                405                 410                 415

Ser Glu Leu Phe Leu Gly Arg Gln Ile Leu Asn Leu Val Ala Cys Glu
            420                 425                 430

Gly Glu Asp Arg Val Glu Arg His Glu Thr Leu Asn Gln Trp Arg Asn
        435                 440                 445

Arg Phe Gly Leu Gly Gly Phe Lys Pro Val Ser Ile Gly Ser Asn Ala
450                 455                 460

Tyr Lys Gln Ala Ser Met Leu Leu Ala Leu Tyr Ala Gly Ala Asp Gly
465                 470                 475                 480

Tyr Asn Val Glu Glu Asn Glu Gly Cys Leu Leu Leu Gly Trp Gln Thr
                485                 490                 495

Arg Pro Leu Ile Ala Thr Ser Ala Trp Arg Ile Asn Arg Val Glu
            500                 505                 510

<210> SEQ ID NO 36
<211> LENGTH: 95
<212> TYPE: PRT
<213> ORGANISM: Arabidopsis thaliana

<400> SEQUENCE: 36

Thr Gly Val Arg Leu Val His Ala Leu Leu Ala Cys Ala Glu Ala Val
1               5                   10                  15

Gln Gln Asn Asn Leu Lys Leu Ala Asp Ala Leu Val Lys His Val Gly
                20                  25                  30

Leu Leu Ala Ser Ser Gln Ala Gly Ala Met Arg Lys Val Ala Thr Tyr
            35                  40                  45

```
Phe Ala Glu Gly Leu Ala Arg Arg Ile Tyr Arg Ile Tyr Pro Arg Asp
 50                  55                  60

Asp Val Ala Leu Ser Ser Phe Ser Asp Thr Leu Gln Ile His Phe Tyr
 65                  70                  75                  80

Glu Ser Cys Pro Tyr Leu Lys Phe Ala His Phe Thr Ala Asn Gln
                 85                  90                  95

<210> SEQ ID NO 37
<211> LENGTH: 547
<212> TYPE: PRT
<213> ORGANISM: Arabidopsis thaliana

<400> SEQUENCE: 37

Met Lys Arg Gly Tyr Gly Glu Thr Trp Asp Pro Pro Lys Pro Leu
 1               5                  10                  15

Pro Ala Ser Arg Ser Gly Glu Gly Pro Ser Met Ala Asp Lys Lys
             20                  25                  30

Ala Asp Asp Asn Asn Ser Asn Met Asp Glu Leu Leu Ala
         35                  40                  45

Val Leu Gly Tyr Lys Val Arg Ser Ser Glu Met Ala Glu Val Ala Gln
 50                  55                  60

Lys Leu Glu Gln Leu Glu Met Val Leu Ser Asn Asp Val Gly Ser
 65                  70                  75                  80

Thr Val Leu Asn Asp Ser Val His Tyr Asn Pro Ser Asp Leu Ser Asn
                 85                  90                  95

Trp Val Glu Ser Met Leu Ser Glu Leu Asn Asn Pro Ala Ser Ser Asp
                100                 105                 110

Leu Asp Thr Thr Arg Ser Cys Val Asp Arg Ser Glu Tyr Asp Leu Arg
                115                 120                 125

Ala Ile Pro Gly Leu Ser Ala Phe Pro Lys Glu Glu Val Phe Asp
130                 135                 140

Glu Glu Ala Ser Ser Lys Arg Ile Arg Leu Gly Ser Trp Cys Glu Ser
145                 150                 155                 160

Ser Asp Glu Ser Thr Arg Ser Val Val Leu Val Asp Ser Gln Glu Thr
                165                 170                 175

Gly Val Arg Leu Val His Ala Leu Val Ala Cys Ala Glu Ala Ile His
                180                 185                 190

Gln Glu Asn Leu Asn Leu Ala Asp Ala Leu Val Lys Arg Val Gly Thr
                195                 200                 205

Leu Ala Gly Ser Gln Ala Gly Ala Met Gly Lys Val Ala Thr Tyr Phe
210                 215                 220

Ala Gln Ala Leu Ala Arg Arg Ile Tyr Arg Asp Tyr Thr Ala Glu Thr
225                 230                 235                 240

Asp Val Cys Ala Ala Val Asn Pro Ser Phe Glu Glu Val Leu Glu Met
                245                 250                 255

His Phe Tyr Glu Ser Cys Pro Tyr Leu Lys Phe Ala His Phe Thr Ala
                260                 265                 270

Asn Gln Ala Ile Leu Glu Ala Val Thr Thr Ala Arg Arg Val His Val
                275                 280                 285

Ile Asp Leu Gly Leu Asn Gln Gly Met Gln Trp Pro Ala Leu Met Gln
                290                 295                 300

Ala Leu Ala Leu Arg Pro Gly Gly Pro Pro Ser Phe Arg Leu Thr Gly
305                 310                 315                 320
```

```
Ile Gly Pro Pro Gln Thr Glu Asn Ser Asp Ser Leu Gln Gln Leu Gly
            325                 330                 335

Trp Lys Leu Ala Gln Phe Ala Gln Asn Met Gly Val Glu Phe Glu Phe
        340                 345                 350

Lys Gly Leu Ala Ala Glu Ser Leu Ser Asp Leu Glu Pro Glu Met Phe
            355                 360                 365

Glu Thr Arg Pro Glu Ser Glu Thr Leu Val Val Asn Ser Val Phe Glu
        370                 375                 380

Leu His Arg Leu Leu Ala Arg Ser Gly Ser Ile Glu Lys Leu Leu Asn
385                 390                 395                 400

Thr Val Lys Ala Ile Lys Pro Ser Ile Val Thr Val Val Glu Gln Glu
                405                 410                 415

Ala Asn His Asn Gly Ile Val Phe Leu Asp Arg Phe Asn Glu Ala Leu
            420                 425                 430

His Tyr Tyr Ser Ser Leu Phe Asp Ser Leu Glu Asp Ser Tyr Ser Leu
        435                 440                 445

Pro Ser Gln Asp Arg Val Met Ser Glu Val Tyr Leu Gly Arg Gln Ile
    450                 455                 460

Leu Asn Val Val Ala Ala Glu Gly Ser Asp Arg Val Glu Arg His Glu
465                 470                 475                 480

Thr Ala Ala Gln Trp Arg Ile Arg Met Lys Ser Ala Gly Phe Asp Pro
                485                 490                 495

Ile His Leu Gly Ser Ser Ala Phe Lys Gln Ala Ser Met Leu Leu Ser
            500                 505                 510

Leu Tyr Ala Thr Gly Asp Gly Tyr Arg Val Glu Glu Asn Asp Gly Cys
        515                 520                 525

Leu Met Ile Gly Trp Gln Thr Arg Pro Leu Ile Thr Thr Ser Ala Trp
    530                 535                 540

Lys Leu Ala
545

<210> SEQ ID NO 38
<211> LENGTH: 99
<212> TYPE: PRT
<213> ORGANISM: Arabidopsis thaliana

<400> SEQUENCE: 38

Thr Gly Val Arg Leu Val His Ala Leu Val Ala Cys Ala Glu Ala Ile
1               5                   10                  15

His Gln Glu Asn Leu Asn Leu Ala Asp Ala Leu Val Lys Arg Val Gly
            20                  25                  30

Thr Leu Ala Gly Ser Gln Ala Gly Ala Met Gly Lys Val Ala Thr Tyr
        35                  40                  45

Phe Ala Gln Ala Leu Ala Arg Arg Ile Tyr Arg Asp Tyr Thr Ala Glu
    50                  55                  60

Thr Asp Val Cys Ala Ala Val Asn Pro Ser Phe Glu Glu Val Leu Glu
65                  70                  75                  80

Met His Phe Tyr Glu Ser Cys Pro Tyr Leu Lys Phe Ala His Phe Thr
                85                  90                  95

Ala Asn Gln

<210> SEQ ID NO 39
<211> LENGTH: 523
<212> TYPE: PRT
<213> ORGANISM: Arabidopsis thaliana
```

<400> SEQUENCE: 39

```
Met Lys Arg Ser His Gln Glu Thr Ser Val Glu Glu Ala Pro Ser
  1               5                  10                  15
Met Val Glu Lys Leu Glu Asn Gly Cys Gly Gly Gly Asp Asp Asn
                 20                  25                  30
Met Asp Glu Phe Leu Ala Val Leu Gly Tyr Lys Val Arg Ser Ser Asp
                 35                  40                  45
Met Ala Asp Val Ala Gln Lys Leu Glu Gln Leu Glu Met Val Leu Ser
 50                  55                  60
Asn Asp Ile Ala Ser Ser Asn Ala Phe Asn Asp Thr Val His Tyr
 65                  70                  75                  80
Asn Pro Ser Asp Leu Ser Gly Trp Ala Gln Ser Met Leu Ser Asp Leu
                 85                  90                  95
Asn Tyr Tyr Pro Asp Leu Asp Pro Asn Arg Ile Cys Asp Leu Arg Pro
                100                 105                 110
Ile Thr Asp Asp Asp Glu Cys Cys Ser Ser Asn Ser Asn Ser Asn Lys
                115                 120                 125
Arg Ile Arg Leu Gly Pro Trp Cys Asp Ser Val Thr Ser Glu Ser Thr
130                 135                 140
Arg Ser Val Val Leu Ile Glu Glu Thr Gly Val Arg Leu Val Gln Ala
145                 150                 155                 160
Leu Val Ala Cys Ala Glu Ala Val Gln Leu Glu Asn Leu Ser Leu Ala
                165                 170                 175
Asp Ala Leu Val Lys Arg Val Gly Leu Leu Ala Ala Ser Gln Ala Gly
                180                 185                 190
Ala Met Gly Lys Val Ala Thr Tyr Phe Ala Glu Ala Leu Ala Arg Arg
                195                 200                 205
Ile Tyr Arg Ile His Pro Ser Ala Ala Ile Asp Pro Ser Phe Glu
210                 215                 220
Glu Ile Leu Gln Met Asn Phe Tyr Asp Ser Cys Pro Tyr Leu Lys Phe
225                 230                 235                 240
Ala His Phe Thr Ala Asn Gln Ala Ile Leu Glu Ala Val Thr Thr Ser
                245                 250                 255
Arg Val Val His Val Ile Asp Leu Gly Leu Asn Gln Gly Met Gln Trp
                260                 265                 270
Pro Ala Leu Met Gln Ala Leu Ala Leu Arg Pro Gly Gly Pro Pro Ser
                275                 280                 285
Phe Arg Leu Thr Gly Val Gly Asn Pro Ser Asn Arg Glu Gly Ile Gln
                290                 295                 300
Glu Leu Gly Trp Lys Leu Ala Gln Leu Ala Gln Ala Ile Gly Val Glu
305                 310                 315                 320
Phe Lys Phe Asn Gly Leu Thr Thr Glu Arg Leu Ser Asp Leu Glu Pro
                325                 330                 335
Asp Met Phe Glu Thr Arg Thr Glu Ser Glu Thr Leu Val Val Asn Ser
                340                 345                 350
Val Phe Glu Leu His Pro Val Leu Ser Gln Pro Gly Ser Ile Glu Lys
                355                 360                 365
Leu Leu Ala Thr Val Lys Ala Val Lys Pro Gly Leu Val Thr Val Val
                370                 375                 380
Glu Gln Glu Ala Asn His Asn Gly Asp Val Phe Leu Asp Arg Phe Asn
385                 390                 395                 400
Glu Ala Leu His Tyr Tyr Ser Ser Leu Phe Asp Ser Leu Glu Asp Gly
                405                 410                 415
```

```
Val Val Ile Pro Ser Gln Asp Arg Val Met Ser Glu Val Tyr Leu Gly
            420                 425                 430

Arg Gln Ile Leu Asn Leu Val Ala Thr Glu Gly Ser Arg Ile Glu
        435                 440                 445

Arg His Glu Thr Leu Ala Gln Trp Arg Lys Arg Met Gly Ser Ala Gly
    450                 455                 460

Phe Asp Pro Val Asn Leu Gly Ser Asp Ala Phe Lys Gln Ala Ser Leu
465                 470                 475                 480

Leu Leu Ala Leu Ser Gly Gly Asp Gly Tyr Arg Val Glu Glu Asn
                485                 490                 495

Asp Gly Ser Leu Met Leu Ala Trp Gln Thr Lys Pro Leu Ile Ala Ala
            500                 505                 510

Ser Ala Trp Lys Leu Ala Ala Glu Leu Arg Arg
                515                 520

<210> SEQ ID NO 40
<211> LENGTH: 95
<212> TYPE: PRT
<213> ORGANISM: Arabidopsis thaliana

<400> SEQUENCE: 40

Thr Gly Val Arg Leu Val Gln Ala Leu Val Ala Cys Ala Glu Ala Val
1               5                   10                  15

Gln Leu Glu Asn Leu Ser Leu Ala Asp Ala Leu Val Lys Arg Val Gly
            20                  25                  30

Leu Leu Ala Ala Ser Gln Ala Gly Ala Met Gly Lys Val Ala Thr Tyr
        35                  40                  45

Phe Ala Glu Ala Leu Ala Arg Arg Ile Tyr Arg Ile His Pro Ser Ala
    50                  55                  60

Ala Ala Ile Asp Pro Ser Phe Glu Glu Ile Leu Gln Met Asn Phe Tyr
65                  70                  75                  80

Asp Ser Cys Pro Tyr Leu Lys Phe Ala His Phe Thr Ala Asn Gln
                85                  90                  95

<210> SEQ ID NO 41
<211> LENGTH: 98
<212> TYPE: PRT
<213> ORGANISM: Artificial Sequence
<220> FEATURE:
<223> OTHER INFORMATION: Consensus dimerization domain sequence
<221> NAME/KEY: VARIANT
<222> LOCATION: 21, 62, 63, 64, 65, 66, 67, 68, 69, 72
<223> OTHER INFORMATION: Xaa = Any Amino Acid
<221> NAME/KEY: VARIANT
<222> LOCATION: 21, 62, 63, 64, 65, 66, 67, 68, 69, 72
<223> OTHER INFORMATION: Xaa = Any Amino Acid

<400> SEQUENCE: 41

Gly Val Arg Leu Val His Ala Leu Leu Ala Cys Ala Glu Ala Val Gln
1               5                   10                  15

Gln Glu Asn Leu Xaa Leu Ala Asp Ala Leu Val Lys Gln Ile Gly Ile
            20                  25                  30

Leu Ala Ala Ser Gln Ala Gly Ala Met Arg Lys Val Ala Thr Tyr Phe
        35                  40                  45

Ala Glu Ala Leu Ala Arg Arg Ile Tyr Arg Ile Phe Pro Xaa Xaa Xaa
    50                  55                  60

Xaa Xaa Xaa Xaa Xaa Leu Asp Xaa Ser Phe Ser Asp Val Leu Gln Met
65                  70                  75                  80
```

```
His Phe Tyr Glu Ser Cys Pro Tyr Leu Lys Phe Ala His Phe Thr Ala
                85                  90                  95

Asn Gln

<210> SEQ ID NO 42
<211> LENGTH: 19
<212> TYPE: DNA
<213> ORGANISM: Artificial Sequence
<220> FEATURE:
<223> OTHER INFORMATION: primer

<400> SEQUENCE: 42
gtctgcacca tcgtcaacc                                             19

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
gaagtccagc tgccagaaac c                                          21
```

USE OF DIMERIZATION DOMAIN COMPONENT STACKS TO MODULATE PLANT ARCHITECTURE

CROSS REFERENCE

This utility application claims the benefit U.S. Provisional Application Ser. Nos. 61/228,195 and 61/286,061, filed Jul. 24, 2009 and Dec. 14, 2009 respectively, which are incorporated herein by reference.

FIELD OF THE INVENTION

The invention relates generally to the field of molecular biology.

BACKGROUND OF THE INVENTION

Harvest index, ratio of grain to total above ground biomass, has remained nearly constant around 50% in maize over the past 100 years (Sinclair, (1998) *Crop Science* 38:638-643; Tollenaar and Wu, (1999) "*Crop Science* 39:1597-1604). Thus, the quadrupling of grain yield over the last 50-60 years has resulted from an increase in total biomass production per unit land area, which has been accomplished by increased planting density (Duvick and Cassman, (1999) *Crop Science* 39:1622-1630). Selection for higher grain yield under increasing planting densities has led to a significant architectural change in plant structure that of relatively erect and narrow leaves to minimize shading. An undesirable consequence of higher density planting (or higher plant populations) has been the increased frequency of stalk and root lodging. The relationship between planting density and biomass production deviates significantly from linearity as the optimal density is approached for maximal biomass yield per unit land area. This is reflected in a proportionately greater reduction in the individual plant biomass, which manifests in the form of weaker stalks and hence increased lodging. In addition, approximately 20% of total biomass at maturity stays in the form of roots in the soil, contributing to its organic matter content (Amos and Walters, 2006). Since both stalk and root lodging are agronomic characteristics affecting harvest index, dwarf type plants could have potential advantages in yield stability.

Dwarf plants have had a major impact on agriculture. Dwarf varieties of wheat (and other small grain cereals) are widely used in North America due to both reduced potential for lodging and response to more intensive management and yield stability and potentially higher yields. There are other benefits that may be realized from the higher harvest index of dwarf crop plants including reductions in the amounts of pesticides and fertilizers required, higher planting densities and reduced labor costs. Dwarf plants provide ease in harvesting, simplified management of crops and potential reductions in water and nutrient use.

In view of the current trends of both increasing human population and the decreasing land area suitable for agriculture, increasing agricultural productivity is, and will continue to be, a challenge of paramount importance. Dwarf crop plants are important components of our agricultural production system. Increased usage of dwarf crop plants may help to meet the agricultural production demands of the future.

Genes that increase stalk strength, i.e., Cellulose Synthase, are responsible for cellulose production in crop plants, can be modified to increase size and strength of various plant tissues. Cellulose in a unit length of the maize stalk was found to be the best indicator of mechanical strength (Appenzeller, et al., (2004) *Cellulose* 11:287-299; Ching, et al., (2006)). Increasing cellulose concentration in the stalk dry matter could lead to improving stalk mechanical strength and increasing biomass which in turn increases yield and potentially harvest index. Improvements in plant strength (biomass) and growth of specific plant tissues (organs) provides plants with greater biomass and increased harvest index.

Flowering time determines maturity, an important agronomic trait. Genes that control the transition from vegetative to reproductive growth are essential for manipulation of flowering time. In maize, flowering genes provide opportunities for enhanced crop yield, adaptation of germplasm to different climatic zones and synchronous flowering for hybrid seed production. The development of inbred lines having modified flowering facilitates the movement of elite germplasm across maturity zones. In addition, additional opportunities exist to increase the rate of grain fill and/or grain dry down to complement changes in the onset of flowering.

The combined controlled expression of plant architecture genes, flowering time genes and dwarfing gene components within transformed plants would not only increase the yield potential and harvest index of crop plants but would also improve the agronomic characteristics that simplify management practices and increase the adaptation of crop species into new geographic areas.

This invention provides means for altering the harvest index of crop plants by modulating the expression of transgenes using multiple stacked plant genes and dwarf gene components, thereby modulating plant architecture. A component of Dwarf gene D8, the dimerization domain (DD), a leucine-zipper dimerization domain (SEQ ID NO: 9) is overexpressed as a dominant negative transgene. The transgene/dimerization domain component stacks are provided in a single transformation vector unit and are used to modulate specific plant organs of a plant that can increase growth, yield and harvest index in plants. The expression in specific plant tissues, such as roots, ears or tassels can lead to elongation of the specific plant organs.

These stacked units could be used to enhance crop plant performance and value in several areas including: 1) plant standability (composed of stalk and root lodging), harvest index and yield potential; 2) modification of specific plant organ size; 3) plant dry matter as a feedstock for ethanol or for other renewable bioproducts and 4) silage.

BRIEF SUMMARY OF THE INVENTION

Compositions and methods for controlling plant growth and dimerization domain component stack formation for increasing yield in a plant are provided. The compositions include dimerization domain component stacks from maize. Compositions of the invention comprise amino acid sequences and nucleotide sequences selected from SEQ ID NOS: 1-22 as well as variants and fragments thereof.

Polynucleotides encoding the dimerization domain component stacks are provided in DNA constructs for expression in a plant of interest. Expression cassettes, plants, plant cells, plant parts and seeds comprising the sequences of the invention are further provided. In specific embodiments, the polynucleotide is operably linked to a constitutive promoter.

Methods for modulating the level of a dimerization domain component stack sequence in a plant or plant part are provided. The methods comprise introducing into a plant or plant part a heterologous polynucleotide comprising a dimerization domain component stack sequence of the invention. The level of a dimerization domain component stack polypeptide can be increased or decreased. Such method can be used to increase the yield in plants; in one embodiment, the method is used to increase grain yield in cereals.

The plant hormone GA is active in various growth processes, specifically the elongation of stem and root during plant growth. The D8 (and D9) genes of maize encode for transcriptional regulators that act as inhibitors of the giberellic acid signal transduction pathway, and consist of a DELLA and GRAS domain. The GA receptor interacts with DELLA proteins in the presence of GA, which leads to poly-ubiquitination of the DELLA protein. Poly-ubiquination signals for protein degradation by the 26S proteasome. The degradation of the DELLA proteins removes their inhibition of the GA growth response. In general, the rate of degradation of the D8/D9 proteins appears to correlate with plant size (i.e. slower degradation results in less response to GA, less elongation and a greater height reduction). Deletions and specific mutations in the DELLA domain of D8 are responsible for the dwarfing phenotype because of the altered degradation kinetics of these proteins.

The D8 (and D9) proteins are thought to function in-vivo as a dimer, whose catabolism regulates plant elongation. Dimers of strong dwarf genes such as D8 are less sensitive to degradation while moderate dwarf genes such as D8MPL are relatively more sensitive to degradation. The native wild type gene d8 is sensitive to degradation and a tall or normal height is observed. A specific leucine-zipper domain of the D8 protein, ZM-D8 243-331, is involved in the formation of the dimers. An altered dimerization domain protein is formed by over expression of the ZM-D8 243-331 protein. These truncated protein fragments compete for binding to the leucine-zipper domain of full length D8 and D9. This competitive binding leads to the formation of defective dimers having a full-length protein::truncated protein. The resultant non-functional dimer lacks the capacity to inhibit the GA response, and when present in a plant or plant organ increases elongation. Further, tissue specific expression using promoters for specific plant organs such as roots, ears or tassels are expected to have increased size (length) compared to dwarf plants. Specifically, a dwarf plant type could have roots that are similar in size to wild type or normal statured plants.

BRIEF DESCRIPTION OF THE DRAWINGS

FIG. 5: Alignment of DD domains across various species, *Glycine max* (SEQ ID NOS: 24, 26, 28 30, *Arabidopsis thaliana* (SEQ ID NOS: 32, 34, 36, 38 and 40), *Zea mays* (SEQ ID NO: 19), showing conserved regions and consensus sequence (SEQ ID NO: 41).

DETAILED DESCRIPTION OF THE INVENTION

Figure 1:
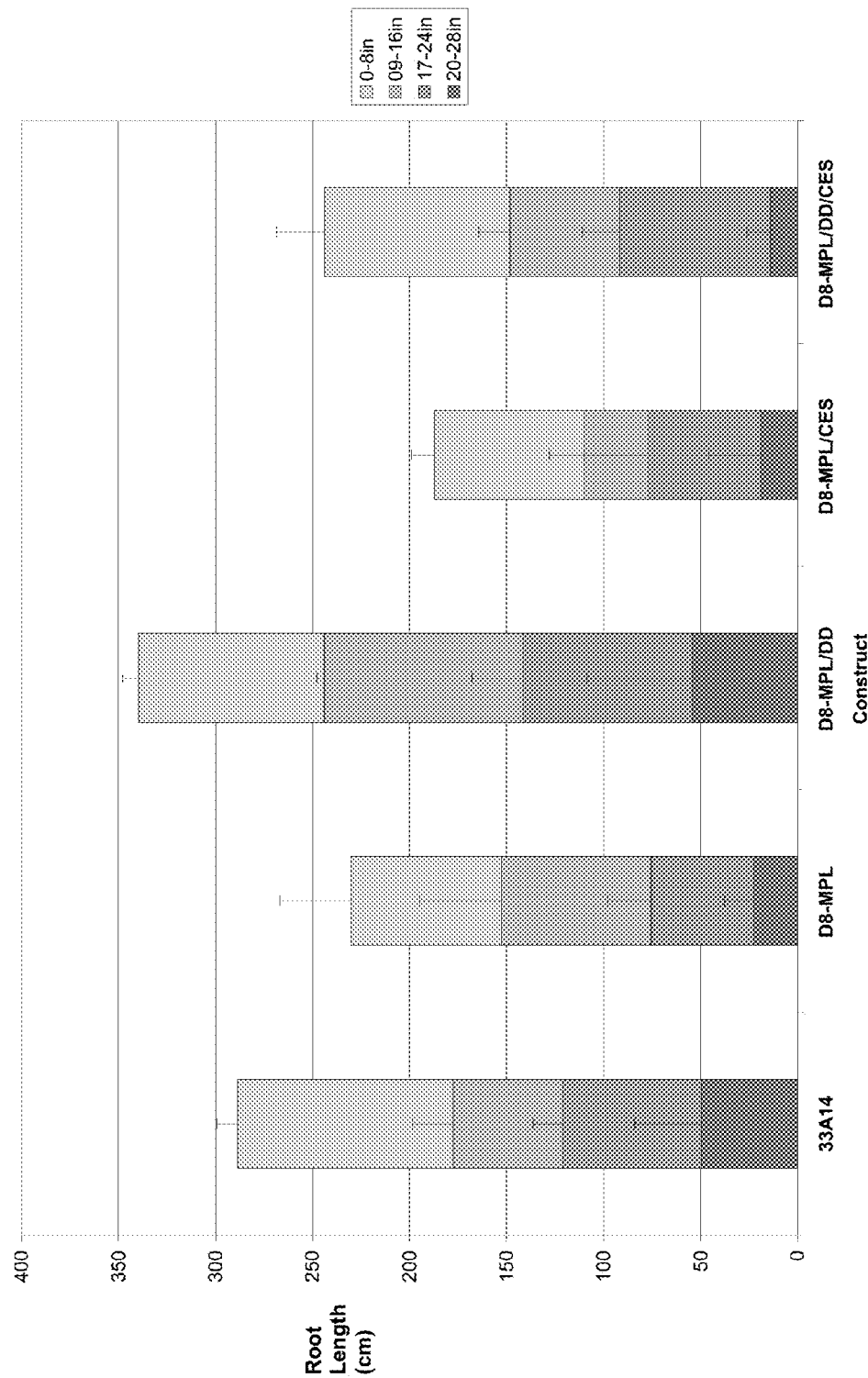
FIG. 1: Root Growth as measured in Mini Rhizitrons in Johnston IA in 2006 with Hybrid 33A14, PHP24843, PHP26998 and PHP26998

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier, et al., THE MICROBIAL WORLD, $5^{th}$ ed., Prentice-Hall (1986); Dhringra and Sinclair, BASIC PLANT PATHOLOGY METHODS, CRC Press (1985); Maniatis, et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984) and the series METHODS IN ENZYMOLOGY, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., DIAGNOSTIC MOLECULAR MICROBIOLOGY: PRINCIPLES AND APPLICATIONS, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V) and
6) Phenylalanine (F), Tyrosine (Y), Tryptophan (W).

See also, Creighton, PROTEINS, W.H. Freeman and Co. (1984).

As used herein in the context of nucleic acids in general, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

The term "consisting essentially of" or "consists essentially of" in the context of a nucleic acid sequence encoding a dimerization domain or the amino acid sequence of the dimerization domain, generally refers to a recombinant dimerization domain sequence and any other sequence that does not materially alter the basic binding property of the dimerization domain fragment, for example, to form a defective dimer with the target protein. For example, the ZM-D8 243-331 is a portion of the D8 protein that corresponds to a dimerization domain region. In an embodiment, this domain fragment may contain other sequences both to the amino and/or carboxy-terminus as long as the additional sequences do not materially alter the basic binding characteristics of the dimerization domain fragment with the target protein that results in reduced inhibition by giberrellic acid (GA) hormone. For example, a full-length D8 amino acid sequence is not suitable as it will result in the formation of a functional dimer that blocks GA response.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolumn* (Yamao, et al., (1985) *Proc. Natl. Acad. Sci. USA* 82:2306-2309) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "dimerization domain component stack nucleic acid" means a nucleic acid comprising a polynucleotide ("dimerization domain component stack polynucleotide") encoding a dimerization domain component stack polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook, et al., MOLECULAR CLONING: A LABORATORY MANUAL, $2^{nd}$ ed., vols. 1-3 (1989) and CURRENT PROTOCOLS IN MOLECULAR BIOLOGY, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. Also included are grass plants from the Poaceae family including but not limited to the genera: *Poa, Agrostis, Lolium, Festuca, Zoysia, Cynodon, Stenotaphrum, Paspalum, Eremochloa, Axonopus, Buchloe, Bouteloua*, including Bluegrass, Bentgrass, Ryegrasses, Fescues, Zoysiagrass, Bermudagrass, St. Augustine grass, Bahiagrass, Centipedegrass, Carpetgrass, Buffalograss and Gramagrass. A particularly preferred plant is *Zea mays*.

As used herein, "yield" includes reference to bushels per acre of a grain crop at harvest, as adjusted for grain moisture (15% typically). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

The term "dimerization domain component stack polypeptide" refers to one or more amino acid sequences that include the dimerization domain region of interest and another polypeptide sequence that is not the same parent sequence from which the dimerization domain sequence was derived. The term is also inclusive of fragments, variants, homologs, alleles or precursors (e.g., preproproteins or proproteins) thereof. A "dimerization domain component stack protein" comprises a dimerization domain component stack polypeptide. Unless otherwise stated, the term "dimerization domain component stack nucleic acid" means a nucleic acid comprising a polynucleotide ("dimerization domain component stack polynucleotide") encoding a dimerization domain component stack polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention. The term "recombinant polypeptide" or "recombinant nucleic acid" refers to the peptide and nucleic acid sequences that have been modified such that they do not exist in nature in their present form.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The term "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-84: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, N.Y. (1993) and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package®, Version 8 (available from Genetics Computer Group (GCG® programs (Accelrys, Inc., San Diego, Calif.)). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses dimerization domain polynucleotides and polypeptides. The novel nucleotides and proteins of the invention have an expression pattern which indicates that they alter cell wall formation and thus play an important role in plant development. The polynucleotides are expressed in various plant tissues. The polynucleotides and polypeptides thus provide an opportunity to manipulate plant development to alter seed and vegetative tissue development, timing or composition. This may be used to create a sterile plant, a seedless plant or a plant with altered endosperm composition.

Nucleic Acids

The present invention provides, inter alia, isolated nucleic acids of RNA, DNA and analogs and/or chimeras thereof, comprising a dimerization domain polynucleotide.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The dimerization domain nucleic acids include isolated dimerization domain polynucleotides which are inclusive of:
- (a) a polynucleotide encoding a dimerization domain polypeptide and conservatively modified and polymorphic variants thereof;
- (b) a polynucleotide having at least 70% sequence identity with polynucleotides of (a) or (b);
- (c) complementary sequences of polynucleotides of (a) or (b).

The following table, Table 1, lists the specific identities of the sequences disclosed herein.

TABLE 1

| SEQ ID NO: | Identity |
|---|---|
| SEQ ID NO: 1 | MS-S2A promoter |
| SEQ ID NO: 2 | ZmCesA10 polynucleotide |
| SEQ ID NO: 3 | Pin II terminator |
| SEQ ID NO: 4 | F3.7 promoter |
| SEQ ID NO: 5 | ZmCesA4 polynucleotide |
| SEQ ID NO: 6 | ZmD8 polynucleotide |
| SEQ ID NO: 7 | ZmNAS2 promoter |
| SEQ ID NO: 8 | ZmNAS2 5'UTR |
| SEQ ID NO: 9 | ZmD8 Dimerization Domain polynucletide (start and stop codons are artificial appendages to the 243-331 coding sequence) |
| SEQ ID NO: 10 | NOS terminator |
| SEQ ID NO: 11 | ZmFTM1 polynucleotide |
| SEQ ID NO: 12 | GmGAI1 polynucleotide |
| SEQ ID NO: 13 | ZRP2.47 promoter |
| SEQ ID NO: 14 | ADH1 intron |
| SEQ ID NO: 15 | ZmRootMet2 promoter |
| SEQ ID NO: 16 | ZmCesA10 polypeptide |
| SEQ ID NO: 17 | ZmCesA4 polypeptide |
| SEQ ID NO: 18 | ZmD8 polypeptide |
| SEQ ID NO: 19 | ZmD8 243-331 Dimerization Domain polypeptide (ATG start codon is artificial and leads to an N-terminal methionine added to the 243-331 amino acids). |
| SEQ ID NO: 20 | ZmFTM1 polypeptide |
| SEQ ID NO: 21 | GmGAI1 Dimerization Domain polypeptide |
| SEQ ID NO: 22 | GmGAI1 polypeptide |
| SEQ ID NO: 23 | Gm 05g27190.1 |
| SEQ ID NO: 24 | Gm 05g27190.1 Dimerization Domain |
| SEQ ID NO: 25 | Gm 08g10140.1 |
| SEQ ID NO: 26 | Gm 08g10140.1 Dimerization Domain |
| SEQ ID NO: 27 | Gm 11g33720.1 |
| SEQ ID NO: 28 | Gm 11g33720.1 Dimerization Domain |
| SEQ ID NO: 29 | Gm 18g04500.1 |
| SEQ ID NO: 30 | Gm 18g04500.1 Dimerization Domain |
| SEQ ID NO: 31 | At GAI |
| SEQ ID NO: 32 | At GAI Dimerization Domain |
| SEQ ID NO: 33 | At RGA |
| SEQ ID NO: 34 | At RGA Dimerization Domain |
| SEQ ID NO: 35 | At RGL1 |
| SEQ ID NO: 36 | At RGL1 Dimerization Domain |
| SEQ ID NO: 37 | At RGL2 |
| SEQ ID NO: 38 | At RGL2 Dimerization Domain |
| SEQ ID NO: 39 | At RGL3 |
| SEQ ID NO: 40 | At RGL3 Dimerization Domain |
| SEQ ID NO: 41 | Consensus Dimerization Domain |
| SEQ ID NO: 42 | Primer |
| SEQ ID NO: 43 | Primer |

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter or linker for cloning and/or expression of a polynucleotide of the present invention. Additional sequences may be added to such cloning and/or expression sequences to optimize their function in cloning and/or expression, to aid in isolation of the polynucleotide or to improve the introduction of the polynucleotide into a cell. Typically, the length of a nucleic acid of the present invention less the length of its polynucleotide of the present invention is less than 20 kilobase pairs, often less than 15 kb and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSIox and lambda MOSEIox. Optional vectors for the present invention, include but are not limited to, lambda ZAP II and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G> 7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395; or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication number 96/19256. See also, Zhang, et al., (1997) *Proc. Natl. Acad. Sci. USA* 94:4504-9 and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683, 439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3): 291-300); ALS promoter, as described in PCT Application Number WO 96/30530; GOS2 (U.S. Pat. No. 6,504,083) and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters (Rab17, RAD29). Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium*

*tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell. Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, THE MAIZE HANDBOOK, Chapter 116, Freeling and Walbot, eds., Springer, N.Y. (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference) or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the dimerization domain component stack polynucleotide is the preferred construct for expression in maize for the present invention.

The vector comprising the sequences from a polynucleotide of the present disclosure will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene) or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA,* 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation and a transcription/translation terminator. Constitutive promoters are classified as providing for a range of constitutive expression. Thus, some are weak constitutive promoters and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level" or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980)

*Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) METHODS IN YEAST GENETICS, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection Catalogue of Cell Lines and Hybridomas (7$^{th}$ ed., 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213-38 (1985)).

In addition, the gene for dimerization domain placed in the appropriate plant expression vector can be used to transform plant cells. The polypeptide can then be isolated from plant callus or the transformed cells can be used to regenerate transgenic plants. Such transgenic plants can be harvested and the appropriate tissues (seed or leaves, for example) can be subjected to large scale protein extraction and purification techniques.

Plant Transformation Methods

Numerous methods for introducing foreign genes into plants are known and can be used to insert a dimerization domain polynucleotide into a plant host, including biological and physical plant transformation protocols. See, e.g., Miki, et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch, et al., (1985) *Science* 227:1229-31), electroporation, micro-injection and biolistic bombardment.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606), direct gene transfer (Paszkowski, et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., Direct DNA Transfer into Intact Plant Cells Via Microprojectile Bombardment pp. 197-213 in *Plant Cell, Tissue and Organ Culture, Fundamental Methods* eds. Gamborg and Phillips, Springer-Verlag Berlin Heidelberg N.Y., 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas, (1984) *Nature* (London) 311:763-764; Bytebier, et al., (1987) *Proc. Natl. Acad. Sci. USA* 84:5345-5349 (Liliaceae); De Wet, et al., (1985) In The Experimental Manipulation of Ovule Tissues, ed. G. P. Chapman, et al., pp. 197-209; Longman, N.Y. (pollen); Kaeppler, et al., (1990) *Plant Cell Reports* 9:415-418 and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

Agrobacterium-Mediated Transformation

The most widely utilized method for introducing an expression vector into plants is based on the natural transformation system of *Agrobacterium. A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae and Chenopodiaceae. Monocot plants can now be transformed with some success. EP Application Number 604 662 A1 discloses a method for transforming monocots using *Agrobacterium*. EP Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) in *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Increasing the Activity and/or Level of a Dimerization Domain Polypeptide

Methods are provided to increase the activity and/or level of the dimerization domain polypeptide. An increase in the level and/or activity of the dimerization domain polypeptide can be achieved by providing to the plant a dimerization domain polypeptide. The dimerization domain polypeptide can be provided by introducing the amino acid sequence encoding the dimerization domain polypeptide into the plant, introducing into the plant a nucleotide sequence encoding a dimerization domain polypeptide or alternatively by selecting for different variants of the genomic locus encoding the dimerization domain polypeptide of the invention.

As discussed elsewhere herein, many methods are known in the art for providing a polypeptide to a plant including, but not limited to, direct introduction of the polypeptide into the plant, introducing into the plant (transiently or stably) a polynucleotide construct encoding a polypeptide having dimerization domain component stack which directs plant development activity. It is also recognized that the methods of the invention may employ a polynucleotide that is not capable of directing, in the transformed plant, the expression of a protein or an RNA. Thus, the level and/or activity of a dimerization domain polypeptide may be increased by altering the gene encoding the dimerization domain polypeptide or its promoter. See, e.g., Kmiec, U.S. Pat. No. 5,565,350; Zarling, et al., PCT/US93/03868. Therefore mutagenized plants that carry mutations in dimerization domain genes, where the mutations increase expression of the dimerization domain gene or increase the plant growth and/or dimerization domain activity of the encoded dimerization domain polypeptide are provided.

Reducing the Activity and/or Level of a Dimerization Domain Polypeptide

Methods are provided to reduce or eliminate the activity of a dimerization domain polypeptide of the invention by transforming a plant cell with an expression cassette that expresses a polynucleotide that inhibits the expression of the dimerization domain polypeptide. The polynucleotide may inhibit the expression of the dimerization domain polypeptide directly, by preventing translation of the dimerization domain messenger RNA, or indirectly, by encoding a polypeptide that inhibits the transcription or translation of a dimerization domain gene encoding a dimerization domain polypeptide. Methods for inhibiting or eliminating the expression of a gene in a plant are well known in the art, and any such method may be used in the present invention to inhibit the expression of a dimerization domain polypeptide.

The expression of a target polypeptide is inhibited if the protein level of the polypeptide is less than 70% of the protein level of the polypeptide in a plant that has not been genetically modified or mutagenized to inhibit the expression of that dimerization domain polypeptide. In particular embodiments of the invention, the protein level of the dimerization domain polypeptide in a modified plant according to the invention is less than 60%, less than 50%, less than 40%, less than 30%, less than 20%, less than 10%, less than 5% or less than 2% of the protein level of the same dimerization domain polypeptide in a plant that is not a mutant or that has not been genetically modified to inhibit the expression of that dimerization domain polypeptide. The expression level of the dimerization domain polypeptide may be measured directly, for example, by assaying for the level of dimerization domain polypeptide expressed in the plant cell or plant, or indirectly, for example, by measuring the plant growth and/or dimerization domain activity of the dimerization domain polypeptide in the plant cell or plant, or by measuring the biomass in the plant. Methods for performing such assays are described elsewhere herein.

In other embodiments of the invention, the activity of the dimerization domain polypeptides is reduced or eliminated by transforming a plant cell with an expression cassette comprising a polynucleotide encoding a polypeptide that inhibits the activity of a dimerization domain polypeptide. The plant growth and/or dimerization domain activity of a dimerization domain component stack polypeptide is inhibited according to the present invention if the plant growth and/or dimerization domain activity of the dimerization domain component stack polypeptide is less than 70% of the plant growth and/or dimerization domain activity of the same dimerization domain polypeptide in a plant that has not been modified to inhibit the plant growth and/or dimerization domain activity of that dimerization domain component stack polypeptide. In particular embodiments of the invention, the plant growth and/or dimerization domain activity of the dimerization domain polypeptide in a modified plant according to the invention is less than 60%, less than 50%, less than 40%, less than 30%, less than 20%, less than 10% or less than 5% of the plant growth and/or dimerization domain activity of the same dimerization domain polypeptide in a plant that that has not been modified to inhibit the expression of that dimerization domain polypeptide. The plant growth and/or dimerization domain activity of a dimerization domain polypeptide is "eliminated" according to the invention when it is not detectable by the assay methods described elsewhere herein. Methods of determining the plant growth and/or dimerization domain activity of a dimerization domain polypeptide are described elsewhere herein.

In other embodiments, the activity of a dimerization domain component stack polypeptide may be reduced or eliminated by disrupting the gene encoding the dimerization domain polypeptide. The invention encompasses mutagenized plants that carry mutations in dimerization domain genes, where the mutations reduce expression of the dimerization domain gene or inhibit the plant growth and/or dimerization domain activity of the encoded dimerization domain polypeptide.

Thus, many methods may be used to reduce or eliminate the activity of a dimerization domain polypeptide. In addition, more than one method may be used to reduce the activity of a single dimerization domain polypeptide. Non-limiting examples of methods of reducing or eliminating the expression of dimerization domain polypeptides are given below.

1. Polynucleotide-Based Methods:

In some embodiments of the present invention, a plant is transformed with an expression cassette that is capable of expressing a polynucleotide that inhibits the expression of a dimerization domain polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one dimerization domain polypeptide is an expression cassette capable of producing an RNA molecule that inhibits the transcription and/or translation of at least one dimerization domain polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a dimerization domain polypeptide are given below.

i. Sense Suppression/Cosuppression

In some embodiments of the invention, inhibition of the expression of a dimerization domain polypeptide may be obtained by sense suppression or cosuppression. For cosuppression, an expression cassette is designed to express an RNA molecule corresponding to all or part of a messenger RNA encoding a dimerization domain polypeptide in the "sense" orientation. Over expression of the RNA molecule can result in reduced expression of the native gene. Accordingly, multiple plant lines transformed with the cosuppression expression cassette are screened to identify those that show the greatest inhibition of dimerization domain polypeptide expression.

The polynucleotide used for cosuppression may correspond to all or part of the sequence encoding the dimerization domain polypeptide, all or part of the 5' and/or 3' untranslated region of a dimerization domain polypeptide transcript or all or part of both the coding sequence and the untranslated regions of a transcript encoding a dimerization domain polypeptide. In some embodiments where the polynucleotide comprises all or part of the coding region for the dimerization domain polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) Plant Cell 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) Proc. Natl. Acad. Sci. USA 91:3490-3496; Jorgensen, et al., (1996) Plant Mol. Biol. 31:957-973; Johansen and Carrington, (2001) Plant Physiol. 126:930-938; Broin, et al., (2002) Plant Cell 14:1417-1432; Stoutjesdijk, et al., (2002) Plant Physiol. 129:1723-1731; Yu, et al., (2003) Phytochemistry 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the invention, inhibition of the expression of the dimerization domain polypeptide may be obtained by antisense suppression. For antisense suppression, the expression cassette is designed to express an RNA molecule complementary to all or part of a messenger RNA encoding the dimerization domain polypeptide. Over expression of the antisense RNA molecule can result in reduced expression of the native gene. Accordingly, multiple plant lines transformed with the antisense suppression expression cassette are screened to identify those that show the greatest inhibition of dimerization domain polypeptide expression.

The polynucleotide for use in antisense suppression may correspond to all or part of the complement of the sequence encoding the dimerization domain polypeptide, all or part of the complement of the 5' and/or 3' untranslated region of the dimerization domain transcript or all or part of the complement of both the coding sequence and the untranslated regions of a transcript encoding the dimerization domain polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of a dimerization domain polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of dimerization domain polypeptide expression. Methods for using dsRNA interference to inhibit the expression of endogenous plant genes are described in Waterhouse, et al., (1998) Proc. Natl. Acad. Sci. USA 95:13959-13964, Liu, et al., (2002) Plant Physiol. 129: 1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of one or a dimerization domain polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the dimerization domain polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the dimerization domain polypeptide. Thus, the polynucleotide causes the degradation of the endogenous messenger RNA, resulting in reduced expression of the dimerization domain polypeptide. This method is described, for example, in U.S. Pat. No. 4,987,071, herein incorporated by reference.

vii. Small Interfering RNA or Micro RNA

In some embodiments of the invention, inhibition of the expression of a dimerization domain polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of dimerization domain expression, the 22-nucleotide sequence is selected from a dimerization domain transcript sequence and contains 22 nucleotide of said dimerization domain sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a dimerization domain polypeptide, resulting in reduced expression of the gene. In particular embodiments, the zinc finger protein binds to a regulatory region of a dimerization domain gene. In other embodiments, the zinc finger protein binds to a messenger RNA encoding a dimerization domain polypeptide and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one dimerization domain polypeptide and reduces the dimerization domain activity of the dimerization domain polypeptide. In another embodiment, the binding of the antibody results in increased turnover of the antibody-dimerization domain complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a dimerization domain polypeptide is reduced or eliminated by disrupting the gene encoding the dimerization domain polypeptide. The gene encoding the dimerization domain polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced dimerization domain activity.

i. Transposon Tagging

In one embodiment of the invention, transposon tagging is used to reduce or eliminate the dimerization domain activity of one or more dimerization domain polypeptide. Transposon tagging comprises inserting a transposon within an endogenous dimerization domain gene to reduce or eliminate expression of the dimerization domain polypeptide. "dimerization domain gene" is intended to mean the gene that encodes a dimerization domain polypeptide according to the invention.

In this embodiment, the expression of one or more dimerization domain polypeptide is reduced or eliminated by inserting a transposon within a regulatory region or coding region of the gene encoding the dimerization domain polypeptide. A transposon that is within an exon, intron, 5' or 3' untranslated sequence, a promoter or any other regulatory sequence of a dimerization domain gene may be used to reduce or eliminate the expression and/or activity of the encoded dimerization domain polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (dimerization domain activity) of the encoded protein are well known in the art. Insertional mutations in gene exons usually result in null-mutants. Mutations in conserved residues are particularly effective in inhibiting the dimerization domain activity of the encoded protein. Conserved residues of plant dimerization domain polypeptides suitable for mutagenesis with the goal to eliminate dimerization domain activity have been described. Such mutants can be isolated according to well-known procedures and mutations in different dimerization domain loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more dimerization domain polypeptide. Examples of other methods for altering or mutating a genomic nucleotide sequence in a plant are known in the art and include, but are not limited to, the use of RNA:DNA vectors, RNA:DNA mutational vectors, RNA: DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

iii. Modulating Plant Growth and/or Dimerization Domain Component Stack Activity In specific methods, the level and/or activity of a dimerization domain gene in a plant is increased by increasing the level or activity of the dimerization domain polypeptide in the plant. Methods for increasing the level and/or activity of dimerization domain polypeptides in a plant are discussed elsewhere herein. Briefly, such methods comprise providing a dimerization domain polypeptide of the invention to a plant and thereby increasing the level and/or activity of the dimerization domain polypeptide. In other embodiments, a dimerization domain nucleotide sequence encoding a dimerization domain polypeptide can be provided by introducing into the plant a polynucleotide comprising a dimerization domain nucleotide sequence of the invention, expressing the dimerization domain sequence, increasing the activity of the dimerization domain polypeptide and thereby increasing the dimerization domain activity and therefore the tissue growth in the plant or plant part. In other embodiments, the dimerization domain nucleotide construct introduced into the plant is stably incorporated into the genome of the plant.

In other methods, the number of cells and biomass of a plant tissue is increased by increasing the level and/or activity of the dimerization domain polypeptide in the plant. Such methods are disclosed in detail elsewhere herein. In one such method, a dimerization domain nucleotide sequence is introduced into the plant and expression of said dimerization domain nucleotide sequence decreases the activity of the dimerization domain polypeptide and thereby increasing the plant growth and/or dimerization domain in the plant or plant part. In other embodiments, the dimerization domain nucleotide construct introduced into the plant is stably incorporated into the genome of the plant.

As discussed above, one of skill will recognize the appropriate promoter to use to modulate the level/activity of a plant growth and/or dimerization domain polynucleotide and polypeptide in the plant. Exemplary promoters for this embodiment have been disclosed elsewhere herein.

Accordingly, the present invention further provides plants having a modified plant growth and/or dimerization domain when compared to the plant growth and/or dimerization domain of a control plant tissue. In one embodiment, the plant of the invention has an increased level/activity of the dimerization domain polypeptide of the invention and thus has increased plant growth and/or dimerization domain in the plant tissue. In other embodiments, the plant of the invention has a reduced or eliminated level of the dimerization domain polypeptide of the invention and thus has decreased plant growth and/or dimerization domain in the plant tissue. In other embodiments, such plants have stably incorporated into their genome a nucleic acid molecule comprising a dimerization domain nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion. In particular, the most desirable outcome would be a root with a stronger vasculature that improves the standability of the plant and thus reduces root lodging as well as being less susceptible to pests.

Methods for modulating root development in a plant are provided. The methods comprise modulating the level and/or activity of the dimerization domain polypeptide in the plant. In one method, a dimerization domain sequence of the invention is provided to the plant. In another method, the dimerization domain nucleotide sequence is provided by introducing into the plant a polynucleotide comprising a dimerization domain nucleotide sequence of the invention, expressing the dimerization domain sequence and thereby modifying root development. In still other methods, the dimerization domain nucleotide construct introduced into the plant is stably incorporated into the genome of the plant.

In other methods, root development is modulated by altering the level or activity of the dimerization domain polypeptide in the plant. An increase in dimerization domain activity can result in at least one or more of the following alterations to root development, including, but not limited to, larger root meristems, increased in root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by increasing the activity and/or level of the dimerization domain polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by increasing the level and/or activity of the dimerization domain polypeptide also finds use in promoting in vitro propagation of explants.

Furthermore, higher root biomass production due to an increased level and/or activity of dimerization domain activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the dimerization domain polypeptide of the invention and has enhanced root growth and/or root biomass. In other embodiments, such plants have stably incorporated into their genome a nucleic acid molecule comprising a dimerization domain nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a dimerization domain polypeptide of the invention. In one embodiment, a dimerization domain sequence of the invention is provided. In other embodiments, the dimerization domain nucleotide sequence can be provided by introducing into the plant a polynucleotide comprising a dimerization domain nucleotide sequence of the invention, expressing the dimerization domain sequence and thereby modifying shoot and/or leaf development. In other embodiments, the dimerization domain nucleotide construct introduced into the plant is stably incorporated into the genome of the plant.

In specific embodiments, shoot or leaf development is modulated by decreasing the level and/or activity of the dimerization domain polypeptide in the plant. An decrease in dimerization domain activity can result in at least one or more of the following alterations in shoot and/or leaf development, including, but not limited to, reduced leaf number, reduced leaf surface, reduced vascular, shorter internodes and stunted growth and retarded leaf senescence when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

Decreasing dimerization domain activity and/or level in a plant results in shorter internodes and stunted growth. Thus, the methods of the invention find use in producing dwarf plants. In addition, as discussed above, modulation of dimerization domain activity in the plant modulates both root and shoot growth. Thus, the present invention further provides methods for altering the root/shoot ratio. Shoot or leaf development can further be modulated by decreasing the level and/or activity of the dimerization domain polypeptide in the plant.

Accordingly, the present invention further provides plants having modulated shoot and/or leaf development when compared to a control plant. In some embodiments, the plant of the invention has an increased level/activity of the dimerization domain polypeptide of the invention, altering the shoot and/or leaf development. Such alterations include, but are not limited to, increased leaf number, increased leaf surface, increased vascularity, longer internodes and increased plant stature, as well as alterations in leaf senescence, as compared to a control plant. In other embodiments, the plant of the invention has a decreased level/activity of the dimerization domain polypeptide of the invention.

vi Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the dimerization domain polypeptide has not been modulated. "Modulating floral development" further includes any alteration in the timing of the development of a plant's reproductive tissue (i.e., a delayed or an accelerated timing of floral development) when compared to a control plant in which the activity or level of the dimerization domain polypeptide has not been modulated. Macroscopic alterations may include changes in size, shape, number or location of reproductive tissues, the developmental time period that these structures form or the ability to maintain or proceed through the flowering process in times of environmental stress. Microscopic alterations may include changes to the types or shapes of cells that make up the reproductive tissues.

The method for modulating floral development in a plant comprises modulating dimerization domain activity in a plant. In one method, a dimerization domain sequence of the invention is provided. A dimerization domain nucleotide sequence can be provided by introducing into the plant a polynucleotide comprising a dimerization domain nucleotide sequence of the invention, expressing the dimerization domain sequence and thereby modifying floral development. In other embodiments, the dimerization domain nucleotide construct introduced into the plant is stably incorporated into the genome of the plant.

In specific methods, floral development is modulated by decreasing the level or activity of the dimerization domain polypeptide in the plant. A decrease in dimerization domain activity can result in at least one or more of the following alterations in floral development, including, but not limited to, retarded flowering, reduced number of flowers, partial male sterility and reduced seed set when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

In other methods, floral development is modulated by increasing the level and/or activity of the dimerization domain sequence of the invention. Such methods can comprise introducing a dimerization domain nucleotide sequence into the plant and increasing the activity of the dimerization domain polypeptide. In other methods, the dimerization domain nucleotide construct introduced into the plant is stably incorporated into the genome of the plant. Increasing expression of the dimerization domain sequence of the invention can modulate floral development during periods of stress. Such methods are described elsewhere herein. Accordingly, the present invention further provides plants having modulated floral development when compared to the floral development of a control plant. Compositions include plants having an increased level/activity of the dimerization domain polypeptide of the invention and having an altered floral development. Compositions also include plants having an increased level/activity of the dimerization domain polypeptide of the invention wherein the plant maintains or proceeds through the flowering process in times of stress.

Methods are also provided for the use of the dimerization domain of the invention to increase seed size and/or weight. The method comprises increasing the activity of the dimerization domain in a plant or plant part, such as the seed. An increase in seed size and/or weight comprises an increased size or weight of the seed and/or an increase in the size or weight of one or more seed part including, for example, the embryo, endosperm, seed coat, aleurone or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters and endosperm-preferred promoters.

The method for decreasing seed size and/or seed weight in a plant comprises decreasing dimerization domain activity in the plant. In one embodiment, the dimerization domain nucleotide sequence can be provided by introducing into the plant a polynucleotide comprising a dimerization domain nucleotide sequence of the invention, expressing the dimerization domain sequence and thereby increasing seed weight and/or size. In other embodiments, the dimerization domain nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has an increased level/activity of the dimerization domain polypeptide of the invention and has an increased seed weight and/or seed size. In other embodiments, such plants have stably incorporated into their genome a nucleic acid molecule comprising a dimerization domain nucleotide sequence of the invention operably linked to a promoter that drives expression in the plant cell.

vii. Method of Use for Dimerization Domain Promoter Polynucleotides

The polynucleotides comprising the dimerization domain promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the dimerization domain promoter polynucleotides of the invention are provided in expression cassettes along with a polynucleotide sequence of interest for expression in the host cell of interest. The dimerization domain promoter sequences of the invention are expressed in a variety of tissues containing cells that have dimerization domain and thus the promoter sequences can find use in regulating the temporal and/or the spatial expression of polynucleotides of interest particularly in the dimerization domain containing cells.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the dimerization domain promoter sequences of the invention or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) Curr. Opin. Plant Biol. 1:311-315. Alternatively, a synthetic dimerization domain promoter sequence may comprise duplications of the upstream promoter elements found within the dimerization domain promoter sequences.

It is recognized that the promoter sequence of the invention may be used with its native dimerization domain coding sequences. A DNA construct comprising the dimerization domain promoter operably linked with its native dimerization domain gene may be used to transform any plant of interest to bring about a desired phenotypic change, such as modulating cell number, modulating root, shoot, leaf, floral and embryo development, stress tolerance and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,409); barley high lysine (Williamson, et al., (1987) Eur. J. Biochem. 165: 99-106 and WO 98/20122) and high methionine proteins (Pedersen, et al., (1986) J. Biol. Chem. 261:6279; Kirihara, et al., (1988) Gene 71:359 and Musumura, et al., (1989) Plant Mol. Biol. 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., Bacillus thuringiensis toxic proteins (U.S. Pat. Nos. 5,366, 892; 5,747,450; 5,737,514; 5723,756; 5,593,881; Geiser, et al., (1986) Gene 48:109); lectins (Van Damme, et al., (1994) Plant Mol. Biol. 24:825); fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase and acetoacetyl-CoA reductase (Schubert, et al., (1988) J. Bacteriol. 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch and protein content can be genetically altered in addition to using traditional breeding methods. Modifications include increasing content of oleic acid, saturated and unsaturated oils, increasing levels of lysine and sulfur, providing essential amino acids and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016 and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996 and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359, both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109), and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089), and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that inhibit enol-pyruvylshikimate phosphate synthase (EPSPS), e.g., glyphosate acetyl transferase (GAT), genes coding for resistance to herbicides that act to inhibit action of glutamine synthase, such as phosphinothricin or basta (e.g., the bar gene), a combination thereof or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Yield and Harvest Index Tests—RT810ZBS_T (Intro-EF09B/GR1B5)

PHP26963 (S2a:D8MPL+S2a:CesA10)—10 evts
PHP26998 (S2a:D8mpl+Nas2:DD+S2a:CesA10)—8 evts
PHP24843 (S2a:D8MPL+NAS2:DD)—4 evts
Construct Nulls (3 events/null)
WT (Intro-EF09BZTZ/GR1B5)
2 Densities
36,000 PPA (JH, MR)—Yield (5 reps)
48,000 PPA (JH, MR)—Yield (5 reps), Harvest Index (3 reps)

Three constructs were tested at Johnston (JH) and Marion (MR) Iowa at two densities, 36,000 plants per acre (PPA) and 48,000 PPA in 20" row width. The genes tested consisted of the dwarf mutant D8mpl and the additional genes (stacks) DD (dimerization domain of the D8 gene) or the Ces A10 gene. The constructs are shown below in which the transgenic events are shown with their plasmid identification and nulls (segregating non transgenic sibs) are shown with their plasmid designation and the letter n.

TABLE 2

| D8mpl + DD | php24843 | E7216.51.1.1 |
|---|---|---|
|  | php24843n | E7216.49.1.5 |
| D8 + CesA | php26963 | E7216.49.2.1 |
|  | php26963 | E7216.49.2.2 |
|  | php26963 | E7216.49.3.1 |
|  | php26963n | CN |
| D8 + DD + CesA | php26998 | E7216.50.1.1 |
|  | php26998 | E7216.50.1.3 |
|  | php26998n | CN |

A higher plant population density was chosen to determine if the dwarf and dwarf stack transgenic plants behaved the same or differently than the construct null sibs (no transgenes with normal height) for yield and harvest index. In general, corn shows a decline in yield in populations above the optimum economic yield such that yield levels decline. Harvest index in corn has been relatively stable, from 45 to 50% as defined by ear dry matter/total above ground dry matter. Increases in biomass and harvest index are the major determinants of yield, thus a positive change in either attribute could lead to higher potential yield.

The yield comparison for selected events of the different constructs at the Johnston and Marion locations was performed. In general, the reduction in yield levels due to high plant population was more pronounced in the null sibs compared to the respective transgenic stack constructs. In some instances, the transgenic treatments showed an unexpected and increased yield response, particularly in the Marion, Iowa location. Such an observation indicates that further breeding with a variety of different germplasm sources in addition to those used with these transgene stacks or additional optimization of the agronomic factors such as row width, fertilization practices or optimized plant population for the dwarf phenotype would further improve yield potential.

Harvest index of the entries at the higher population density of 48,000 PPA was measured. Generally, the harvest index of the null sibs were just between 0.5 and 0.52 while most of the transgenic stacks had a harvest index in the range of 0.54 to 0.58. The increase in harvest index could be expected to make better use of available soil moisture and nutrients since a greater proportion of the dry matter produced is in the form of grain.

Example 2

Yield and Harvest Index Tests—(Intro-EF09B/HG11)

Topcrosses were made from PHP26963, PHP26998 and PHP24843 T0 plants onto HG11 females. This produced a background genotype similar to commercial hybrid 33A14 which could be used as a reference. These plants were then grown in Johnston observation plots. A small planting of PHP17881 hybrids were also included.

Figure 2:
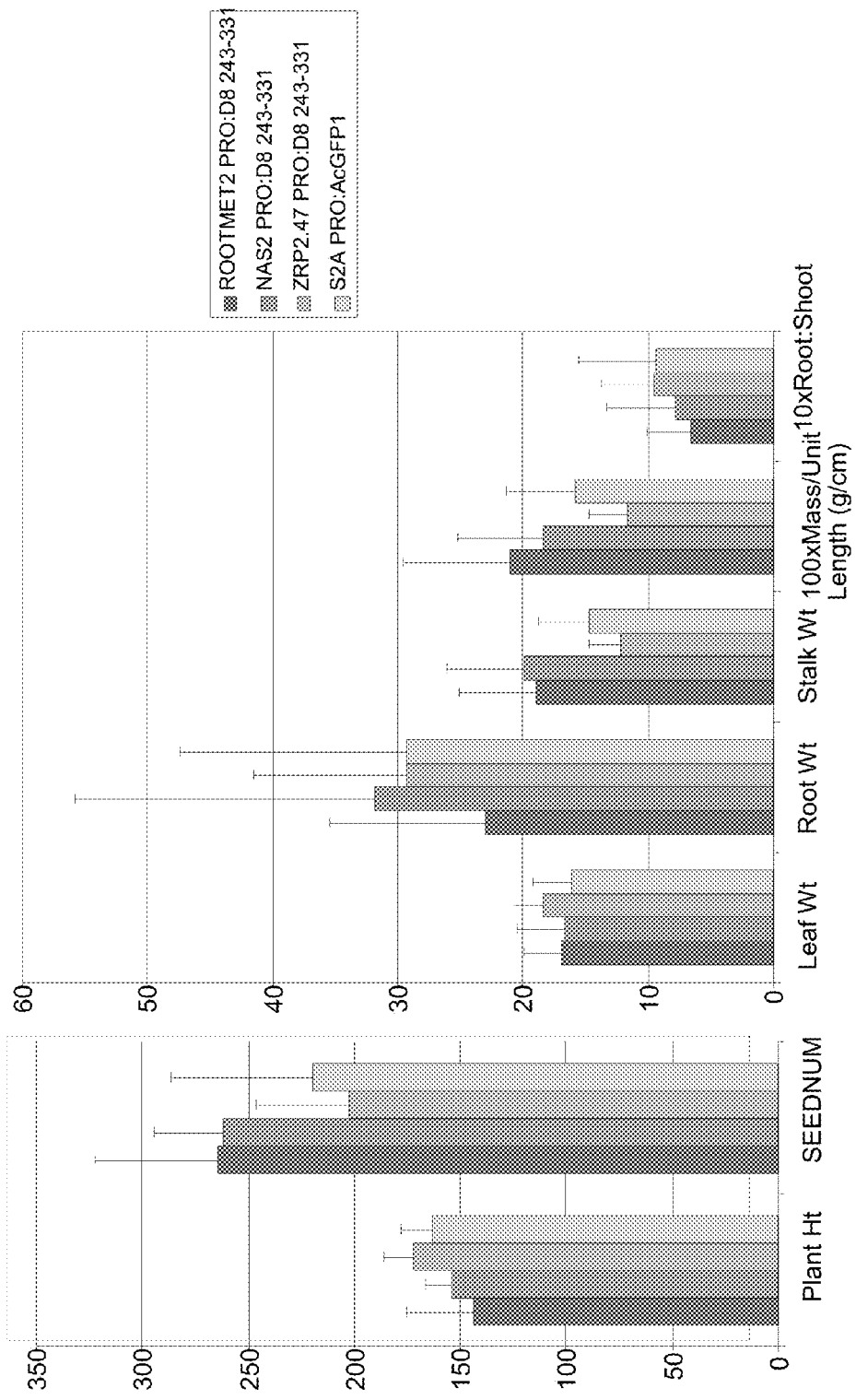
FIG. 2: D8-MPL Stack Average Harvest Index by construct, based on late season plant dry weight.
Figure 3:
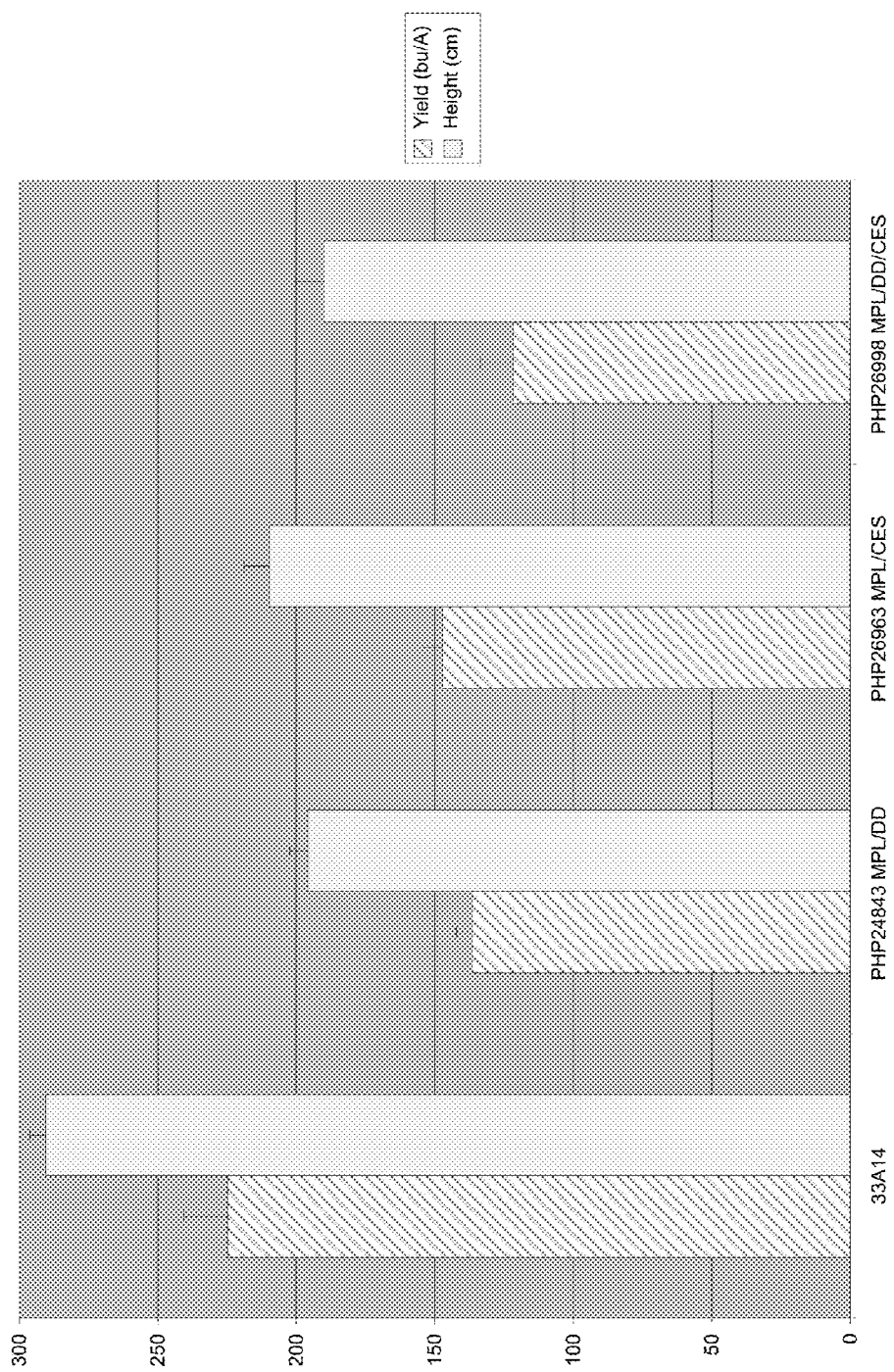
FIG. 3: D8-MPL Stack Yield Comparison at 24K
Figure 4:
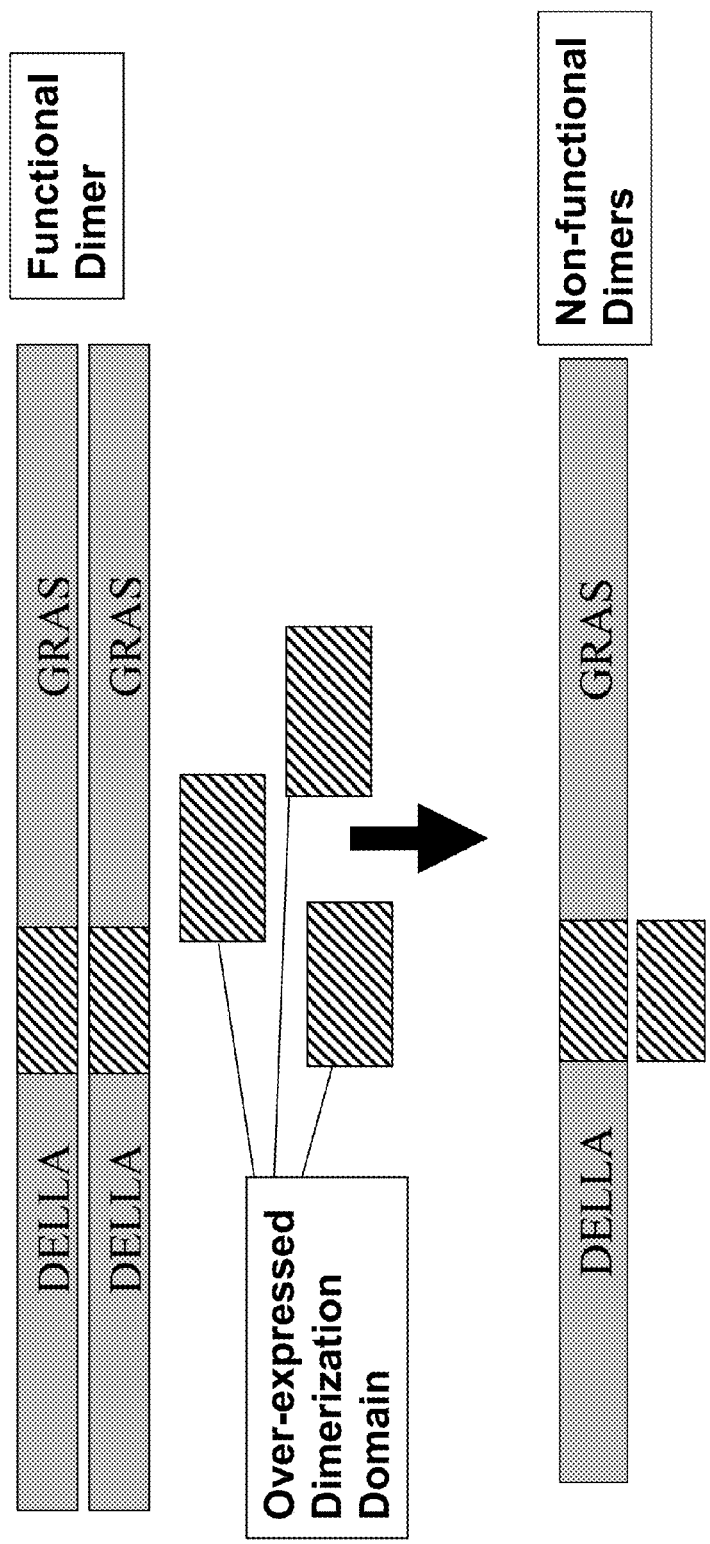
FIG. 4: Diagram describing selective architecture modification of Zm-D8 243-331, a dominant negative transgene, overexpression of DD, leading to non-functional dimers. Non-functional Dimers (DN) increase elongation when expressed in tissues such as roots, ears or tassels.

PHP26963 (S2a:D8MPL+S2a:CesA10)—2 evts, 6 rows
PHP26998 (S2a:D8mpl+Nas2:DD+S2a:CesA10)—2 evts, 6 rows
PHP24843 (S2a:D8MPL+NAS2:DD)—2 evts, 8 rows
PHP17881 (S2a:D8MPL)
WT (EF09B/HG11-33A14)—11 rows Minirhizotron tubes were inserted in the soil near these plants to allow for imaging of roots that intersected the tubes. This allowed for a direct measurement of root length of the NAS2:DD stack constructs (FIGS. 2-5). The DD stacks had longer root systems at earlier time points and appeared to be colonizing the soil more rapidly than the non DD counterparts. The later time point showed the non-DD constructs having similar root lengths to the DD stacks at more shallow depths, but not yet fully colonizing the lowest depth of soil measured. The surface area of these plants increased proportionately with the length, indicating that there is no sacrifice of root width. Plant height and yields were consistent with previous observations of S2a:D8MPL constructs (FIG. 4 and Table 3—Heights from field experiments).

TABLE 3

|  | Average Height (m) | Standard Deviation (m) |
|---|---|---|
| 33A14 | 2.90 | 0.06 |
| PHP17881 (D8 MPL) | 1.99 | 0.28 |
| PHP24843 (D8/DD) | 1.96 | 0.06 |
| PHP26963 (D8/CES) | 2.10 | 0.09 |
| PHP26998 (D8/DD/CES) | 1.90 | 0.10 |

Example 3

Greenhouse Grown Transgenic Stacks

Three constructs were tested in the introEF09B background at the T0 generation to determine the agronomic characteristics of the D8 dimerization domain stacks and for preparation for field testing. Each stacked construct (PHP24843, PHP26963 and PHP26998) utilized the S2A PRO:D8MPL gene, NAS2 PRO:D8 243-331 and/or S2A PRO:ZM-CES A10.

Genes Tested (Intro EF09B)
S2a:D8MPL (Vascular Element Preferred Promoter:moderate dwarfing Gene)
Nas2:DD (Root Preferred Promoter: Leucine Zipper Dimerization Domain)
S2a:CesA10 (Vascular Element Preferred Promoter:Cellulose Synthase Gene in Stalk Tissue.
Gene Combinations ("Stacks") of Two and Three Genes
PHP24843—NAS2 PRO:D8 243-331/S2A PRO:D8MPL Stack (13 events)
PHP26963—S2A PRO:ZM-CES A10/S2A PRO:D8MPL Stack (15 events)
PHP26998—NAS2 PRO:D8 243-331/S2A PRO:ZM-CES A10/S2A PRO:D8MPL (14 events)

Morphometric analyses were performed on the mature T0 plants from this experiment (FIG. 6). The NAS2 PRO:D8 243-331 gene increased leaf width and area in this experiment. The S2A PRO:ZM-CES A10 gene increased leaf angle, decreased leaf length and increased seed number.

Example 4

Greenhouse Grown Transgenic Stacks

Five constructs were tested in GS3×GF3 at the T0 generation to determine the effectiveness of the D8 dimerization domain for reversing dwarfing of the maize root system. Each stacked construct (PHP24843, PHP24844 and PHP24861) utilized a different root preferred promoter to drive expression the D8 243-331 coding sequence.

Genes Tested (GS3×GF#)
S2a:D8MPL (Vascular Element Preferred Promoter:moderate dwarfing Gene)
Nas2:DD (Root Preferred Promoter: Leucine Zipper Dimerization Domain)
ZRP2.47 PRO:D8 243-331 (Root Preferred Promoter: Leucine Zipper Dimerization Domain)
ROOTMET2 PRO:D8 243-331 (Root Preferred Promoter: Leucine Zipper Dimerization Domain)
ROOTMET2 PRO:GUSINT (Root Preferred Promoter: β-glucuronidase reporter gene)
Gene Combinations ("Stacks") of Two Genes
PHP24843—NAS2 PRO:D8 243-331/S2A PRO:D8MPL Stack (25 events)
PHP24844—ZRP2.47 PRO:D8 243-331/S2A PRO: D8MPL Stack (23 events)
PHP24861—ROOTMET2 PRO:D8 243-331/S2A PRO: D8MPL Stack (22 events)
PHP17881—S2A PRO:D8MPL (Dwarf Control) (14 events)
PHP23206—ROOTMET2 PRO:GUSINT (Full Size Control) (14 events)

Morphometric analyses were performed on the mature T0 plants from this experiment (FIG. 7). The findings were that root weight was not significantly altered. The expected root change is in root length, which could not be measured due to root bound growth in greenhouse pots. Each construct with the S2A PRO:D8MPL gene displayed a reduced stature with plant height reduced by ~25-35%. Stalk weight was lower in the dimerization domain constructs than in the S2A PRO: D8MPL alone, which was in-turn lower than the full size control. Leaf weight and seed number were reduced in PHP24844, PHP24861 and PHP17881 compared to the full size control; however, PHP24843 (NAS2 PRO:D8 243-331/ S2A PRO:D8MPL Stack) retained leaf weight and seed numbers equal to those of the full size control. Seed number is a component of yield and stalk weight is a component of biomass, indicating that PHP24843 may increase harvest index.

Example 5

Greenhouse Grown D8 Dimerization Domain Transgenics

Four constructs were tested in GS3×GF3 at the T0 generation to determine the effects of the D8 dimerization domain when expressed in roots in a non-stacked configuration. Each stacked construct (PHP24711, PHP24712 and PHP24713) utilized a different root preferred promoter to drive expression the D8 243-331 coding sequence.

Genes Tested (GS3×GF#)
Nas2:DD (Root Preferred Promoter: Leucine Zipper Dimerization Domain)
ZRP2.47 PRO:D8 243-331 (Root Preferred Promoter: Leucine Zipper Dimerization Domain)
ROOTMET2 PRO:D8 243-331 (Root Preferred Promoter: Leucine Zipper Dimerization Domain)
Gene Constructs
PHP24711—ZRP2.47 PRO:D8 243-331 (25 events)
PHP24712—ROOTMET2 PRO:D8 243-331 (25 events)
PHP24713—NAS2 PRO:D8 243-331 (25 events)
PHP24715—S2A PRO:AC-GFP1 (Full Size Control) (25 events)

Morphometric analyses were performed on the mature T0 plants from this experiment (FIG. 8). Stalk weight and seed number were increased in the ROOTMET2 PRO:D8 243-331 and NAS2 PRO:D8 243-331 constructs.

Example 6

Two Location, 3 Construct, Yield and Harvest Index Trial

Yield and harvest index comparisons were made with three different constructs in genotype "Intro EF09B/GR1B5" compared to their respective construct nulls. The data is described in Table 4. The yield and harvest index was measured in replicated experiments (5) at 48,000 PPA seeded in 20" rows in Johnston and Marion Iowa using a randomized complete block design. Generally, the semi-dwarf plant height was approximately 60-70% of the construct nulls (CN) with each construct. The phP29693 and phP26998 plant height was about 65% (about 12" taller) than phP24843. Compared to the construct nulls, yield in Johnston was near equal to the construct null with the events shown in this table. Harvest index was significantly higher in the Johnston location. At the Marion location, several constructs/events were higher in yield than their respective construct nulls. Harvest index was numerically higher and in most cases significantly higher than their respective construct nulls. The semi-dwarf transgenics had a better yield response at high populations compared to the construct nulls when grown at a lower population of 36,000 ppa. The 'stacked' combinations of D8mpl+DD was not significantly lower than the construct null for yield but had higher harvest index at both locations. The combination in construct phP26963 had higher yield potential in Johnston and Marion with higher harvest index. The combination of D8mpl+DD+CesA 10 had similar or equal yield and higher harvest index in Johnston while the triple gene stack in the Marion, Iowa location shows lower yields but higher harvest index. Although there were some individual plots that showed root and stalk lodging, neither location had significant differences between the transgenic and their construct nulls.

TABLE 4

| Gene | PHP | ID # | JH yield | % of null | JH HI (%) | MR yield | % of null | MR HI (%) |
|---|---|---|---|---|---|---|---|---|
| D8mpl/DD | control | E7216.51.1.1 | 168 | 95% | 0.57 (110) | 152 | 98% | 0.56 (103) |
| | | CN | 177 | | 0.51 | 156 | | 0.54 |
| D8/CesA | 26963 | E7216.49.1.5 | 163 | 92 | 0.58 (114) | 141 | 105% | 0.54 (111) |
| | | E7216.49.2.1 | 172 | 97% | 0.56 (111) | 147 | 110% | 0.58 (112) |
| | | E7216.49.2.2 | 176 | 100% | 0.56 (111) | 152 | 113% | 0.53 (104) |
| | | E7216.49.3.1 | 176 | 99% | 0.53 (104) | 151 | 113% | 0.55 (108) |
| | | CN | 177 | | 0.51 | 134 | | 0.51 |

TABLE 4-continued

| Gene | PHP | ID # | JH yield | % of null | JH HI (%) | MR yield | % of null | MR HI (%) |
|---|---|---|---|---|---|---|---|---|
| D8/DD/CesA | 26998 | E7216.50.1.1 | 158 | 93% | 0.56 (109) | 133 | 90% | 0.58 (113) |
| | | E7216.50.1.3 | 168 | 99% | 0.57 (110) | 133 | 90% | 0.54 (104) |
| | | CN | 169 | | 0.51 | 149 | | 0.52 |

JH = Johnston
MR = Marion
HI = Harvest Index

Example 7

Transformation and Regeneration of Transgenic Plants

Immature maize embryos from greenhouse donor plants are bombarded with a plasmid containing the Zm dimerization domain sequence operably linked to the drought-inducible promoter RAB17 promoter (Vilardell, et al., (1990) *Plant Mol Biol* 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox® bleach plus 0.5% Micro detergent for 20 minutes and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the dimerization domain sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite® (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose and 2.0 mg/l 2,4-D (brought to volume with D-I $H_2O$ following adjustment to pH 5.8 with KOH); 3.0 g/l Gelrite® (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite® (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL and 0.40 g/l glycine brought to volume with polished D-I $H_2O$), 0.1 g/l myo-inositol and 40.0 g/l sucrose (brought to volume with polished D-I $H_2O$ after adjusting pH to 5.6)

and 6 g/l Bacto™-agar (added after bringing to volume with polished D-I H$_2$O), sterilized and cooled to 60° C.

Example 8

Agrobacterium-Mediated Transformation

For *Agrobacterium*-mediated transformation of maize with an antisense sequence of the Zmdimerization domain sequence of the present invention, preferably the method of Zhao is employed (U.S. Pat. No. 5,981,840 and PCT Patent Publication WO98/32326, the contents of which are hereby incorporated by reference). Briefly, immature embryos are isolated from maize and the embryos contacted with a suspension of *Agrobacterium*, where the bacteria are capable of transferring the dimerization domain sequence to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants. Plants are monitored and scored for a modulation in meristem development. For instance, alterations of size and appearance of the shoot and floral meristems and/or increased yields of leaves, flowers and/or fruits are monitored.

Example 9

Sugar Cane Transformation

This protocol describes routine conditions for production of transgenic sugarcane lines. The same conditions are close to optimal for number of transiently expressing cells following bombardment into embryogenic sugarcane callus. See also, Bower, et al., (1996). *Molec Breed* 2:239-249; Birch and Bower, (1994). Principles of gene transfer using particle bombardment. In Particle Bombardment Technology for Gene Transfer, Yang and Christou, eds (New York: Oxford University Press), pp. 3-37 and Santosa, et al., (2004), *Molecular Biotechnology* 28:113-119, incorporated herein by reference.

Sugarcane Transformation Protocol:
1. Subculture callus on MSC3, 4 days prior to bombardment:
   (a) Use actively growing embryogenic callus (predominantly globular pro-embryoids rather than more advanced stages of differentiation) for bombardment and through the subsequent selection period.
   (b) Divide callus into pieces around 5 mm in diameter at the time of subculture and use forceps to make a small crater in the agar surface for each transferred callus piece.
   (c) Incubate at 28° C. in the dark, in deep (25 mm) Petri dishes with micropore tape seals for gas exchange.
2. Place embryogenic callus pieces in a circle (~2.5 cm diameter), on MSC3Osm medium. Incubate for 4 hours prior to bombardment.
3. Sterilize 0.7 μm diameter tungsten (Grade M-10, Bio-Rad #165-2266) in absolute ethanol. Vortex the suspension, then pellet the tungsten in a microfuge for ~30 seconds. Draw off the supernatant and resuspend the particles at the same concentration in sterile H$_2$0. Repeat the washing step with sterile H$_2$0 twice and thoroughly resuspend particles before transferring 50 μl aliquots into microfuge tubes.
4. Add the precipitation mix components:

| Component (stock solution) | Volume to add | Final conc in mix |
|---|---|---|
| Tungsten (100 μg/μl in H$_2$O) | 50 μl | 38.5 μg/μl |
| DNA (1 μg/μl) | 10 μl | 0.38 μg/μl |
| CaCl$_2$ (2.5 M in H$_2$0) | 50 μl | 963 mM |
| Spermidine free base (0.1 M in H$_2$0) | 20 μl | 15 mM |

5. Allow the mixture to stand on ice for 5 min. During this time, complete steps 6-8 below.
6. Disinfect the inside of the 'gene gun' target chamber by swabbing with ethanol and allow it to dry.
7. Adjust the outlet pressure at the helium cylinder to the desired bombardment pressure.
8. Adjust the solenoid timer to 0.05 seconds. Pass enough helium to remove air from the supply line (2-3 pulses).
9. After 5 min on ice, remove (and discard) 100 μl of supernatant from the settled precipitation mix.
10. Thoroughly disperse the particles in the remaining solution.
11. Immediately place 4 μl of the dispersed tungsten-DNA preparation in the center of the support screen in a 13 mm plastic syringe filter holder.
12. Attach the filter holder to the helium outlet in the target chamber.
13. Replace the lid over the target tissue with a sterile protective screen. Place the sample into the target chamber, centered 16.5 cm under the particle source and close the door.
14. Open the valve to the vacuum source. When chamber vacuum reaches 28" of mercury, press the button to apply the accelerating gas pulse, which discharges the particles into the target chamber.
15. Close the valve to the vacuum source. Allow air to return slowly into the target chamber through a sterilizing filter. Open the door, cover the sample with a sterile lid and remove the sample dish from the chamber.
16. Repeat steps 10-15 for consecutive target plates using the same precipitation mix, filter and screen.
17. Approximately 4 hours after bombardment, transfer the callus pieces from MSC3Osm to MSC3.
18. Two days after shooting, transfer the callus onto selection medium. During this transfer, divide the callus into pieces ~5 mm in diameter, with each piece being kept separate throughout the selection process.
19. Subculture callus pieces at 2-3 week intervals.
20. When callus pieces grow to ~5 to 10 mm in diameter (typically 8 to 12 weeks after bombardment) transfer onto regeneration medium at 28° C. in the light.
21. When regenerated shoots are 30-60 mm high with several well-developed roots, transfer them into potting mix with the

Example 10

Soybean Embryo Transformation

Soybean embryos are bombarded with a plasmid containing a dimerization domain sequence operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising a dimerization domain sense sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 11

Sunflower Meristem Tissue Transformation

Sunflower meristem tissues are transformed with an expression cassette containing a dimerization domain sequence operably linked to a ubiquitin promoter as follows (see also, EP Patent Number 0 486233, herein incorporated by reference and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween® 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.,* 15:473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6 and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS1000® particle acceleration device.

Disarmed *Agrobacterium tumefaciens* strain EHA105 is used in all transformation experiments. A binary plasmid vector comprising the expression cassette that contains the dimerization domain gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bacto®peptone, and 5 gm/l NaCl, pH 7.0) with the appropriate antibiotics required for bacterial strain and binary plasmid maintenance. The suspension is used when it reaches an OD$_{600}$ of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite®, pH 5.6) and grown under conditions described for explant culture. The upper portion of the seedling is removed, a 1 cm vertical slice is made in the hypocotyl and the transformed shoot inserted into the cut. The entire area is wrapped with Parafilm® to secure the shoot. Grafted plants can be transferred to soil following one week of in vitro culture. Grafts in soil are maintained under high humidity conditions followed by a slow acclimatization to the greenhouse environment. Transformed sectors of T$_0$ plants (parental generation) maturing in the greenhouse are identified by NPTII ELISA and/or by dimerization domain activity analysis of leaf extracts while transgenic seeds harvested from NPTII-positive T$_0$ plants are identified by dimerization domain activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox® bleach solution with the addition of two to three drops of Tween® 20 per 100 ml of solution, then rinsed three times with distilled water. Sterilized seeds are imbibed in the dark at 26° C. for 20 hours on filter paper moistened with water. The cotyledons and root radical are removed and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar) and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bacto®peptone and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l NH$_4$Cl and 0.3 g/l MgSO$_4$ at pH 5.7) to reach a final concentration of 4.0 at OD$_{600}$. Particle-bombarded explants are transferred to GBA medium (374E) and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a change in dimerization domain expression) explants are identified, those shoots that fail to exhibit an alteration in dimerization domain activity are discarded and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for altered dimerization domain expression are grafted to Pioneer hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween® 20 per 100 ml of solution, and are rinsed three times with distilled water. The sterilized seeds are germinated on the filter moistened with water for three days, then they are transferred into 48 medium (half-strength MS salt, 0.5% sucrose, 0.3% Gelrite® pH 5.0) and grown at 26° C. under the dark for three days, then incubated at 16-hour-day culture conditions. The upper portion of selected seedling is removed, a vertical slice is made in each hypocotyl and a transformed shoot is inserted into a V-Cut. The cut area is wrapped with Parafilm®. After one week of culture on the medium, grafted plants are transferred to soil. In the first two weeks, they are maintained under high humidity conditions to acclimatize to a greenhouse environment.

Example 12

*Agrobacterium* Mediated Grass Transformation

Grass plants may be transformed by following the *Agrobacterium* mediated transformation of Luo, et al., (2004) *Plant Cell Rep* (2004) 22:645-652.
Materials and Methods
Plant Material
A commercial cultivar of creeping bentgrass (*Agrostis stolonifera* L., cv. Penn-A-4) supplied by Turf-Seed (Hubbard, Ore.) can be used. Seeds are stored at 4° C. until used.
Bacterial Strains and Plasmids
*Agrobacterium* strains containing one of 3 vectors are used. One vector includes a pUbi-gus/Act1-hyg construct consisting of the maize ubiquitin (ubi) promoter driving an intron-containing b-glucuronidase (GUS) reporter gene and the rice actin 1 promoter driving a hygromycin (hyg) resistance gene. The other two pTAP-arts/35S-bar and pTAP-barnase/Ubi-bar constructs are vectors containing a rice tapetum-specific promoter driving either a rice tapetum-specific antisense gene, rts (Lee, et al., (1996) *Int Rice Res Newsl* 21:2-3) or a ribonuclease gene, barnase (Hartley, (1988) *J Mol Biol* 202:913-915), linked to the cauliflower mosaic virus 35S promoter (CaMV 35S) or the rice ubi promoter (Huq, et al, (1997) *Plant Physiol* 113:305) driving the bar gene for herbicide resistance as the selectable marker.

Induction of Embryogenic Callus and *Agrobacterium*-Mediated Transformation

Mature seeds are dehusked with sand paper and surface sterilized in 10% (v/v) Clorox® bleach (6% sodium hypochlorite) plus 0.2% (v/v) Tween® 20 (Polysorbate 20) with vigorous shaking for 90 min. Following rinsing five times in sterile distilled water, the seeds are placed onto callus-induction medium containing MS basal salts and vitamins (Murashige, and Skoog, (1962) *Physiol Plant* 15:473-497), 30 g/l sucrose, 500 mg/l casein hydrolysate, 6.6 mg/l 3,6-dichloro-o-anisic acid (dicamba), 0.5 mg/l 6-benzylaminopurine (BAP) and 2 g/l Phytagel. The pH of the medium is adjusted to 5.7 before autoclaving at 120° C. for 20 min. The culture plates containing prepared seed explants are kept in the dark at room temperature for 6 weeks. Embryogenic calli are visually selected and subcultured on fresh callus-induction medium in the dark at room temperature for 1 week before co-cultivation.

Transformation

The transformation process is divided into five sequential steps: agro-infection, co-cultivation, antibiotic treatment, selection and plant regeneration. One day prior to agro-infection, the embryogenic callus is divided into 1- to 2-mm pieces and placed on callus-induction medium containing 100 μM acetosyringone. A 10-ml aliquot of *Agrobacterium* suspension (OD=1.0 at 660 nm) is then applied to each piece of callus, followed by 3 days of co-cultivation in the dark at 25° C. For the antibiotic treatment step, the callus is then transferred and cultured for 2 weeks on callus-induction medium plus 125 mg/l cefotaxime and 250 mg/l carbenicillin to suppress bacterial growth. Subsequently, for selection, the callus is moved to callus-induction medium containing 250 mg/l cefotaxime and 10 mg/l phosphinothricin (PPT) or 200 mg/l hygromycin for 8 weeks. Antibiotic treatment and the entire selection process is performed at room temperature in the dark. The subculture interval during selection is typically 3 weeks. For plant regeneration, the PPT- or hygromycin-resistant proliferating callus is first moved to regeneration medium (MS basal medium, 30 g/l sucrose, 100 mg/l myo-inositol, 1 mg/l BAP and 2 g/l Phytagel) supplemented with cefotaxime, PPT or hygromycin. These calli are kept in the dark at room temperature for 1 week and then moved into the light for 2-3 weeks to develop shoots. Small shoots are then separated and transferred to hormone-free regeneration medium containing PPT or hygromycin and cefotaxime to promote root growth while maintaining selection pressure and suppressing any remaining *Agrobacterium* cells. Plantlets with well-developed roots (3-5 weeks) are then transferred to soil and grown either in the greenhouse or in the field.

Staining for GUS Activity

GUS activity in transformed callus is assayed by histochemical staining with 1 mM 5-bromo-4-chloro-3-indolyl-b-d-glucuronic acid (X-Gluc, Biosynth, Staad, Switzerland) as described in Jefferson, (1987) *Plant Mol Biol Rep* 5:387-405. The hygromycin-resistant callus surviving from selection was incubated at 37 C overnight in 100 μl of reaction buffer containing X-Gluc. GUS expression is then documented by photography.

Vernalization and Out-Crossing of Transgenic Plants

Transgenic plants are maintained out of doors in a containment nursery (3-6 months) until the winter solstice in December. The vernalized plants are then transferred to the greenhouse and kept at 25° C. under a 16/8 h [day/light (artificial light)] photoperiod and surrounded by non-transgenic wild-type plants that physically isolated them from other pollen sources. The plants will initiate flowering 3-4 weeks after being moved back into the greenhouse. They are out-crossed with the pollen from the surrounding wild-type plants. The seeds collected from each individual transgenic plant are germinated in soil at 25° C. and Ti plants are grown in the greenhouse for further analysis.

Seed Testing

Test of the Transgenic Plants and their Progeny for Resistance to PPT

Transgenic plants and their progeny are evaluated for tolerance to glufosinate (PPT) indicating functional expression of the bar gene. The seedlings are sprayed twice at concentrations of 1-10% (v/v) Finale© (AgrEvo USA, Montvale, N.J.) containing 11% glufosinate as the active ingredient. Resistant and sensitive seedlings are clearly distinguishable 1 week after the application of Finale© in all the sprayings.

Statistical Analysis

Transformation efficiency for a given experiment is estimated by the number of PPT-resistant events recovered per 100 embryogenic calli infected and regeneration efficiency is determined using the number of regenerated events per 100 events attempted. The mean transformation and regeneration efficiencies are determined based on the data obtained from multiple independent experiments. A Chi-square test can be used to determine whether the segregation ratios observed among Ti progeny for the inheritance of the bar gene as a single locus fit the expected 1:1 ratio when out-crossed with pollen from untransformed wild-type plants.

DNA Extraction and Analysis

Genomic DNA is extracted from approximately 0.5-2 g of fresh leaves essentially as described by Luo, et al., (1995) *Mol Breed* 1:51-63. Ten micrograms of DNA is digested with HindIII or BamHI according to the supplier's instructions (New England Biolabs, Beverly, Mass.). Fragments are size-separated through a 1.0% (w/v) agarose gel and blotted onto a Hybond-N+ membrane (Amersham Biosciences, Piscataway, N.J.). The bar gene, isolated by restriction digestion from pTAP-arts/35S-bar, is used as a probe for Southern blot analysis. The DNA fragment is radiolabeled using a Random Priming Labeling kit (Amersham Biosciences) and the Southern blots are processed as described by Sambrook, et al., (1989) Molecular cloning: a laboratory manual, 2nd edn, Cold Spring Harbor Laboratory Press, New York.

Polymerase Chain Reaction

The two primers designed to amplify the bar gene are as follows: 5'-GTCTGCACCATCGTCAACC-3' (SEQ ID NO: 42), corresponding to the proximity of the 5' end of the bar gene and 5'-GAAGTCCAGCTGCCAGAAACC-3' (SEQ ID NO: 43), corresponding to the 3' end of the bar coding region. The amplification of the bar gene using this pair of primers should result in a product of 0.44 kb. The reaction mixtures (25 μl total volume) consist of 50 mM KCl, 10 mM Tris-HCl (pH 8.8), 1.5 mM MgCl2, 0.1% (w/v) Triton X-100, 200 μM each of dATP, dCTP, dGTP and dTTP, 0.5 μM of each primer, 0.2 μg of template DNA and 1 U Taq DNA polymerase (QIAGEN, Valencia, Calif.). Amplification is performed in a Stratagene Robocycler Gradient 96 thermal cycler (La Jolla, Calif.) programmed for 25 cycles of 1 min at 94° C. (denaturation), 2 min at 55° C. (hybridization), 3 min at 72° C. (elongation) and a final elongation step at 72° C. for 10 min. PCR products are separated on a 1.5% (w/v) agarose gel and detected by staining with ethidium bromide.

Example 13

Plant Characterization Analysis—Greenhouse

Greenhouse experiments were performed with two constructs plus a comparative control. All had 35S::BAR as the selectable marker. Php37407 contained S2A PRO::D8 MPL+ F3.7 PRO::CESA4+FTM1 PRO::DD+NAS2 PRO::DD. Php39175 contained S2A PRO::D8MPL S89T (ALT4). For each construct, 10 events were planted. An equal number of positive and negative plants (4 per week×4 weeks) were expected. Due to greenhouse growth conditions and subsequent extra plantings, the outcome of samples was:
For php37407: 28 positive plants from 10 events and 24 negative siblings from 9 events.
For php39175: 25 positive plants from 8 events and 29 negative siblings from 10 events.

Observations were performed on each of the plants, and measurements recorded. Data collected included: Plant Height, Leaf Width and Leaf Length (leaves −2, +2, +4 from ear node), Central Tassel Spike Measurement (absolute value and normalized to height), Anther Exertion Length, Tassel Score (1-9: 1 being very small with no branches, 5 average size with approximately 6 branches, 9 very large with 20 or more branches), Pollen Score (1-5: low to high, a measurement of collected pollen, each unit equivalent to 0.7" of collected pollen in a 0.25" wide apparatus) and Leaf Count.

Final analysis of the plants showed that the stacked php37407 construct containing the dimerization domain had moderating effects on the dwarf gene's phenotype exhibited in php39175 plants. Plant height for php37407 increased 8.8% as compared with php39175. The increases in the leaf width and the reductions in leaf length with the dwarf gene in php39175 were also moderated with the stack in php37407. In the php37407 plants, leaf width was reduced 6% in the leaf two nodes below the ear, 4.2% in the leaf two nodes above the ear and 5.4% in the leaf four nodes above the ear. The leaf lengths in the php37407 plants were increased 2.7% and 2.8% respectively for the nodes two below and two above the ear and showed no difference for the leaf four nodes above the ear. Additionally, the absolute length of the central tassel spike was increased by 3% in the php37407 samples as compared with the php39175 samples. The tassel length as a percentage of height was reduced by 6.4% in php37407, moderating the dwarf gene's effect to increase the relative tassel length compared to the vegetative plant height. Furthermore, on a representative subset of samples, the exerted anther length including the filament plus anther in php37407 plants was increased by 9.9% as compared with the php39175 anthers. In addition, the tassel score index (1-9) taken by the greenhouse in the stacked php37407 plants showed an increase of 9.5%. The pollen score index (1-5) on a representative subset of samples showed no difference between the samples. Leaf counts were also similar between php37407 and php39175 and found one node greater per plant as compared with their negative siblings. Overall, the stack of genes in the php37407 plants displayed a moderating effect of the dwarf gene phenotype in the php39175 samples. Moderating the effect of the dwarf gene included, but was not limited to: increased plant height and tassel size, leaf length and anther exerted.

Example 14

Arabidopsis Dimerization Domain Study

Arabidopsis plants ecotype Columbia were transformed with a construct containing a constitutive promoter or tissue-preferred promoter driving expression of the dimerization domain (DD). Plants were transformed using Agrobacterium-mediated transformation method and positive transformants were selected by resistance to an herbicide. Transgenic Arabidopsis plants were grown in nutrient-rich soil under greenhouse conditions. Seeds were collected to determine improvements in yield or yield-related traits between transgenic plants and control plants. Control plants are positive transformants that contain the vector backbone without the promoter and dimerization domain. Effective transgenic events are those that show an increase in yield or seed weight under normal growing conditions.

Transgenic plants containing a putative leaf-preferred promoter driving expression of the dimerization domain showed an approximately 22% increase in seed weight over control plants.

Example 15

Root Growth Analysis

Seed segregating for transgene heterozygote and wild type are planted in Custom 200C pot filled with Turface MVP then watered with nutrient solution containing 1 mM KNO3 or 4 mM KNO3 as nitrogen source along with a full complement of other nutrients:

| Nutrient | 1 mM KNO$_3$ | 4 mM KNO$_3$ |
|---|---|---|
| 10× Micronutrients | 400 ml | 400 ml |
| KH$_2$PO$_4$ 136.02 Mwt | 272 g | 272 g |
| MgSO$_4$ 120.36 Mwt | 963 g | 963 g |
| KNO$_3$ fertilizer grade | 400 g | 1200 g |
| KCl 74.55 Mwt | 596 g | — |
| *CaCl$_2$ 147.01 Mwt | 588 g | 588 g |
| Sprint 330 | 335 g | 335 g |
| | /100 l | /100 l |

Add 84 ml H$_2$SO$_4$ to reduce pH. Optimum pH is 5-5.5. Add 200 ul of the nutrient solution to 3 ml tap water and check the pH, it should be 5-5.8. If distilled water is used the pH will have to be raised with 10 M KOH instead of decreased.
*If using tap water with Ca$^{++}$ concentration in the 0.5-0.7 mM level reduce this amount to 235 g. If comparing 6 mM growth to any other nutrient mix maintain the CaCl$_2$ level at 588 g/100 l.

| 10× Micronutrients Stock solutionmg | |
|---|---|
| | mg/liter |
| 15 mM H$_3$BO$_3$ | 1852 mg |
| 5 mM MnCl$_2$•4H$_2$O | 1980 mg |
| 5 mM ZnSO$_4$•7 H$_2$O | 2874 mg |
| 0.5 mM CuSO$_4$•5 H$_2$O | 250 mg |
| 0.5 mM H$_2$MoO$_4$•H$_2$O | 242 mg |

After 3 weeks of growth in these media SPAD meter measurements are made by averaging at least 5 readings taken from the base of the youngest most fully expanded leaf. Plants are removed from the pots, the Turface washed from the roots and separated into shoots and roots. These samples are dried (70° C. for 72 hr) and dried roots are weighed separately from the shoots. The dried shoots are ground to a fine powder and total N determined using a sample of the ground tissue. From these parameters greenness (SPAD), total plant weight, shoot weight, root weight, root/shoot ratio, shoot nitrogen concentration and total N are calculated for low and high N fertility grown plants.

Plants have a higher root/shoot ratio when grown in lower nitrogen fertility. Agronomic conditions for growing maize have higher soil nitrate conditions when the plants are the smallest. Higher soil nitrate conditions favor lower root/shoot ratios which does not favor extensive soil exploration by roots. These transgenes that increase the root/shoot ratio under high or low nitrogen fertility would likely explore a greater portion of the soil early during growth and maximize plant growth. Root/shoot ratios would be higher in higher N fertilities.

The use of a root preferred promoter such as NAS2 and the dimerization domain (DD) enhances root growth early in development. The changes in root growth can be detected at the tissue culture stages of plant regeneration following transformation with this gene specifically by the appearance of more roots and larger diameter roots in test tubes prepared for rooting (ref. Zhao). Transgenic seed expressing NAS2:DD would be expected to have an enhanced early root growth phenotype similar to that observed in tissue culture experiments. The expected phenotype in the assay mentioned above would be expected to produce a higher root dry weight at the end of the growth period of three weeks. An altered root growth (higher) would be especially desirable under higher N conditions because of a greater soil exploration capacity in transgenic versus non transgenic plants.

Example 16

The Use of DD (Dimerization Domain) Components with Moderate Dwarfing Genes (D8MPL) to Improve Creeping Bentgrass (*Agrostis stolonifera* L.) for Turf Grass Applications The semi-dwarf characteristics of S2a:D8MPL in corn could be used to improve turf grass species such as creeping bentgrass (*Agrostis stolonifera* L). Specifically, a more compact leaf with increased width and reduced length is desirable and the dark green leaf color observed in corn would be especially desirable in turf grass. In addition to the reduced leaf length with S2a:D8MPL, roots may also have shorter length compared to non transgenic creeping bent grass. The use of the DD dominant negative transgene with a root preferred promoter such as NAS2 could be combined in a transgene stack to selectively increase the root growth relative to a more compact leaf phenotype desired in the leaves. The compact leaf structure would also have advantages in terms of reduced maintenance (mowing) with similar or reduced amounts of added fertilizer. Furthermore, the use of the DD with a root preferred or specific promoter would increase the relative root length and root density compared to the expectation of smaller roots with a dwarf shoot/leaf phenotype. Increasing root length and density, especially earlier in plant development, would aide establishment and could also moderate irrigation requirements for establishment and maintenance of commercial turf grass plantings. Similar advantages are anticipated for non-commercial home use of transgenic *Agrostis* species—ease in establishment because of strong root formation from seedlings and more efficient maintenance in terms of less mowing and irrigation to maintain a desirable turfgrass (i.e., dark green) appearance above ground and deeper more vigorous roots to support leaf growth and turf quality maintenance.

Example 17

Variants of Dimerization Domain Sequences

A. Variant Nucleotide Sequences of Dimerization Domain that do not Alter the Encoded Amino Acid Sequence The dimerization domain nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change. These variants are associated with the ability of the dimerization domain to form defective dimmers thereby preventing the inhibitory response to GA.

B. Variant Amino Acid Sequences of Dimerization Domain Polypeptides

Variant amino acid sequences of the dimerization domain polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of Dimerization Domain Polypeptides

In this example, artificial protein sequences are created having 80%, 85%, 90% and 95% identity relative to the reference protein sequence. This latter effort requires identifying conserved and variable regions from an alignment and then the judicious application of an amino acid substitutions table. These parts will be discussed in more detail below.

Largely, the determination of which amino acid sequences are altered is made based on the conserved regions among dimerization domain protein or among the other dimerization domain polypeptides. It is recognized that conservative substitutions can be made in the conserved regions below without altering function. In addition, one of skill will understand that functional variants of the dimerization domain sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 5.

TABLE 5

| | Substitution Table | | |
|---|---|---|---|
| Amino Acid | Strongly Similar and Optimal Substitution | Rank of Order to Change | Comment |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |

TABLE 5-continued

Substitution Table

| Amino Acid | Strongly Similar and Optimal Substitution | Rank of Order to Change | Comment |
|---|---|---|---|
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the dimerization domain polypeptides are generating having about 80%, 85%, 90% and 95% amino acid identity to the starting unaltered ORF nucleotide sequence of SEQ ID NO: 9.

All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A recombinant nucleic acid encoding a dimerization domain, the dimerization domain comprising the amino acid sequence of SEQ ID NO: 19, wherein the nucleic acid encoding the dimerization domain is operably linked to a tissue-preferred promoter.

2. The isolated nucleic acid of claim 1 comprising the polynucleotide sequence of SEQ ID NO: 9.

3. The isolated nucleic acid of claim 1, wherein the encoded dimerization domain binds to a maize D8 protein or D9 protein to produce a non-functional D8 or D9 dimer.

4. A recombinant expression cassette, comprising the nucleic acid of claim 1, wherein the promoter is selected from the group consisting of a root, ear, tassel or anther preferred promoter.

5. A host cell comprising the expression cassette of claim 4.

6. A transgenic plant comprising the recombinant expression cassette of claim 4.

7. The transgenic plant of claim 6, wherein said plant is a monocot.

8. The transgenic plant of claim 6, wherein said plant is a dicot.

9. The transgenic plant of claim 6, wherein said plant is selected from the group consisting of: maize, soybean, sunflower, sorghum, canola, wheat, alfalfa, cotton, rice, barley, millet, peanut, sugar cane, grass, turfgrass and cocoa.

10. A transgenic seed comprising the recombinant expression cassette of claim 4.

11. A method of modulating plant tissue growth with a dimerization domain in a plant, comprising expressing a recombinant expression cassette comprising the polynucleotide of claim 2 operably linked to a promoter.

12. The method of claim 11, wherein said modulation of plant tissue growth is due to reduced inhibition by endogenous gibberellic acid.

13. The method of claim 11, wherein the plant is selected from the group consisting of: maize, soybean, sorghum, canola, wheat, alfalfa, cotton, rice, barley, millet, peanut, sugar cane, grass, turfgrass and cocoa.

* * * * *